(12) United States Patent
Roche et al.

(10) Patent No.: US 8,575,161 B2
(45) Date of Patent: Nov. 5, 2013

(54) BENZOFURANE, BENZOTHIOPHENE, BENZOTHIAZOL DERIVATIVES AS FXR MODULATORS

(75) Inventors: Didier Roche, Ecully (FR); Gisèle Mautino, Chenneviére sur Marne (FR); Ingo Kober, Gross-Gerau (DE); Francis Contard, Lyons (FR); Serge Christmann-Franck, Antony (FR); Saumitra Sengupta, Kolkata (IN); Ramesh Sistla, Bangalore (IN); Gummadi Venkateshwar Rao, Bangalore (IN)

(73) Assignee: Merck Patent GmbH, Darmstadt (DE)

( * ) Notice: Subject to any disclaimer, the term of this patent is extended or adjusted under 35 U.S.C. 154(b) by 288 days.

(21) Appl. No.: 12/988,147

(22) PCT Filed: Mar. 30, 2009

(86) PCT No.: PCT/EP2009/002297
§ 371 (c)(1),
(2), (4) Date: Jan. 5, 2011

(87) PCT Pub. No.: WO2009/127321
PCT Pub. Date: Oct. 22, 2009

(65) Prior Publication Data
US 2011/0105475 A1    May 5, 2011

(30) Foreign Application Priority Data

Apr. 18, 2008 (EP) .................................... 08300183

(51) Int. Cl.
| | | |
|---|---|---|
| *A61P 3/00* | (2006.01) | |
| *A61K 31/343* | (2006.01) | |
| *C07D 307/85* | (2006.01) | |
| *C07D 405/04* | (2006.01) | |
| *C07D 405/12* | (2006.01) | |

(52) U.S. Cl.
USPC .............. 514/233.5; 514/252.11; 514/253.11; 514/254.01; 514/254.04; 514/254.06; 514/254.07; 514/254.11; 544/121; 544/357; 544/364; 544/366; 544/367; 544/370; 544/372; 544/376; 544/377

(58) Field of Classification Search
USPC .................. 514/248, 252.13, 253.04, 254.04, 514/254.09, 254.11, 255.01, 255.02, 514/255.03, 233.5, 252.11, 253.11, 254.01, 514/254.06, 254.07; 544/235, 236, 362, 544/368, 373, 376, 382, 384, 385, 389, 391, 544/392, 403, 121, 357, 364, 366, 367, 370, 544/372, 377

See application file for complete search history.

(56) References Cited

U.S. PATENT DOCUMENTS

| | | | |
|---|---|---|---|
| 4,259,338 A | 3/1981 | Paioni et al. | |
| 5,532,241 A | 7/1996 | Bottcher et al. | |
| 5,723,614 A * | 3/1998 | Bathe et al. | 544/376 |
| 6,531,503 B1 | 3/2003 | Bathe et al. | |
| 6,762,300 B2 * | 7/2004 | Bathe et al. | 544/376 |
| 7,244,846 B2 * | 7/2007 | Dorsch et al. | 544/373 |
| 7,348,323 B2 * | 3/2008 | Nettekoven et al. | 514/235.8 |
| 2003/0125558 A1 | 7/2003 | Bathe et al. | |

FOREIGN PATENT DOCUMENTS

| | | |
|---|---|---|
| DE | 4333254 A1 | 4/1995 |
| DE | 19932314 A1 | 1/2001 |
| WO | WO-96 30343 | 10/1996 |
| WO | WO-01 04112 | 1/2001 |
| WO | 2004113325 A1 | 12/2004 |
| WO | 2004113326 A1 | 12/2004 |

OTHER PUBLICATIONS

Pellicciari R et al: "Farnesoid X receptor: from structure to potential clinical applications," (Journal of Medicinal Chemistry), Aug. 25, 2005, pp. 5383-5403, vol. 48, No. 17.
World Intellectual Property Organization. "International Search Report." PCT/EP2009/002297, Applicant: MERCK Patent GMBH, Mailed Jul. 28, 2009.

* cited by examiner

*Primary Examiner* — Brenda Coleman
(74) *Attorney, Agent, or Firm* — Millen, White, Zelano & Branigan, P.C.

(57) ABSTRACT

The present invention relates to compounds of formula (I) wherein the substituents are as defined in the claims, including pharmaceutical compositions thereof and for their use in the treatment and/or prevention and/or amelioration of one or more symptoms of disease or disorders related to the activity of FXR. The invention is also directed to intermediates and to a method of preparation of compounds of formula (I).

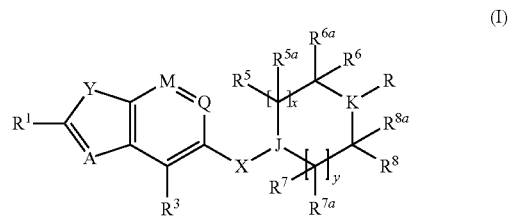

28 Claims, No Drawings

BENZOFURANE, BENZOTHIOPHENE, BENZOTHIAZOL DERIVATIVES AS FXR MODULATORS

This application is a national stage application filed under 35 U.S.C. 371 of PCT/EP2009/002297, filed Mar. 30, 2009.

FIELD OF THE INVENTION

The present invention is related to chemical compositions, processes for the preparation thereof and uses of the composition. Particularly, the present invention relates to compositions of compounds of formula (I):

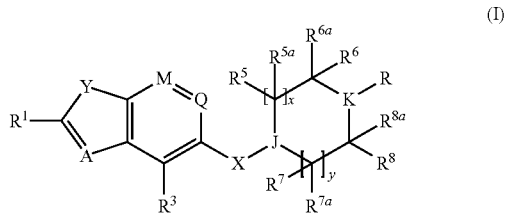

and their use for modulating the activity of FXR receptors and for the treatment, prevention, or amelioration of one or more symptoms of disease or disorder related to the activity of the receptors, including, but not limited to hyper-cholesterolemia, hyperlipoproteinemia, hypertriglyceridemia, dyslipidemia, lipodystrophy, cholestasis/fibrosis, cholesterol gallstone disease, gastrointestinal disease or condition, hyperglycemia, diabetes mellitus, type 2 diabetes, insulin resistance, metabolic inflexibility, nephropathy, liver diseases, atherosclerosis, cancer, inflammatory disorders, obesity, osteoporosis, skin aging, hair growth regulation and pigmentation disorders, Parkinson's disease and/or Alzheimer's disease.

BACKGROUND OF THE INVENTION

Farnesoid X receptor (FXRα, NR1H4) is a member of the nuclear hormone receptor superfamily of ligand-activated transcription factors and was cloned in 1995 (Forman B. M. et al., Cell, 1995, 81, 687-693; Seol W. et al., Mal. Endocrinol., 1995, 9, 72-85).

FXR is highly expressed in the liver, intestine, kidney, adrenal glands, white adipose tissue and is induced during adipocyte differentiation in vitro (Cariou B. et al., J. Biol. Chem., 2006, 16, 11039-11049).

FXR contains a conserved DNA-binding domain (DBD) and a C-terminal ligand binding domain (LBD). The farnesoid X receptor-RXR heterodimer binds with highest affinity to an inverted repeat-1 (IR-1) response element, in which consensus receptor-binding hexamers are separated by one nucleotide. The farnesoid X receptor is part of an interrelated process, in that the receptor is activated by bile acids (the end product of cholesterol metabolism) (see, e.g., Makishima M. et al., Science, 1999, 284, 1362-1365; Parks D. J. et al., Science, 1999, 284, 1365-1368; Wang H. et al., Mol. Cell., 1999, 3, 543-553), which serve to inhibit cholesterol catabolism. See also, Urizar N. L. et al., J. Biol. Chem., 2000, 275, 39313-39317. The single FXRα gene in humans and mice encodes 4 FXRs isoforms (FXRα1, FXRα2, FXRα3 and FXRα4). They differ by their N-terminus and by the insertion/deletion of four amino acids in the hinge region. Many target genes are regulated in an isoform-independent manner.

The second FXR gene FXRβ (NR1H5) has been identified in rodents, dogs and chicken but is a pseudogene in primates and in human (Otte K. et al., Mol. Cell. Biol., 2003, 23, 864-872). FXRβ is a lanosterol sensor and its physiological function remains unclear.

FXR regulates diverse physiological processes. This nuclear receptor is the intracellular bile acid "sensor" and its major physiological role is to protect liver cells from the deleterious effect of Bile Acids (BA) overload. Intestine is the tissue expressing the first FXR target gene identified. Indeed IBAB-P is expressed in enterocytes and binds bile acids, thus limiting the free concentration of BA intracellularly and consequently their toxicity (Makishima M et al., Science, 1999, 284, 1362-1365). FXR is highly expressed in the liver and regulates key genes involved in BA synthesis, metabolism and transport including CYP7A1, UGT2B4, BSEP, MDR3, MRP2, ASBT, NTCP, OSTα and OSTβ in humans. One effect of FXR activation is downregulation of CYP7A1 and thus bile acid synthesis; this is accomplished through induction of SHP (short heterodimer partner) which then represses CYP7A1 transcription (Claudel T. et al., Arterioscler. Thromb. Vasc. Biol., 2005, 25, 2020-2031).

Altered expression or malfunction of these genes has been described in patients with cholestatic liver diseases. A protective role of FXR modulators during cholestasis has been postulated by several studies in various cholestatic animal models (Liu Y. et al., J. Clin. Invest, 2003, 112, 1678-1687). 6-ECDCA was found to fully reverse the impairment of bile flow and to protect the hepatocytes against liver cell injury caused by the cytotoxic lithocholic acid (Pelliciari R. et al., J. Med. Chem., 2003, 45, 3569-3572).

The process of enterohepatic circulation of bile acids is also a major regulator of serum cholesterol homeostasis. After biosynthesis from cholesterol in the liver, BA are secreted with bile into the lumen of the small intestine to aid in the digestion and absorption of fat and fat-soluble vitamins. The ratio of different BA determines the hydrophilicity of the bile acid pool and its ability to solubilize cholesterol. FXR activation increases the hydrophilicity of the pool, decreasing the intestinal solubilization of cholesterol, effectively blocking its absorption. Decrease absorption would be expected to result in lowering of plasma cholesterol levels. Indeed direct inhibitors of cholesterol absorption such as ezetimibe decrease plasma cholesterol, providing some evidence to support this hypothesis. However ezetimibe has limited efficacy which appears due to feedback up-regulation of cholesterol synthesis in cells attempting to compensate for depletion of cholesterol. Recent data have shown that FXR opposes this effect in part by directly repressing the expression of HMG-CoA reductase via a pathway involving SHP and LRH1 (Datta S et al., J. Biol, Chem, 2006, 281, 807-812). In addition, Hubbert M L et al. (Hubbert M et al., Mol Endocrinol, 2007, 21, 1359-1369) reported that FXR induces the expression of hepatic Insig-2, which represses lanosterol 14alpha-demethylase, and reduces HMG-CoA reductase protein levels.

Most patients with coronary artery disease have high plasma levels of atherogenic LDL. The HMGCoA reductase inhibitors (statins) are effective at normalizing LDL-C levels but reduce the risk for cardiovascular events such as stroke and myocardial infarction by only about 30%. Additional therapies targeting further lowering of atherogenic LDL as well as other lipid risk factors such as high plasma triglyceride levels and low HDL-C levels are needed.

Thus FXR constitutes a potential therapeutic target that can be modulated to enhance the removal of cholesterol from the body.

Subsequent studies demonstrated that FXR also regulates a set of genes that control specific aspects of lipoprotein metabolism. Sinai et al. originally proposed that FXR controls plasma lipid levels (Sinai C J et al., Cell, 2000, 102, 731-44). More recently, the FXR agonist GW4064, when used to treat db/db diabetic mice, significantly reduced plasma TG (Zhang Y. et al., Proc. Natl. Acad. Sci., 2006, 103, 1006-1011). FXR activation affects TG metabolism via several pathways. Some mechanisms involved in the reduction of TG include down-regulation of the transcription factor sterol regulatory element-binding protein 1c α (Pineda-Torra I. et al., Mol. Endocrinol., 2005, 17, 259-272), down-regulation of apoC-III (Claudel T. et al., Gastroenterology, 2003, 125, 544-555), up-regulation of apoC-II (Kast H. R. et al., Mol. Endocrinol., 2001, 15, 1720-1728) and up-regulation of syndecan-1 and the VLDL receptor. Increasing fatty acid oxidation represents another means for FXR mediated reduction of plasma triglyceride levels by up-regulating pyruvate dehydrogenase kinase (PDK4) (Savkur R. S. et al., Biochem Biophys. Res. Commun., 2005, 329, 391-6).

Furthermore, the studies of Edwards P. A. et al. (J. Lipid Res, 2002, 1, 2-12) showed that FXR alters the transcription of several genes involved in fatty acid and triglyceride synthesis, as well as lipoprotein metabolism. These genes include the phospholipid transfer protein (PLTP), the syndecan-1 (SDC-1) and the very low density lipoprotein receptor (VLDLR) (Urizar N. L. et al., J. Biol. Chem., 2000, 275, 39313-39317; Anisfeld A. M. et al., J. Biol. Chem., 2003, 278, 20420-20428; Sirvent A. et al., FEBS Lett., 2004, 566, 173-177). Recently new FXR modulator compounds show the ability to reduce both plasma triglyceride and cholesterol levels in normal and hyperlipidemic animal models (see e.g., International Patent Application Publication No. WO 2007/070796).

Thus compounds which modulate FXR activity may show superior therapeutic efficacy on plasma cholesterol and triglyceride lowering than current therapies.

FXR activation has also been described to downregulate proinflammatory enzymes iNOS and COX-2, as well as migration of vascular smooth muscle cell migration (Li YTY et al., Arterioscler Thromb Vasc Biol., 2007, 27, 2606-2611). This protective effect of FXR agonists on atherosclerosis plaque stability may be of valuable interest also in the treatment of inflammation in diabetic nephropathy.

Interesting results have been obtained with BA sequestrants in a randomized, double band crossover trial. The administration of cholestyramine improved glycemic control in patients with type 2 diabetes and dyslipidemia (Garg A et al., Ann Intern Med, 1994, 121, 416-422). Several recent studies have demonstrated that FXR plays a role in glucose metabolism. Mice treated with GW4064 or cholic acid or after infection with a FXR-VP16 fusion protein adenovirus resulted in a significant decrease of plasma glucose levels and improved insulin sensitivity in three diabetic models (db/db, ob/ob and KK-A(y) mice) (Cariou B. et al., J. Biol. Chem., 2006, 281, 11039-11049; Zhang Y. et al., Proc. Natl. Acad. Sci., 2006, 103, 1006-1011; Ma K. et al., J. Clin. Invest., 2006, 116, 1102-1109). Consistent with these data, Fxr mice show impaired glucose tolerance and insulin resistance (Cariou B. et al., J. Biol. Chem., 2006, 16, 11039-11049). FXR expression is also stimulated by glucose and repressed by insulin in rat primary hepatocytes (Duran-Sandoval D. et al., Diabetes, 2004, 53, 890-898). GW4064 treatment reduces phosphoenol pyruvate carboxykinase (PEPCK) and glucose-6-phosphatase (G6 Pase) expression in diabetic db/db mice but GW4064 induces PEPCK expression and increases glucose output in primary hepatocytes in vitro (Stayrook K. R. et al., Endocrinology, 2005, 146, 984-991).

In the case of diabetes of the type 2 elevated blood glucose per se is associated with increased and premature mortality due to an increased risk for microvascular and macrovascular diseases, including retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys), hypertension, cerebrovascular disease and coronary heart disease. Therefore, control of glucose homeostasis is an important approach for the treatment of diabetes. Thus, FXR modulators have been disclosed as useful for the treatment, prevention, or amelioration of one or more of the symptoms of insulin insensitivity or resistance or for the treatment of the complications of hyperglycemia (see, e.g., International Patent Application Publication No. WO 01/82917) Based on these findings, FXR selective modulators are potential pharmaceutical candidates for the management of type 2 diabetes and hypertriglyceridemia, which are two major symptoms of metabolic syndrome.

FXR modulators are also suitable for treating obesity, as well as for treating the complications of obesity. The terms "obese" and "obesity" refer to, according to the World Health Organization, a Body Mass Index (BMI) greater than 27.8 $kg/m^2$ for men and 27.3 $kg/m^2$ for women (BMI equals weight (kg)/height (meters squared). Obesity is linked to a variety of medical conditions including diabetes and an atherosclerotic disease event. (See, e.g., Barrett-Conner E., Epidemiol. Rev., 1989, 11, 172-181; Tulloch-Reid M. K. et al., Diabetes Care, 2003, 26, 2556-2561).

Recent studies have demonstrated the involvement of FXR in cancer pathology as liver cancer (Yang F. et al., Cancer Res., 2007, 67, 863-867); breast cancer (Swales K. E. et al., Cancer Res., 2006, 66, 10120-10126); colorectal cancer (De Gottardi A. et al, Dig Dis Sci 2004, 49, 982-989; Debruyne P. R. et al., Oncogene 2002, 21, 6740-6750); esophagus cancer (De Gottardi A. et al., Mol Cancer, 2006, 5, 48-57).

Nuclear receptor activity, including the farnesoid X receptor and/or orphan nuclear receptor activity, has been implicated in a variety of diseases and disorders, including, but not limited to disorders of the skin and mucous membranes and acne (see, e.g., U.S. Pat. Nos. 6,071,955 and 6,187,814), Parkinson's disease (Sacchetti P. et al., Nucleic Acids Res., 2006, 34, 5515-5527) and Alzheimer's disease (Wolozin B., Neuron, 2004, 41, 7-10).

Thus, there is a need for novel classes of compounds that possess the beneficial properties. It has been discovered that a class of compounds, referred to herein as compounds of formula (I), are useful as agents for treating or preventing various diseases or disorders disclosed herein.

SUMMARY OF THE INVENTION

The present invention in one aspect is directed to various novel compounds of structure:

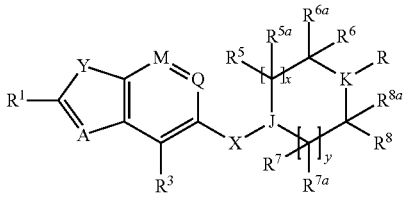

and its stereoisomeric forms, mixtures of stereoisomeric forms, or pharmaceutically acceptable salt forms thereof, wherein the constituent members are defined infra.

Another object of the present invention is to provide pharmaceutical compositions comprising the compounds of the present invention wherein the compositions comprise one or more pharmaceutically acceptable excipients and a therapeutically effective amount of at least one of the compounds of the present invention, or a pharmaceutically acceptable salt or ester form thereof.

Another object of the present invention is to provide methods for the treatment, prevention, or amelioration of one or more symptoms of disease or disorder related to the activity of the receptors, including, but not limited to, hypercholesterolemia, hyperlipoproteinemia, hypertriglyceridemia, dyslipidemia, lipodystrophy, cholestasis/fibrosis, cholesterol gallstone disease, gastrointestinal disease or condition, hyperglycemia, diabetes mellitus, type 2 diabetes, insulin resistance, metabolic inflexibility, nephropathy, liver diseases, atherosclerosis, cancer, inflammatory disorders, obesity, osteoporosis, skin aging, hair growth regulation and pigmentation disorders, Parkinson's disease and/or Alzeihmer's disease.

These and other objects, features and advantages of the compounds of formula (I) will be disclosed in the following detailed description of the patent disclosure.

DETAILED DESCRIPTION OF THE INVENTION

According to a first object, the present invention provides novel compounds of formula (I):

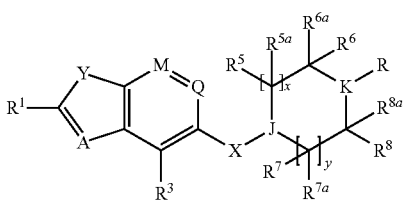

wherein
A is $CR^2$ or N;
Y is $CR^{2a}R^{2b}$, O, S or —$N(R^0)$—, provided that when Y is —$N(R^0)$—, A is $CR^2$;
M, Q are each independently $C$—$R^{2c}$ or N;
—X— is a single bond, or is —$NR^{15}$—;
J, K are each independently CH or N;
R is
a 5 to 10-membered heterocyclic ring optionally substituted by 1 to 3 $R^{16}$; or
R and $R^6$, $R^{6a}$ together, or R and $R^8$, $R^{8a}$ together, form with the atoms to which they are attached a 5 or 6 carbocyclic ring; or R is $VR^4$, wherein:
V is selected from $C_1$-$C_6$ alkylene, $C_6$-$C_{10}$ arylene, 5 to 10-membered heteroarylene, O, CO, $S(O)z$, $NR^{15}$, (alkylene)-$S(O)_z$—, $S(O)_z$-(alkylene)-, $NR^{11}CO$, $CONR^{11}$, $NR^{11}$—$S(O)_z$ or $S(O)_z$—$NR^{11}$, wherein said alkylene groups are optionally substituted by $C_1$-$C_6$ alkyl or $C_6$-$C_{10}$ aryl; and
$R^4$ is $C_1$-$C_6$ alkyl, $NR^{12}R^{13}$, $OR^{15}$, (alkylene)-CN, $C_3$-$C_{10}$ carbocyclic ring, $C_6$-$C_{10}$ aryl, aralkyl, $C_6$-$C_{10}$ aryloxy, 5 to 10-membered heterocyclic ring,
wherein said heterocyclic group is optionally substituted by $C_6$-$C_{10}$ aryl, or a 5 to 10-membered heterocyclic group, and
wherein said aryl and heterocyclic groups are optionally substituted by 1 to 3 $R^{14}$ groups;
$R^0$ is H, $C_1$-$C_6$ alkyl, $C_1$-$C_6$ halogenoalkyl, $C_2$-$C_6$ alkenyl, $C_2$-$C_6$ alkynyl;
$R^1$ is $CO_2R^{15}$, $CONR^9R^{10}$, $COR^{15}$, CN, (alkylene)-CN, $CH(OH)R^{15}$, $C(OH)R^{15}R^{15a}$, $SO_2R^{15}$, $SO_2NR^9R^{10}$, $C(=O)NOR^{15}$, 5 to 10-membered heteroaryl, $C_1$-$C_6$ alkyl, $C_1$-$C_6$ halogenoalkyl, $C_2$-$C_6$ alkenyl, $C_2$-$C_6$ alkynyl, $C_6$-$C_{10}$ aryl, $NR^9R^{10}$;
$R^2$ is H, $C_1$-$C_6$ alkyl, $C_1$-$C_6$ halogenoalkyl, $C_2$-$C_6$ alkenyl, $C_2$-$C_6$ alkynyl, $C_3$-$C_{10}$ cycloalkyl, $C_1$-$C_6$ alkoxy, $C_6$-$C_{10}$ aryl, aralkyl, 5 to 10-membered heteroaryl, CN, halogen;
$R^{2a}$ and $R^{2b}$ are each independently selected from $C_1$-$C_6$ alkyl, $C_1$-$C_6$ halogenoalkyl, $C_2$-$C_6$ alkenyl, $C_2$-$C_6$ alkynyl, $C_3$-$C_{10}$ cycloalkyl, $C_6$-$C_{10}$ aryl, aralkyl or 5 to 10-membered heteroaryl;
$R^{2c}$ is H, $C_1$-$C_6$ alkyl, $C_1$-$C_6$ alkoxy, or halogen;
$R^3$ is H, halogen, $C_1$-$C_6$ alkyl, $C_1$-$C_6$ halogenoalkyl, $C_2$-$C_6$ alkenyl, $C_2$-$C_6$ alkynyl, $C_1$-$C_6$ alkoxy, $C_1$-$C_6$ halogenoalkoxy, CN, $C_6$-$C_{10}$ aryl or 5 to 10-membered heteroaryl;
$R^5$, $R^{5a}$, $R^6$, $R^{6a}$, $R^7$, $R^{7a}$, $R^8$, $R^{8a}$ are each independently selected from:
H, $C_1$-$C_6$ alkyl, $C_1$-$C_6$ halogenoalkyl, $C_2$-$C_6$ alkenyl or $C_2$-$C_6$ alkynyl; or
a group wherein $R^5$ and $R^{5a}$ together, or $R^6$ and $R^{6a}$ together, or $R^7$ and $R^{7a}$ together, or $R^8$ and $R^{8a}$ together form a =O moiety; or
$R^5$, $R^{5a}$ together, and/or $R^6$, $R^{6a}$ together, and/or $R^7$, $R^{7a}$ together, and/or $R^8$ and $R^{8a}$ together, form with the carbon atom(s) to which they are attached a $C_3$-$C_9$ cycloalkyl, $C_3$-$C_9$ cycloalkoxy; or
one group selected from $R^5$, $R^{5a}$, $R^6$ or $R^{6a}$ together with one group selected from $R^7$, $R^{7a}$, $R^8$ or $R^{8a}$ form a $C_1$-$C_6$ alkylene or $C_1$-$C_6$ alkylenoxy group;
$R^9$, $R^{10}$ at each occurrence are each independently selected from H, $C_1$-$C_6$ alkyl, $C_1$-$C_6$ halogenoalkyl, $C_2$-$C_6$ alkenyl, $C_2$-$C_6$ alkynyl, $C_1$-$C_6$ alkoxyalkyl, dialkylaminoalkyl, or together form with the nitrogen atom to which they are attached to a 5 to 10-membered heterocyclic ring;
$R^{11}$ at each occurrence is selected from H, $C_6$-$C_{10}$ aryl, and aralkyl, wherein said aryl groups are optionally substituted by 1 to 3 halogen;
$R^{12}$, $R^{13}$ at each occurrence are each independently selected from H, $C_1$-$C_6$ alkyl, $C_1$-$C_6$ halogenoalkyl, $C_2$-$C_6$ alkenyl, $C_2$-$C_6$ alkynyl, $C_3$-$C_7$ cycloalkylalkyl, $C_6$-$C_{10}$ aryl wherein said aryl group is optionally substituted by one to three $R^{14}$;
$R^{14}$ at each occurrence is independently selected from F, Cl, Br, OH, $C_1$-$C_6$ alkyl, $C_1$-$C_6$ halogenoalkyl, $C_2$-$C_6$ alkenyl, $C_2$-$C_6$ alkynyl, $CO_2R^{15}$, $C_1$-$C_6$ alkoxy, $C_6$-$C_{10}$ aryloxy, $CF_3$, $OCF_3$, CN;
$R^{15}$ and $R^{15a}$ at each occurrence are each independently selected from H, $C_1$-$C_6$ alkyl, $C_1$-$C_6$ halogenoalkyl, $C_2$-$C_6$ alkenyl, $C_2$-$C_6$ alkynyl, or $C_6$-$C_{10}$ aryl;

$R^{16}$ is independently selected from $C_1$-$C_6$ alkyl, $C_1$-$C_6$ halogenoalkyl, $C_2$-$C_6$ alkenyl, $C_2$-$C_6$ alkynyl, halogen, or $C_6$-$C_{10}$ aryl, wherein said aryl group is optionally substituted by $C_1$-$C_6$ alkyl, halogen, $C_1$-$C_6$ alkoxy;

x is 0, 1, 2, 3, or 4;
y is 0, 1, 2, 3 or 4;
z is 0, 1 or 2;
and the stereoisomeric forms, mixtures of stereoisomeric forms or pharmaceutically acceptable salts forms thereof.

Preferably, Y is O or S.
Preferably, A is $CR^2$.
In a preferred aspect, the compound of formula (I) is a compound of formula (A):

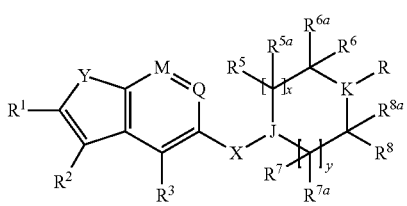

(I)

Preferably, $R^2$ is H.
Preferably, M and Q are CH or N, more preferably CH.
Preferably, $R^5$, $R^{5a}$, $R^6$, $R^{6a}$, $R^7$, $R^{7a}$, $R^8$ and/or $R^{8a}$ is/are H.

In a preferred embodiment, there are included compounds of formula (Ia):

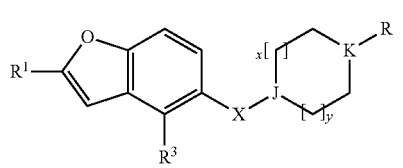

(Ia)

Preferably, x and/or y is/are 1 or 2.
Preferably, —X— is a single bond, which means that the aromatic or heteroaromatic ring (including M, Q substituents) is directly connected to the cyclic ring (including the substituents J, K).
Preferably, R is $VR^4$.
In a preferred embodiment, there are included compounds of formula (Ib):

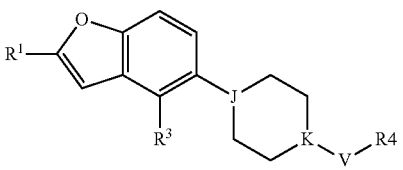

(Ib)

Preferably, $R^1$ is $CO_2R^{15}$, $CONR^9R^{10}$ or a 5 to 10-membered heteroaryl, more preferably $CO_2H$, $CONH_2$.
Preferably, $R^3$ is H, $C_1$-$C_6$ alkyl, $C_1$-$C_6$ halogenoalkyl or halogen.
Preferably, J is N.
Preferably, K is N.
Preferably, V is $C_1$-$C_6$ alkylene, O, CO, $S(O)_z$, (alkylene)-$S(O)_z$, $S(O)_z$-(alkylene), $NR^{11}CO$ or $CONR^{11}$, notably $S(O)_2$, (alkylene)-$S(O)_2$—, $S(O)_2$-(alkylene), $NR^{11}CO$.

More preferably, V is O, CO, $SO_2$, $CH_2$, $CH_2SO_2$, $SO_2CH_2$.
Most preferably, V is O, CO, $SO_2$, $CH_2$.
Preferably, $R^4$ is chosen from the groups selected within:
$OR^{15}$, notably $C_1$-$C_6$ alkoxy, such as t-butoxy;
$NR^{12}R^{13}$, with $R^{12}$, $R^{13}$, representing independently H, $C_1$-$C_6$ alkyl;
$C_3$-$C_{10}$ carbocyclic ring, notably $C_3$-$C_{10}$ cycloalkyl, such as cyclopropyl or adamantyl;
$C_6$-$C_{10}$ aryl, notably phenyl optionally substituted by one or two F and/or Cl;
5 to 10-membered heterocyclic ring, such as pyrrolidinyl, benzoimidazolyl, pyridinyl, pyrimidinyl, thiophenyl, or isoxazolyl;
wherein said aryl and heterocyclic groups are optionally substituted by 1 to 3 $R^{14}$ groups, notably selected from Cl, F, $C_1$-$C_6$ alkyl, $CF_3$ and $CO_2R^{15}$.

More preferably, $R^4$ is chosen from $C_1$-$C_6$ alkoxy, $C_6$-$C_{10}$ aryl, 5 to 10-membered heterocyclic ring.

The invention also relates to the racemic forms, tautomeric forms, enantiomers, diastereoisomers, epimers and organic or mineral salts of the compounds of the general formula (I), as well as their crystalline forms, including their polymorphic forms and the polymorphic forms of the compounds of formula (I).

The present invention is directed not only to racemic mixtures of these compounds, but also to individual stereoisomers and/or diastereoisomers thereof as well or as mixtures of these in all proportions.

The invention also relates to the stereoisomers (including E, Z isomers) and the hydrates and solvates of these compounds. Solvates of the compounds are taken to mean adductions of inert solvent molecules onto the compounds which form owing to their mutual attractive force. Solvates are, for example, mono- or dihydrates or alcoholates.

Pharmaceutically usable derivatives is taken to mean, for example, the salts of the compounds according to the invention and also so-called prodrug compounds.

Prodrug derivatives is taken to mean compounds of the formula I which have been modified, with, for example, alkyl or acyl groups, sugars or oligopeptides and which are rapidly cleaved in the organism to form the active compounds according to the invention.

These also include biodegradable polymer derivatives of the compounds according to the invention, as is described, for example, in Int. J. Pharm. 115, 61-67 (1995).

The term "prodrug" as used herein refers to any compound that when administered to a biological system generates the "drug" substance (a biologically active compound) as a result of spontaneous chemical reaction(s), enzyme catalyzed chemical reaction(s), and/or metabolic chemical reaction(s).

Preferred compounds of formula (I) can be chosen from:
4-(4-Bromo-2-ethoxycarbonyl-benzofuran-5-yl)-piperazine-1-carboxylic acid tert-butyl ester
4-(4-Bromo-2-carboxy-benzofuran-5-yl)-piperazine-1-carboxylic acid tert-butyl ester
4-(2-Carboxy-benzofuran-5-yl)-piperazine-1-carboxylic acid tert-butyl ester
5-[4-(3-Methoxy-benzenesulfonyl)-piperazin-1-yl]-benzofuran-2-carboxylic acid amide
5-[4-(4-Methoxy-benzenesulfonyl)-piperazin-1-yl]-benzofuran-2-carboxylic acid amide
4-(2-Ethoxycarbonyl-benzofuran-5-yl)-piperazine-1-carboxylic acid tert-butyl ester
5-[4-(3-Trifluoromethyl-benzyl)-piperazin-1-yl]-benzofuran-2-carboxylic acid amide
5-[4-(3-Chloro-benzyl)-piperazin-1-yl]-benzofuran-2-carboxylic acid amide 5-[4-(3-Fluoro-benzoyl)-piperazin-1-yl]-benzofuran-2-carboxylic acid amide
5-[4-(3-Chloro-benzenesulfonyl)-piperazin-1-yl]-benzofuran-2-carboxylic acid amide
4-Bromo-5-[4-(4-methoxy-benzenesulfonyl)-piperazin-1-yl]-benzofuran-2-carboxylic acid amide
5-(4-Benzenesulfonyl-piperazin-1-yl)-benzofuran-2-carboxylic acid
4-Bromo-5-[4-(3-fluoro-benzoyl)-piperazin-1-yl]-benzofuran-2-carboxylic acid
4-Bromo-5-[4-(3-chloro-benzenesulfonyl)-piperazin-1-yl]-benzofuran-2-carboxylic acid
4-Bromo-5-[4-(3-fluoro-benzenesulfonyl)-piperazin-1-yl]-benzofuran-2-carboxylic acid
4-Bromo-5-[4-(pyrrolidine-1-carbonyl)-piperazin-1-yl]-benzofuran-2-carboxylic acid
4-Bromo-5-[4-(3-chloro-benzyl)-piperazin-1-yl]-benzofuran-2-carboxylic acid
4-(2-Carboxy-benzofuran-5-ylamino)-piperidine-1-carboxylic acid tert-butyl ester
2-[4-(4-Bromo-2-carboxy-benzofuran-5-yl)-piperazine-1-carbonyl]-pyrrolidine-1-carboxylic acid tert-butyl ester
4-(4-Chloro-2-ethoxycarbonyl-benzofuran-5-yl)-piperazine-1-carboxylic acid tert-butyl ester
4-(2-Carboxy-4-chloro-benzofuran-5-yl)-piperazine-1-carboxylic acid tert-butyl ester
5-(4-Benzyl-piperazin-1-yl)-benzofuran-2-carboxylic acid
4-Bromo-5-[4-(3-trifluoromethyl-benzyl)-piperazin-1-yl]-benzofuran-2-carboxylic acid
5-[4-(3-Methoxy-benzenesulfonyl)-piperazin-1-yl]-benzofuran-2-carboxylic acid
4-Bromo-5-[4-(3-methoxy-benzenesulfonyl)-piperazin-1-yl]-benzofuran-2-carboxylic acid
4-Bromo-5-[4-(4-methoxy-benzenesulfonyl)-piperazin-1-yl]-benzofuran-2-carboxylic acid
4-Bromo-5-[4-(pyrrolidine-2-carbonyl)-piperazin-1-yl]-benzofuran-2-carboxylic acid
5-[4-(Adamantane-1-carbonyl)-piperazin-1-yl]-4-bromo-benzofuran-2-carboxylic acid
4-Bromo-5-[4-(3-chloro-benzoyl)-piperazin-1-yl]-benzofuran-2-carboxylic acid
4-Bromo-5-[4-(2-fluoro-benzyl)-piperazin-1-yl]-benzofuran-2-carboxylic acid
4-Bromo-5-[4-(3-fluoro-benzyl)-piperazin-1-yl]-benzofuran-2-carboxylic acid
5-(4-Benzoyl-piperazin-1-yl)-4-bromo-benzofuran-2-carboxylic acid
5-[4-(3,5-Difluoro-benzyl)-piperazin-1-yl]-benzofuran-2-carboxylic acid amide
4-Bromo-5-[4-(3-trifluoromethyl-benzyloxy)-piperidin-1-yl]-benzofuran-2-carboxylic acid
4-Bromo-5-[4-(3-chloro-benzyloxy)-piperidin-1-yl]-benzofuran-2-carboxylic acid
4-Bromo-5-[4-(2-chloro-benzenesulfonyl)-piperazin-1-yl]-benzofuran-2-carboxylic acid
4-Bromo-5-[4-(4-chloro-benzenesulfonyl)-piperazin-1-yl]-benzofuran-2-carboxylic acid
4-Bromo-5-[4-(4-fluoro-benzyl)-piperazin-1-yl]-benzofuran-2-carboxylic acid
4-Bromo-5-[4-(2-chloro-benzyl)-piperazin-1-yl]-benzofuran-2-carboxylic acid
4-Bromo-5-[4-(4-chloro-benzyl)-piperazin-1-yl]-benzofuran-2-carboxylic acid
4-Bromo-5-[4-(pyridin-2-yloxy)-piperidin-1-yl]-benzofuran-2-carboxylic acid
4-Bromo-5-[4-(3-trifluoromethyl-benzyl)-piperazin-1-yl]-benzofuran-2-carboxylic acid amide
5-[4-(3-Trifluoromethoxy-benzyl)-piperazin-1-yl]-benzofuran-2-carboxylic acid amide
4-Bromo-5-[4-(3-trifluoromethoxy-benzyl)-piperazin-1-yl]-benzofuran-2-carboxylic acid amide
4-Bromo-5-[4-(3-cyano-benzenesulfonyl)-piperazin-1-yl]-benzofuran-2-carboxylic acid
4-Bromo-5-(4-tert-butylcarbamoyl-piperazin-1-yl)-benzofuran-2-carboxylic acid
4-Bromo-5-[4-(3-fluoro-benzenesulfonyl)-piperazin-1-yl]-benzofuran-2-carboxylic acid amide
4-Bromo-5-[4-(3,5-dichloro-benzoyl)-piperazin-1-yl]-benzofuran-2-carboxylic acid amide
4-Bromo-5-[4-(3,5-difluoro-benzyl)-piperazin-1-yl]-benzofuran-2-carboxylic acid amide
4-Bromo-5-(4-pyridin-3-ylmethyl-piperazin-1-yl)-benzofuran-2-carboxylic acid
4-Bromo-5-(4-pyridin-4-ylmethyl-piperazin-1-yl)-benzofuran-2-carboxylic acid
4-Bromo-5-[4-(3-trifluoromethoxy-benzyl)-piperazin-1-yl]-benzofuran-2-carboxylic acid
4-Bromo-5-[4-(3-phenoxy-benzyl)-piperazin-1-yl]-benzofuran-2-carboxylic acid
4-Bromo-5-[4-(3,5-dimethoxy-benzyl)-piperazin-1-yl]-benzofuran-2-carboxylic acid
5-[4-(3-Allyl-2-hydroxy-benzyl)-piperazin-1-yl]-4-bromo-benzofuran-2-carboxylic acid
5-(4-Benzenesulfonyl-piperazin-1-yl)-4-bromo-benzofuran-2-carboxylic acid
4-Bromo-5-(4-tert-butylcarbamoyl-piperidin-1-yl)-benzofuran-2-carboxylic acid
4-Chloro-5-[4-(2-chloro-benzyl)-piperazin-1-yl]-benzofuran-2-carboxylic acid
4-Chloro-5-[4-(3-chloro-benzyl)-piperazin-1-yl]-benzofuran-2-carboxylic acid
4-Chloro-5-[4-(4-chloro-benzyl)-piperazin-1-yl]-benzofuran-2-carboxylic acid
4-Chloro-5-[4-(2-fluoro-benzyl)-piperazin-1-yl]-benzofuran-2-carboxylic acid
4-Chloro-5-[4-(3-fluoro-benzyl)-piperazin-1-yl]-benzofuran-2-carboxylic acid
4-Chloro-5-[4-(4-fluoro-benzyl)-piperazin-1-yl]-benzofuran-2-carboxylic acid
4-Chloro-5-[4-(3-trifluoromethyl-benzyl)-piperazin-1-yl]-benzofuran-2-carboxylic acid
4-Chloro-5-[4-(3-trifluoromethoxy-benzyl)-piperazin-1-yl]-benzofuran-2-carboxylic acid
5-[4-(3-Carboxy-benzyl)-piperazin-1-yl]-4-chloro-benzofuran-2-carboxylic acid
4-Chloro-5-(4-pyridin-3-ylmethyl-piperazin-1-yl)-benzofuran-2-carboxylic acid
4-Chloro-5-[4-(2-chloro-benzenesulfonyl)-piperazin-1-yl]-benzofuran-2-carboxylic acid
4-Chloro-5-[4-(3-chloro-benzenesulfonyl)-piperazin-1-yl]-benzofuran-2-carboxylic acid
4-Chloro-5-[4-(4-chloro-benzenesulfonyl)-piperazin-1-yl]-benzofuran-2-carboxylic acid
4-Chloro-5-[4-(4-methoxy-benzenesulfonyl)-piperazin-1-yl]-benzofuran-2-carboxylic acid
4-Chloro-5-[4-(3-methoxy-benzenesulfonyl)-piperazin-1-yl]-benzofuran-2-carboxylic acid
4-Chloro-5-[4-(3-fluoro-benzoyl)-piperazin-1-yl]-benzofuran-2-carboxylic acid
4-Chloro-5-[4-(3,5-dichloro-benzoyl)-piperazin-1-yl]-benzofuran-2-carboxylic acid
4-Chloro-5-[4-(3-fluoro-benzenesulfonyl)-piperazin-1-yl]-benzofuran-2-carboxylic acid 4-Chloro-5-[4-(3-cyano-benzenesulfonyl)-piperazin-1-yl]-benzofuran-2-carboxylic acid
4-Bromo-5-[4-(2-chloro-benzenesulfonyl)-piperazin-1-yl]-benzofuran-2-carboxylic acid amide
4-Bromo-5-[4-(3-fluoro-benzenesulfonyl)-piperazin-1-yl]-benzofuran-2-carboxylic acid ethoxy-amide
4-Bromo-5-[4-(3-trifluoromethyl-benzoyl)-piperazin-1-yl]-benzofuran-2-carboxylic acid
4-Bromo-5-[4-(3-trifluoromethoxy-benzoyl)-piperazin-1-yl]-benzofuran-2-carboxylic acid
4-Bromo-5-[4-(3-methoxy-benzoyl)-piperazin-1-yl]-benzofuran-2-carboxylic acid
4-Bromo-5-[4-(2,5-dichloro-benzoyl)-piperazin-1-yl]-benzofuran-2-carboxylic acid
4-Bromo-5-[4-(3,5-dichloro-benzoyl)-piperazin-1-yl]-benzofuran-2-carboxylic acid
4-Bromo-5-[4-(2-methyl-1H-benzoimidazole-4-carbonyl)-piperazin-1-yl]-benzofuran-2-carboxylic acid
4-Bromo-5-[4-(5-trifluoromethyl-pyridin-2-yloxy)-piperidin-1-yl]-benzofuran-2-carboxylic acid
4-Bromo-5-[1-(3-chloro-benzyl)-piperidin-4-ylamino]-benzofuran-2-carboxylic acid
4-Chloro-5-[4-(3-chloro-benzoyl)-piperazin-1-yl]-benzofuran-2-carboxylic acid
4-Chloro-5-[4-(2,5-dichloro-benzoyl)-piperazin-1-yl]-benzofuran-2-carboxylic acid
4-Chloro-5-[4-(3-methoxy-benzoyl)-piperazin-1-yl]-benzofuran-2-carboxylic acid
4-Chloro-5-[4-(3-trifluoromethyl-benzoyl)-piperazin-1-yl]-benzofuran-2-carboxylic acid
4-Chloro-5-[4-(3-trifluoromethoxy-benzoyl)-piperazin-1-yl]-benzofuran-2-carboxylic acid
4-Chloro-5-[4-(2-methyl-1H-benzoimidazole-4-carbonyl)-piperazin-1-yl]-benzofuran-2-carboxylic acid
5-[4-(1H-Benzoimidazole-5-carbonyl)-piperazin-1-yl]-4-chloro-benzofuran-2-carboxylic acid
4-Chloro-5-[4-(2,5-dichloro-benzyl)-piperazin-1-yl]-benzofuran-2-carboxylic acid
4-Chloro-5-[4-(3,5-dimethoxy-benzyl)-piperazin-1-yl]-benzofuran-2-carboxylic acid
4-Chloro-5-[4-(3-chloro-phenylmethanesulfonyl)-piperazin-1-yl]-benzofuran-2-carboxylic acid
5-[4-(2-Chloro-benzenesulfonyl)-piperazin-1-yl]-4-methyl-benzofuran-2-carboxylic acid
5-[4-(3-Fluoro-benzenesulfonyl)-piperazin-1-yl]-4-methyl-benzofuran-2-carboxylic acid
4-(2-Carboxy-4-methyl-benzofuran-5-yl)-piperazine-1-carboxylic acid tert-butyl ester
4-(2-Carboxy-4-chloro-benzofuran-5-yl)-[1,4]diazepane-1-carboxylic acid tert-butyl ester
4-(4-Bromo-2-carboxy-benzofuran-5-yl)-[1,4]diazepane-1-carboxylic acid tert-butyl ester
4-Bromo-5-[4-(2-chloro-benzenesulfonyl)-[1,4]diazepan-1-yl]-benzofuran-2-carboxylic acid
4-Chloro-5-[4-(2-chloro-benzenesulfonyl)-[1,4]diazepan-1-yl]-benzofuran-2-carboxylic acid
4-Chloro-5-[4-(5-trifluoromethyl-pyridin-2-yloxy)-piperidin-1-yl]benzofuran-2-carboxylic acid
4-Bromo-5-[1-(3-chloro-benzenesulfonyl)-piperidin-4-ylamino]-benzofuran-2-carboxylic acid
{4-Bromo-5-[4-(2-chloro-benzenesulfonyl)-piperazin-1-yl]-benzofuran-2-yl}-morpholin-4-yl-methanone
4-Bromo-5-[4-(2-chloro-benzenesulfonyl)-piperazin-1-yl]-benzofuran-2-carboxylic acid (2-methoxy-ethyl)-amide
4-Bromo-5-[4-(2,5-dichloro-benzenesulfonyl)-piperazin-1-yl]-benzofuran-2-carboxylic acid
4-Bromo-5-[4-(2,5-dichloro-benzyl)-piperazin-1-yl]-benzofuran-2-carboxylic acid
5-[4-(1H-Benzoimidazole-5-carbonyl)-piperazin-1-yl]-4-bromo-benzofuran-2-carboxylic acid
4-Bromo-5-[4-(2,6-dichloro-benzoyl)-piperazin-1-yl]-benzofuran-2-carboxylic acid
5-[4-(2,6-Dichloro-benzoyl)-piperazin-1-yl]-4-methyl-benzofuran-2-carboxylic acid
5-[4-(2,5-Dichloro-benzoyl)-piperazin-1-yl]-4-methyl-benzofuran-2-carboxylic acid
5-[4-(3,5-Dichloro-benzoyl)-piperazin-1-yl]-4-methyl-benzofuran-2-carboxylic acid
4-Methyl-5-[4-(3-trifluoromethoxy-benzoyl)-piperazin-1-yl]-benzofuran-2-carboxylic acid
5-[4-(2-Chloro-benzyl)-piperazin-1-yl]-4-methyl-benzofuran-2-carboxylic acid
5-[4-(3-Chloro-benzyl)-piperazin-1-yl]-4-methyl-benzofuran-2-carboxylic acid
5-[4-(2,5-Dichloro-benzyl)-piperazin-1-yl]-4-methyl-benzofuran-2-carboxylic acid
5-[4-(3-Fluoro-benzyl)-piperazin-1-yl]-4-methyl-benzofuran-2-carboxylic acid
4-Methyl-5-[4-(3-trifluoromethyl-benzyl)-piperazin-1-yl]-benzofuran-2-carboxylic acid
4-Methyl-5-[4-(3-trifluoromethoxy-benzyl)-piperazin-1-yl]-benzofuran-2-carboxylic acid
5-[4-(3-Chloro-benzenesulfonyl)-piperazin-1-yl]-4-methyl-benzofuran-2-carboxylic acid
5-[4-(2,5-Dichloro-benzenesulfonyl)-piperazin-1-yl]-4-methyl-benzofuran-2-carboxylic acid
5-[4-(3-Chloro-phenylmethanesulfonyl)-piperazin-1-yl]-4-methyl-benzofuran-2-carboxylic acid
4-Bromo-5-[4-(2-chloro-6-fluoro-benzyl)-piperazin-1-yl]-benzofuran-2-carboxylic acid
4-Chloro-5-[4-(2-chloro-6-fluoro-benzyl)-piperazin-1-yl]-benzofuran-2-carboxylic acid
4-Bromo-5-[4-(3-chloro-phenylmethanesulfonyl)-piperazin-1-yl]-benzofuran-2-carboxylic acid
4-Chloro-5-[1-(3-chloro-benzenesulfonyl)-piperidin-4-ylamino]-benzofuran-2-carboxylic acid
4-Bromo-5-(3,4-dihydro-1H-isoquinolin-2-yl)-benzofuran-2-carboxylic acid
4-Bromo-5-[4-(3-chloro-phenoxy)-piperidin-1-yl]-benzofuran-2-carboxylic acid
4-Bromo-5-[4-(4-trifluoromethyl-pyrimidin-2-yloxy)-piperidin-1-yl]-benzofuran-2-carboxylic acid
4-Bromo-5-[4-(2-fluoro-benzenesulfonyl)-piperazin-1-yl]-benzofuran-2-carboxylic acid
5-[4-(2-Fluoro-benzenesulfonyl)-piperazin-1-yl]-4-methyl-benzofuran-2-carboxylic acid
4-Bromo-5-[4-(2,6-dichloro-benzenesulfonyl)-piperazin-1-yl]-benzofuran-2-carboxylic acid
5-[4-(2,6-Dichloro-benzenesulfonyl)-piperazin-1-yl]-4-methyl-benzofuran-2-carboxylic acid
4-Chloro-5-[4-(2,6-dichloro-benzenesulfonyl)-piperazin-1-yl]-benzofuran-2-carboxylic acid
4-Bromo-5-[4-(2,3-dichloro-benzenesulfonyl)-piperazin-1-yl]-benzofuran-2-carboxylic acid
5-[4-(2,3-Dichloro-benzenesulfonyl)-piperazin-1-yl]-4-methyl-benzofuran-2-carboxylic acid
4-Chloro-5-[4-(2,3-dichloro-benzenesulfonyl)-piperazin-1-yl]-benzofuran-2-carboxylic acid
4-Chloro-5-[4-(2,5-dichloro-benzenesulfonyl)-piperazin-1-yl]-benzofuran-2-carboxylic acid
4-Bromo-5-[4-(2,3-dichloro-benzoyl)-piperazin-1-yl]-benzofuran-2-carboxylic acid 4-Methyl-5-[4-(3-trifluoromethyl-benzoyl)-piperazin-1-yl]-benzofuran-2-carboxylic acid
4-Methyl-5-[4-(2-methyl-1H-benzoimidazole-4-carbonyl)-piperazin-1-yl]-benzofuran-2-carboxylic acid
5-[4-(2-Fluoro-benzyl)-piperazin-1-yl]-4-methyl-benzofuran-2-carboxylic acid
5-[4-(2-Chloro-6-fluoro-benzyl)-piperazin-1-yl]-4-methyl-benzofuran-2-carboxylic acid
5-[4-(2,6-Dichloro-benzyl)-piperazin-1-yl]-4-methyl-benzofuran-2-carboxylic acid
4-Bromo-5-[4-(3,5-dichloro-benzyl)-piperazin-1-yl]-benzofuran-2-carboxylic acid
5-[4-(3,5-Dichloro-benzyl)-piperazin-1-yl]-4-methyl-benzofuran-2-carboxylic acid
4-Chloro-5-[4-(3,5-dichloro-benzyl)-piperazin-1-yl]-benzofuran-2-carboxylic acid
5-[4-(3-Allyl-2-hydroxy-benzyl)-piperazin-1-yl]-4-methyl-benzofuran-2-carboxylic acid
5-[4-(2,3-Dimethoxy-benzyl)-piperazin-1-yl]-4-methyl-benzofuran-2-carboxylic acid
4-Bromo-5-[4-(5-chloro-thiophen-2-ylmethyl)-piperazin-1-yl]-benzofuran-2-carboxylic acid
4-Methyl-5-[4-(5-trifluoromethyl-pyridin-2-yloxy)-piperidin-1-yl]-benzofuran-2-carboxylic acid
4-(2-Carboxy-4-cyano-benzofuran-5-yl)piperazine-1-carboxylic acid tert-butyl ester
4-Bromo-5-[4-(4-chloro-phenoxy)-piperidin-1-yl]-benzofuran-2-carboxylic acid
4-Bromo-5-[4-(3-ethoxy-benzyl)-piperazin-1-yl]-benzofuran-2-carboxylic acid
4-Bromo-5-[4-(2-chloro-benzenesulfonyl)-piperazin-1-yl]-benzofuran-2-carboxylic acid benzylamide
5-[4-(3,5-Dichloro-2-hydroxy-benzenesulfonyl)-piperazin-1-yl]-4-methyl-benzofuran-2-carboxylic acid
5-(4-Benzo[1,3]dioxol-4-ylmethyl-piperazin-1-yl)-4-bromo-benzofuran-2-carboxylic acid
4-Bromo-5-[4-(2,6-dichloro-benzyl)-piperazin-1-yl]-benzofuran-2-carboxylic acid
4-Bromo-5-[4-(2,4-dichloro-benzyl)-piperazin-1-yl]-benzofuran-2-carboxylic acid
5-[4-(2-Allyloxy-benzyl)-piperazin-1-yl]-4-bromo-benzofuran-2-carboxylic acid
4-Bromo-5-[4-(3-trifluoromethyl-phenoxy)-piperidin-1-yl]-benzofuran-2-carboxylic acid
4-Bromo-5-[4-(4-trifluoromethyl-phenoxy)-piperidin-1-yl]-benzofuran-2-carboxylic acid
4-Bromo-5-{4-[cyclopropanecarbonyl-(2,4-dichloro-phenyl)-amino]-piperidin-1-yl}-benzofuran-2-carboxylic acid
4-Bromo-5-{-4-[(4-chloro-benzyl)-cyclopropanecarbonyl-amino]-piperidin-1-yl}-benzofuran-2-carboxylic acid
5-{4-[3-(2,6-Dichloro-phenyl)-5-isopropyl-isoxazole-4-carbonyl]-piperazin-1-yl}-4-methyl-benzofuran-2-carboxylic acid
4-Bromo-5-[4-(2-trifluoromethyl-benzyl)-piperazin-1-yl]-benzofuran-2-carboxylic acid
5-[4-(3-Allyloxy-benzyl)-piperazin-1-yl]-4-bromo-benzofuran-2-carboxylic acid
5-[4-(3-Allyl-2-methoxy-benzyl)-piperazin-1-yl]-4-methyl-benzofuran-2-carboxylic acid
4-Bromo-5-[4-(3-tert-butyl-2-hydroxy-benzyl)-piperazin-1-yl]-benzofuran-2-carboxylic acid
4-Methyl-5-(4-naphthalen-1-ylmethyl-piperazin-1-yl)-benzofuran-2-carboxylic acid
4-Bromo-5-[4-(2-hydroxy-naphthalen-1-ylmethyl)-piperazin-1-yl]-benzofuran-2-carboxylic acid
4-Bromo-5-[4-(2-trifluoromethyl-benzenesulfonyl)-piperazin-1-yl]-benzofuran-2-carboxylic acid
4-Bromo-5-[4-(3-trifluoromethyl-benzenesulfonyl)-piperazin-1-yl]-benzofuran-2-carboxylic acid
4-Bromo-5-[4-(2,6-dichloro-benzenesulfonyl)-[1,4]diazepan-1-yl]-benzofuran-2-carboxylic acid
{4-Bromo-5-[4-(2,6-dichloro-benzenesulfonyl)-[1,4]diazepan-1-yl]-benzofuran-2-yl}-morpholin-4-yl-methanone
{4-Bromo-5-[4-(2,6-dichloro-benzenesulfonyl)-[1,4]diazepan-1-yl]-benzofuran-2-yl}-piperidin-1-yl-methanone
{5-[4-(3,5-Dichloro-2-hydroxy-benzenesulfonyl)-piperazin-1-yl]-4-methyl-benzofuran-2-yl}-morpholin-4-yl-methanone
{4-Bromo-5-[4-(2-fluoro-benzenesulfonyl)-piperazin-1-yl]-benzofuran-2-yl}-morpholin-4-yl-methanone
{4-Bromo-5-[4-(2-chloro-benzenesulfonyl)-piperazin-1-yl]-benzofuran-2-yl}-piperidin-1-yl-methanone
{4-Bromo-5-[4-(2,6-dichloro-benzenesulfonyl)-piperazin-1-yl]-benzofuran-2-yl}-piperidin-1-yl-methanone
{4-Bromo-5-[4-(2,6-dichloro-benzenesulfonyl)-piperazin-1-yl]-benzofuran-2-yl}-morpholin-4-yl-methanone
4-Bromo-5-[4-(2,6-dichloro-benzoyl)-[1,4]diazepan-1-yl]-benzofuran-2-carboxylic acid
5-[4-(3-Allyl-2-hydroxy-benzyl)-[1,4]diazepan-1-yl]-4-bromo-benzofuran-2-carboxylic acid
5-[4-(3,5-Dichloro-2-hydroxy-benzyl)-piperazin-1-yl]-4-methyl-benzofuran-2-carboxylic acid
4-Methyl-5-[4-(2,3,6-trichloro-benzyl)-piperazin-1-yl]-benzofuran-2-carboxylic acid
5-[4-(2,3-Dichloro-benzyl)-piperazin-1-yl]-4-methyl-benzofuran-2-carboxylic acid
4-Bromo-5-{4-[4-bromo-5-(4-fluoro-2-methoxy-phenyl)-3-methyl-pyrazol-1-yl]-piperidin-1-yl}-benzofuran-2-carboxylic acid
4-Bromo-5-{4-[5-(4-fluoro-2-methoxy-phenyl)-3-methyl-pyrazol-1-yl]-piperidin-1-yl}-benzofuran-2-carboxylic acid
4-Bromo-5-(4-{[(4-chloro-benzyl)-cyclopropylmethyl-amino]-methyl}-piperidin-1-yl)-benzofuran-2-carboxylic acid
{4-Bromo-5-[4-(2,6-dichloro-benzoyl)-[1,4]diazepan-1-yl]-benzofuran-2-yl}-morpholin-4-yl-methanone
4-Chloro-5-[4-(2,6-dichloro-benzoyl)-piperazin-1-yl]-benzofuran-2-carboxylic acid
4-Chloro-5-[1-(2,6-dichloro-benzenesulfonyl)-piperidin-4-ylamino]-benzofuran-2-carboxylic acid
{4-Chloro-5-[4-(2,3-dichloro-benzenesulfonyl)-piperazin-1-yl]-benzofuran-2-yl}-morpholin-4-yl-methanone
{4-Bromo-5-[4-(2,6-dichloro-benzenesulfonyl)-piperazin-1-yl]-benzofuran-2-yl}-(4-methyl-piperazin-1-yl)-methanone
4-Bromo-5-[4-(2,6-dichloro-benzenesulfonyl)-piperazin-1-yl]-benzofuran-2-carboxylic acid (2-dimethylamino-ethyl)-amide
4-Chloro-5-[4-(2-hydroxy-benzyl)-piperazin-1-yl]-benzofuran-2-carboxylic acid
{5-[4-(2,6-Dichloro-benzyl)-piperazin-1-yl]-4-methyl-benzofuran-2-yl}-morpholin-4-yl-methanone
4-Chloro-5-[4-(2,6-dichloro-benzenesulfonyl)-[1,4]diazepan-1-yl]benzofuran-2-carboxylic acid
5-[4-(2,3-Dichloro-benzenesulfonyl)-[1,4]diazepan-1-yl]-4-methyl-benzofuran-2-carboxylic acid
{5-[4-(2,3-Dichloro-benzenesulfonyl)-[1,4]diazepan-1-yl]-4-methyl-benzofuran-2-yl}-morpholin-4-yl-methanone
4-Chloro-5-[4-(2,3-dichloro-benzenesulfonyl)-[1,4]diazepan-1-yl]-benzofuran-2-carboxylic acid {4-Chloro-5-[4-(2,3-dichloro-benzenesulfonyl)-[1,4]diazepan-1-yl]-benzofuran-2-yl}-morpholin-4-yl-methanone
4-Chloro-5-[4-(2,5-dichloro-benzenesulfonyl)-[1,4]diazepan-1-yl]-benzofuran-2-carboxylic acid
{4-Chloro-5-[4-(2,5-dichloro-benzenesulfonyl)-[1,4]diazepan-1-yl]-benzofuran-2-yl}morpholin-4-yl-methanone
5-[4-(2,5-Dichloro-benzenesulfonyl)-[1,4]diazepan-1-yl]-4-methyl-benzofuran-2-carboxylic acid
{5-[4-(2,5-Dichloro-benzenesulfonyl)-[1,4]diazepan-1-yl]-4-methyl-benzofuran-2-yl}morpholin-4-yl-methanone
{4-Chloro-5-[4-(2,6-dichloro-benzenesulfonyl)-[1,4]diazepan-1-yl]-benzofuran-2-yl}-morpholin-4-yl-methanone
4-Chloro-5-[4-(2-chloro-6-hydroxy-benzyl)-piperazin-1-yl]-benzofuran-2-carboxylic acid
4-Chloro-5-[4-(2-chloro-6-methoxy-benzyl)-piperazin-1-yl]-benzofuran-2-carboxylic acid
4-Chloro-5-[4-(3-ethoxy-2-hydroxy-benzyl)-piperazin-1-yl]-benzofuran-2-carboxylic acid
4-Chloro-5-[4-(2-chloro-3-trifluoromethyl-benzyl)-piperazin-1-yl]-benzofuran-2-carboxylic acid
5-{4-[3-(2,6-Dichloro-phenyl)-5-isopropyl-isoxazol-4-ylmethyl]-piperazin-1-yl}-4-methyl-benzofuran-2-carboxylic acid
5-[4-(2,6-Dichloro-benzyl)-piperazin-1-yl]-4-methyl-benzofuran-2-carboxylic acid amide
5-[4-(2,6-Dichloro-benzyl)-[1,4]diazepan-1-yl]-4-methyl-benzofuran-2-carboxylic acid
{5-[4-(2,6-Dichloro-benzyl)-[1,4]diazepan-1-yl]-4-methyl-benzofuran-2-yl}-(4-methyl-piperazin-1-yl)-methanone
{4-Bromo-5-[4-(2,6-dichloro-benzoyl)-[1,4]diazepan-1-yl]-benzofuran-2-yl}-piperidin-1-yl-methanone
4-Bromo-5-[1-(2,6-dichloro-benzoyl)-piperidin-4-ylamino]-benzofuran-2-carboxylic acid
4-Bromo-5-[1-(2,3-dichloro-benzoyl)-piperidin-4-ylamino]-benzofuran-2-carboxylic acid
4-Chloro-5-[4-(2,3-dihydro-indol-1-yl)-piperidin-1-yl]-benzofuran-2-carboxylic acid
4-[2-(1Htetrazol-5-yl)-benzofuran-5-yl]-piperazine-1-carboxylic acid terbutyl ester
5-(4-Benzhydryl-piperazin-1-yl)-4-methyl-benzofuran-2-carboxylic acid
4-Bromo-5-[4-(2,6-dichloro-benzenesulfonylamino)-piperidin-1-yl]-benzofuran-2-carboxylic acid
4-Chloro-5-[4-(2-methyl-5-thiophen-2-yl-2H-pyrazol-3-ylmethyl)-piperazin-1-yl]-benzofuran-2-carboxylic acid
5-[1S,4S)-5-(2,6-Dichloro-benzenesulfonyl)-2,5-diaza-bicyclo[2.2.1]hept-2-yl]-4-methyl-benzofuran-2-carboxylic acid
5-[4-(2,4-Dichloro-phenylcarbamoyl)-piperidin-1-yl]-4-methyl-benzofuran-2-carboxylic acid.
Most preferred compounds are:
4-(4-Bromo-2-carboxy-benzofuran-5-yl)-piperazine-1-carboxylic acid tert-butyl ester
4-(2-Carboxy-benzofuran-5-ylamino)-piperidine-1-carboxylic acid tert-butyl ester
4-(2-Carboxy-4-chloro-benzofuran-5-yl)-piperazine-1-carboxylic acid tert-butyl ester
4-Bromo-5-[4-(pyridin-2-yloxy)-piperidin-1-yl]-benzofuran-2-carboxylic acid
4-Bromo-5-(4-pyridin-3-ylmethyl-piperazin-1-yl)-benzofuran-2-carboxylic acid
4-Chloro-5-(4-pyridin-3-ylmethyl-piperazin-1-yl)-benzofuran-2-carboxylic acid
4-Bromo-5-[4-(5-trifluoromethyl-pyridin-2-yloxy)-piperidin-1-yl]-benzofuran-2-carboxylic acid
4-(2-Carboxy-4-chloro-benzofuran-5-yl)-[1,4]diazepane-1-carboxylic acid tert-butyl ester
4-Chloro-5-[4-(5-trifluoromethyl-pyridin-2-yloxy)-piperidin-1-yl]-benzofuran-2-carboxylic acid
4-Bromo-5-[4-(2,6-dichloro-benzoyl)-piperazin-1-yl]-benzofuran-2-carboxylic acid
5-[4-(2,6-Dichloro-benzoyl)-piperazin-1-yl]-4-methyl-benzofuran-2-carboxylic acid
4-Bromo-5-[4-(4-trifluoromethyl-pyrimidin-2-yloxy)-piperidin-1-yl]-benzofuran-2-carboxylic acid
4-Bromo-5-[4-(2,6-dichloro-benzenesulfonyl)-piperazin-1-yl]-benzofuran-2-carboxylic acid
5-[4-(2,6-Dichloro-benzenesulfonyl)-piperazin-1-yl]-4-methyl-benzofuran-2-carboxylic acid
4-Chloro-5-[4-(2,6-dichloro-benzenesulfonyl)-piperazin-1-yl]-benzofuran-2-carboxylic acid
4-Chloro-5-[4-(2,3-dichloro-benzenesulfonyl)-piperazin-1-yl]-benzofuran-2-carboxylic acid
5-[4-(2-Chloro-6-fluoro-benzyl)-piperazin-1-yl]-4-methyl-benzofuran-2-carboxylic acid
5-[4-(2,6-Dichloro-benzyl)-piperazin-1-yl]-4-methyl-benzofuran-2-carboxylic acid
4-Methyl-5-[4-(5-trifluoromethyl-pyridin-2-yloxy)-piperidin-1-yl]-benzofuran-2-carboxylic acid
4-Bromo-5-[4-(2,6-dichloro-benzenesulfonyl)-[1,4]diazepan-1-yl]-benzofuran-2-carboxylic acid
{4-Bromo-5-[4-(2,6-dichloro-benzenesulfonyl)-[1,4]diazepan-1-yl]-benzofuran-2-yl}-morpholin-4-yl-methanone
{5-[4-(3,5-Dichloro-2-hydroxy-benzenesulfonyl)-piperazin-1-yl]-4-methyl-benzofuran-2-yl}-morpholin-4-yl-methanone
{4-Bromo-5-[4-(2,6-dichloro-benzenesulfonyl)-piperazin-1-yl]-benzofuran-2-yl}-piperidin-1-yl-methanone
{4-Bromo-5-[4-(2,6-dichloro-benzenesulfonyl)-piperazin-1-yl]-benzofuran-2-yl}-morpholin-4-yl-methanone
4-Bromo-5-{4-[5-(4-fluoro-2-methoxy-phenyl)-3-methyl-pyrazol-1-yl]-piperidin-1-yl}-benzofuran-2-carboxylic acid
4-Chloro-5-[1-(2,6-dichloro-benzenesulfonyl)-piperidin-4-ylamino]-benzofuran-2-carboxylic acid
{4-Bromo-5-[4-(2,6-dichloro-benzenesulfonyl)-piperazin-1-yl]-benzofuran-2-yl}-(4-methyl-piperazin-1-yl)-methanone
4-Bromo-5-[4-(2,6-dichloro-benzenesulfonyl)-piperazin-1-yl]-benzofuran-2-carboxylic acid (2-dimethylamino-ethyl)-amide
{5-[4-(2,6-Dichloro-benzyl)-piperazin-1-yl]-4-methyl-benzofuran-2-yl}-morpholin-4-yl-methanone
4-Chloro-5-[4-(2,6-dichloro-benzenesulfonyl)-[1,4]diazepan-1-yl]-benzofuran-2-carboxylic acid
5-[4-(2,3-Dichloro-benzenesulfonyl)-[1,4]diazepan-1-yl]-4-methyl-benzofuran-2-carboxylic acid
4-Chloro-5-[4-(2,3-dichloro-benzenesulfonyl)-[1,4]-diazepan-1-yl]-benzofuran-2-carboxylic acid
5-{4-[3-(2,6-Dichloro-phenyl)-5-isopropyl-isoxazol-4-ylmethyl]-piperazin-1-yl}-4-methyl-benzofuran-2-carboxylic acid
5-[4-(2,6-Dichloro-benzyl)-piperazin-1-yl]-4-methyl-benzofuran-2-carboxylic acid amide
5-[4-(2,6-Dichloro-benzyl)-[1,4]diazepan-1-yl]-4-methyl-benzofuran-2-carboxylic acid
{5-[4-(2,6-Dichloro-benzyl)-[1,4]diazepan-1-yl]-4-methyl-benzofuran-2-yl}-(4-methyl-piperazin-1-yl)-methanone
4-Bromo-5-[(1-(2,6-dichloro-benzoyl)-piperidin-4-ylamino]-benzofuran-2-carboxylic acid
4-Chloro-5-[4-(2,3-dihydro-indol-1-yl)-piperidin-1-yl]-benzofuran-2-carboxylic acid.

According to a second object, the present invention provides a pharmaceutical composition comprising the compounds of formula (I) wherein the compositions comprise one or more pharmaceutically acceptable excipients and a therapeutically effective amount of at least one of the compounds of the present invention, or a pharmaceutically acceptable salt or ester form thereof.

In a particular embodiment, the present invention provides a pharmaceutical composition, further containing one or more additional compounds, selected from the group consisting of physiologically acceptable excipients, auxiliaries, adjuvants, diluents, carriers and pharmaceutically active agents other than the compounds according to the invention.

In a particular embodiment, the present invention provides a set (kit) comprising separate packets consisting of:
 a) a therapeutically effective amount of one or more compounds according to the invention and,
 b) a therapeutically effective amount one or more further pharmaceutically active agents other than the compounds according to the invention.

Compounds of structural formula I may be used in combination with one or more other drugs in the treatment, prevention, suppression or amelioration of diseases or conditions for which compounds of structural formula I or the other drugs have utility. Typically the combination of the drugs is safer or more effective than either drug alone, or the combination is safer or more effective than would it be expected based on the additive properties of the individual drugs. Such other drug(s) may be administered, by a route and in an amount commonly used contemporaneously or sequentially with a compound of structural formula I. When a compound of structural formula I is used contemporaneously with one or more other drugs, a combination product containing such other drug(s) and the compound of structural formula I is preferred. However, combination therapy also includes therapies in which the compound of structural formula I and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of structural formula I.

Examples of other active ingredients that may be administered in combination with a compound of structural formula I, and either administered separately or in the same pharmaceutical composition, include, but are not limited to: dipeptidyl peptidase IV (DP-IV) inhibitors; insulin sensitizing agents including PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as gemfibrozil, clofibrate, fenofibrate and bezafibrate, and biguanides, such as metformin and phenformin; insulin or insulin mimetics; sulfonylureas and other insulin secretagogues such as tolbutamide, glipizide, meglitinide and related materials; α-glucosidase inhibitors, such as acarbose; glucagon receptor antagonists such as those disclosed in WO 98/04528, WO 99/01423, WO 00/39088 and WO 00/69810; GLP-1, GLP-1 analogs, and GLP-1 receptor agonists such as those disclosed in WOOO/42026 and WOOO/59887; GIP, GIP mimetics such as those disclosed in WOOO/58360, and GIP receptor agonists; PACAP, PACAP mimetics, and PACAP receptor 3 agonists such as those disclosed in WO 01/23420; cholesterol lowering agents such as HMG-CoA reductase inhibitors (lovastatin, simvastatin, pravastatin, cerivastatin, fluvastatin, atorvastatin, itavastatin, rosuvastatin, and other stating), bile-acid sequestrants (cholestyramine, colestipol, and dialkylaminoalkyl derivatives of a cross-linked dextran), nicotinyl alcohol, nicotinic acid or a salt thereof, inhibitors of cholesterol absorption, such as ezetimibe and beta-sitosterol, acyl CoA:cholesterol acyltransferase inhibitors, such as, for example, avasimibe, and anti-oxidants, such as probucol; PPARδ agonists, such as those disclosed in WO97/28149; antiobesity compounds such as fenfluramine, dexteniuramine, phentermine, sibutramine, orlistat, neuropeptide Y1 or Y5 antagonists, CB 1 receptor inverse agonists and antagonists, adrenergic receptor agonists, melanocortin-receptor agonists, in particular melanocortin-4 receptor agonists, ghrelin antagonists, and melanin-concentrating hormone (MCH) receptor antagonists; ileal bile acid transporter inhibitors; agents intended for use in inflammatory conditions other than glucocorticoids, such as aspirin, non-steroidal anti-inflammatory drugs, azulfidine, and selective cyclooxygenase-2 inhibitors; protein tyrosine phosphatase 1B (PTP-1B) inhibitors; antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telnisartan, and valsartan; and inhibitors of cholesteryl ester transfer protein (CETP). The above combinations include a compound of structural formula I, or a pharmaceutically acceptable salt or solvate thereof, with one or more other active compounds. Non limiting examples include combinations of compounds of structural formula I with two or more active compounds selected from biguanides, sulfonylureas, HMG-CoA reductase inhibitors, PPAR agonists, PTP-1B inhibitors, DP-IV inhibitors, and anti-obesity compounds.

A further embodiment of the present invention is a process for the manufacture of said pharmaceutical compositions, characterized in that one or more compounds according to the invention and one or more compounds selected from the group consisting of solid, liquid or semiliquid excipients, auxiliaries, adjuvants, diluents, carriers and pharmaceutically active agents other than the compounds according to the invention, are converted in a suitable dosage form.

The pharmaceutical compositions of the present invention may be administered by any means that achieve their intended purpose. For example, administration may be by oral, parenteral, topical, enteral, intravenous, intramuscular, inhalant, nasal, intraarticular, intraspinal, transtracheal, intraocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

Tablets: mixing of active ingredient's and auxiliaries, compression of said mixture into tablets (direct compression), optionally granulation of part of mixture before compression.

Capsules: mixing of active ingredient/s and auxiliaries to obtain a flowable powder, optionally granulating powder, filling powders/granulate into opened capsules, capping of capsules.

Semi-solids (ointments, gels, creams): dissolving/dispersing active ingredient's in an aqueous or fatty carrier; subsequent mixing of aqueous/fatty phase with complementary fatty/aqueous phase, homogenization (creams only).

Suppositories (rectal and vaginal): dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

Aerosols: dispersing/dissolving active agent's in a propellant, bottling said mixture into an atomizer.

In general, non-chemical routes for the production of pharmaceutical compositions and/or pharmaceutical preparations comprise processing steps on suitable mechanical means known in the art that transfer one or more compounds according to the invention into a dosage form suitable for administration to a patient in need of such a treatment. Usually, the transfer of one or more compounds according to the invention into such a dosage form comprises the addition of one or more compounds, selected from the group consisting of carriers, excipients, auxiliaries and pharmaceutical active ingredients other than the compounds according to the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, 5th Edition. In this respect, active ingredients are preferably at least one compound according to this invention and one or more additional compounds other than the compounds according to the invention, which show valuable pharmaceutical properties, preferably those pharmaceutical active agents other than the compounds according to the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The novel compounds may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropyl-methylcellulose, sodium carboxymethylcellulose, polyvinyl pyrrolidone and/or Vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component me latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropymethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The novel compounds can also be lyophilized and the lyophilizates obtained can be used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colorants, flavourings and/or aromatizers. They can, if desired, also contain one or more further active compounds, e.g. one or more vitamins.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the compounds of the present invention will be in the form of pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The present invention includes within its scope prodrugs of the compounds of the present invention above. In general, such prodrugs will be functional derivatives of the compounds of the present invention, which are readily convertible in vivo into the required compound of the present invention. Conventional procedures for the selection and preparation of suitable prodrug derivatives are described, for example, in Design of Prodrugs, ed. H Bundgaard, Elsevier, 1985.

The pharmaceutical preparations can be employed as medicaments in human and veterinary medicine. As used herein, the term "effective amount" amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the compounds according to the invention is known to the skilled artisan or can be easily determined by standard methods known in the art.

The substances according to the invention are generally administered analogously to commercial preparations. Usually, suitable doses that are therapeutically effective lie in the range between 0.0005 mg and 1000 mg, preferably between 0.005 mg and 500 mg and especially between 0.5 and 100 mg per dose unit. The daily dose is preferably between about 0.001 and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The host, or patient, may be from any mammalian species, e.g., primate sp., particularly human; rodents, including mice, rats and hamsters; rabbits; equines, bovines, canines, felines, etc. Animal models are of interest for experimental investigations, providing a model for treatment of human disease.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

In the case of many disorders, the susceptibility of a particular cell to treatment with the subject compounds may be determined by in vitro testing. Typically a culture of the cell is combined with a subject compound at varying concentrations for a period of time sufficient to allow the active agents to show a relevant reaction, usually between about one hour and one week. For in vitro testing, cultured cells from a biopsy sample may be used.

According to a third object, the present invention provides for the use of compounds of formula (I) or pharmaceutically acceptable salts thereof for the manufacture of a medicament for the treatment, prevention, or amelioration of one or more symptoms of diseases or disorders that are modulated or otherwise affected by farnesoid X receptor activity or in which the farnesoid X receptor is implicated.

In one embodiment, the compounds provided herein are agonists of the farnesoid X receptor. In another embodiment, the compounds provided herein are antagonists of the farnesoid X receptor. In another embodiment, the compounds provided herein are inverse agonists, partial agonists or partial antagonists of the farnesoid X receptor. Agonists that exhibit low efficacy are, in certain embodiments, antagonists.

According to a fourth object, the present invention provides a method for treatment, prevention, inhibition or amelioration of one or more symptoms of diseases or disorders mediated or in which farnesoid X receptor is implicated, comprising administering to a subject in need thereof an effective amount of a compound of formula (I) or a pharmaceutically acceptable salt thereof.

In a preferred aspect, the present invention provides methods for treatment, prevention, inhibition or amelioration of one or more symptoms of diseases or disorders selected from hypercholesterolemia, hyperlipoproteinemia, hypertriglyceridemia, dyslipidemia, lipodystrophy, cholestasis/fibrosis, cholesterol gallstone disease, gastrointestinal disease or condition, hyperglycemia, diabetes mellitus, type 2 diabetes, insulin resistance, metabolic inflexibility, nephropathy, liver diseases, atherosclerosis, cancer, inflammatory disorders, obesity, osteoporosis, skin aging, hair growth regulation and pigmentation disorders, Parkinson's disease and/or Alzheimer's disease.

In another aspect of the invention, the invention provides a method of reducing the risk of developing a condition selected from the group consisting of hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, pancreatitis, abdominal obesity, neurodegenerative disease, retinopathy, nephropathy, neuropathy, Metabolic Syndrome, hypertension and other conditions and disorders where insulin resistance is a component in a mammalian patient in need of such treatment, said method comprising administering to the patient a compound in accordance with structural formula I in an amount that is effective to reduce the risk of developing said condition.

In another aspect of the invention, the invention provides a method of treating a condition selected from the group consisting of hyperglycemia, low glucose tolerance, insulin resistance, obesity, lipid disorders, dyslipidemia, hyperlipidemia, hypertrigly-ceridemia, hypercholesterolemia, low HDL levels, high LDL levels, atherosclerosis and its sequelae, vascular restenosis, pancreatitis, abdominal obesity, neurodegenerative disease, retinopathy, nephropathy, neuropathy, Metabolic Syndrome, hypertension and other conditions and disorders where insulin resistance is a component, in a mammalian patient in need of such treatment, said method comprising administering to the patient an effective amount of a compound as defined in structural, formula I and a compound selected from the group consisting of: dipeptidyl peptidase-IV (DP-IV); inhibitors; insulin sensitizing agents selected from the group consisting of PPARγ agonists, PPARα agonists, PPARα/γ dual agonists, and biguanides; insulin and insulin mimetics; sulfonylureas and other insulin secretagogues; α-glucosidase inhibitors; glucagon receptor antagonists; GLP-1, GLP-1 analogs, and GLP-1 receptor agonists; GIP, GIP mimetics, and GIP receptor agonists; PACAP, PACAP mimetics, and PACAP receptor 3 agonists; cholesterol lowering agents selected from the group consisting of HMG-CoA reductase inhibitors, sequestrants, nicotinyl alcohol, nicotinic acid and salts thereof, inhibitors of cholesterol absorption, acyl CoA:cholesterol acyltransferase inhibitors, and anti-oxidants; PPARδ agonists; antiobesity compounds; ileal bile acid transporter inhibitors; anti-inflammatory agents, excluding glucocorticoids; protein tyrosine phosphatase 1B (PTP-1B) inhibitors; and antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; said compounds being administered to the patient in an amount that is effective to treat said condition. Dipeptidyl peptidase-IV inhibitors that can be combined with compounds of structural formula I include those disclosed in WO 03/004498, WO 03/004496; EP 1 258 476; WO 02/083128; WO 02/062764; WO 03/00025; WO 03/002530; WO 03/002531; WO 03/002553; WO 03/002593; WO 03/000180; and WO 03/000181. Specific DP-IV inhibitor compounds include isoleucine thiazolidide; NVP-DPP728; P32/98; and LAF 237.

Antiobesity compounds that can be combined with compounds of structural formula I include fenfluramine, dexfenfluramine, phentermine, sibutramine, orlistat, neuropeptide Y1 or Y5 antagonists, cannabinoid CB 1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," Expert Opin. Ther. Patents, 11: 1677-1692 (2001) and D. Spanswick and K. Lee, "Emerging antiobesity drugs," Expert Opin. Emerging Drugs, 8: 217-237 (2003).

Neuropeptide Y5 antagonists that can be combined with compounds of structural formula I include those disclosed in U.S. Pat. No. 6,335,345 and WO 01/14376; and specific compounds identified as GW59884A; GW569180A; LY366377; and COP-71683A.

Cannabinoid CB 1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; and U.S. Pat. No. 5,292,736.

Melanocortin receptor agonists that can be combined with compounds of formula I include those disclosed in WO 03/009847; WO 02/068388; WO 99/64002; WO 00/74679; WO 01/70708; and WO 01/70337 as well as those disclosed in J. D. Speake et al., "Recent advances in the development of melanocortin-4 receptor agonists, Expert Opin. Ther. Patents, 12: 1631-1638 (2002).

In another aspect of the invention, the invention provides a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment, said method comprising administering to the patient a therapeutically effective amount of a compound as defined in structural formula I and an HMG-CoA reductase inhibitor.

More particularly, in another aspect of the invention, the invention provides a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment as defined above, wherein the HMG-CoA reductase inhibitor is a statin.

Even more particularly, in another aspect of the invention, the invention provides a method of treating a condition selected from the group consisting of hypercholesterolemia, atherosclerosis, low HAL levels, high LDL levels, hyperlipidemia, hypertriglyceridemia and dyslipidemia, in a mammalian patient in need of such treatment as defined above, wherein the HMG-CoA reductase inhibitor is a statin selected from the group consisting of lovastatin, simvastatin, pravastatin, cerivastatin, fluvastatin, atorvastatin, itavastatin and rosuvastatin.

In another aspect of the invention, the invention provides a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions, said method comprising administering to a mammalian patient in need of such treatment a therapeutically effective amount of a compound as defined in structural formula I and an HMG-CoA reductase inhibitor.

In another aspect of the invention, the invention provides a method for delaying the onset or reducing the risk of developing atherosclerosis in a human patient in need of such treatment, said method comprising administering to said patient an effective amount of a compound as defined in structural formula I and an HMG-CoA reductase inhibitor.

More particularly, the invention provides a method for delaying the onset or reducing the risk of developing atherosclerosis in a human patient in need of such treatment as defined above, wherein the HMG-CoA reductase inhibitor is a statin.

Even more particularly, the invention provides a method for delaying the onset or reducing the risk of I developing atherosclerosis in a human patient in need of such treatment as defined above, wherein the HMG-CoA reductase inhibitor is a statin selected from the group consisting of: lovastatin, simvastatin, pravastatin, cerivastatin, fluvastatin, atorvastatin, itavastatin, and rosuvastatin.

Even more particularly, the invention provides a method for delaying the onset or reducing the risk of developing atherosclerosis in a human patient in need of such treatment as defined above, wherein the statin is simvastatin.

In another aspect of the invention, the invention provides a method for delaying the onset or reducing the risk of developing atherosclerosis in a human patient in need of such treatment as defined above, wherein the HMG-CoA reductase inhibitor is a statin and further comprising administering a cholesterol absorption inhibitor.

More particularly, in another aspect of the invention, the invention provides a method for delaying the onset or reducing the risk of developing atherosclerosis in a human patient in need of such treatment as defined above, wherein the HMG-CoA reductase inhibitor is a statin and the cholesterol absorption inhibitor is ezetimibe.

In another aspect of the invention, a pharmaceutical composition is disclosed which comprises a compound according to structural formula I, a compound selected from the group consisting of: DP-IV inhibitors; insulin I sensitizing agents selected from the group consisting of PPARα agonists; PPARγ agonists, PPARα/γ dual agonists, and biguanides; insulin and insulin mimetics; sulfonylureas and other insulin secretagogues; oc-glucosidase inhibitors; glucagon receptor antagonists; GLP-1, GLP-1 analogs, and GLP-1 receptor agonists; GIP, GIP mimetics, and GIP receptor agonists; PACAP, PACAP mimetics, and PACAP receptor 3 agonists; cholesterol lowering agents selected from the group consisting of HMG-CoA reductase inhibitors, sequestrants, (nicotinyl alcohol, nicotinic acid or a salt thereof, inhibitors of cholesterol absorption, acyl CoA:cholesterol acyltransferase inhibitors, and anti-oxidants; PPARδ agonists; antiobesity compounds; ileal bile acid transporter inhibitors; anti-inflammatory agents other than glucocorticoids; protein tyrosine phosphatase 1B (PTP-1B) inhibitors; and antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; inhibitors of cholesteryl ester transfer protein (CETP); and a pharmaceutically acceptable carrier.

These and other objects, features and advantages of the compounds of formula (I) will be disclosed in the following detailed description of the patent disclosure.

DEFINITIONS

The following terms and expressions contained herein are defined as follows:

As used herein, the term "alkyl" refers to a aliphatic hydrocarbon group which may be straight, or branched having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms.

As used herein, the term "alkenyl" refers to a straight chain, or branched hydrocarbon chains of 2 to 8 carbon atoms having at least one carbon-carbon double bond. A designation "$C_2$-$C_8$ alkenyl" refers to an alkenyl radical containing from 2 to 8 carbon atoms. Examples of alkenyl groups include ethenyl, propenyl, isopropenyl, 2,4-pentadienyl, etc.

As used herein, the term "alkynyl" means an aliphatic hydrocarbon group containing a carbon-carbon triple bond and which may be straight or branched having 2 to 8 carbon atoms in the chain. Branched means that one or more lower alkyl groups such as methyl, ethyl or propyl are attached to a linear alkynyl chain. Exemplary alkynyl groups include ethynyl, propynyl, n-butynyl, 2-butynyl, 3-methylbutynyl, n-pentynyl, heptynyl, octynyl.

As used herein, the term "alkylene" means a straight or branched bivalent hydrocarbon chain having from 1 to 8 carbon atoms. The preferred alkylene groups are the lower alkylene groups having from 1 to about 4 carbon atoms. Exemplary groups include methylene (—$CH_2$—), and ethylene (—$CH_2CH_2$—).

As used herein, the term "alkoxy" means an alkyl-O— group wherein the alkyl group is as herein described. Exemplary alkoxy groups include methoxy, ethoxy, n-propoxy, i-propoxy, n-butoxy and heptoxy.

As used herein, the term "alkylenoxy" means an alkylene-O— group, wherein the alkylene group is as herein defined.

As used herein, the terms "halogen atom" or "halogen" refers to fluorine, chlorine, bromine or iodine atom, preferably bromine, fluorine and chlorine atom.

As used herein, the term "halogenoalkyl" refers to an alkyl group substituted by one or more halogen atoms, wherein said alkyl group and halogen atoms are as defined above. Halogenoalkyl groups include notably perhalogenoalkyl groups, such as perfluoralkyl groups of formula $C_nF_{2n+1}$-. Examples of halogenalkyl groups include trifluoromethyl ($CF_3$).

As used herein, the term "halogenoalkoxy" refers to an alkyl group substituted by one or more halogen atoms, wherein said alkoxy group and halogen atoms are as defined above.

As used herein, the terms "carbocycle", "carbocyclic" or "carbocyclyl" refer to a substituted or unsubstituted, stable monocyclic or bicyclic hydrocarbon ring system which is saturated, partially saturated or unsaturated, and contains from 3 to 10 ring carbon atoms. Accordingly the carbocyclic group may be aromatic or non-aromatic, and includes the cycloalkyl and aryl compounds defined herein. The bonds connecting the endocyclic carbon atoms of a carbocyclic group may be single, double, triple, or part of a fused aromatic moiety.

As used herein, the term "cycloalkyl" refers to a saturated or partially saturated mono- or bicyclic alkyl ring system containing 3 to 10 carbon atoms, A designation such as "$C_5$-$C_7$ cycloalkyl" refers to a cycloalkyl radical containing from 5 to 7 ring carbon atoms. Preferred cycloalkyl groups include those containing 5 or 6 ring carbon atoms. Examples of cycloalkyl groups include such groups as cyclopropyl, cyclobutyl, cyclopentyl, cyclohexyl, cycloheptyl, cyclooctyl, pinenyl, and adamantanyl.

As used herein, the term "cycloalkoxy" means a cycloalkyl-O— group wherein the cycloalkyl group is as herein described.

As used herein, the term "cycloalkylalkyl" means a cycloalkyl-alkyl-group wherein the cycloalkyl and alkyl groups are as herein described.

As used herein, the term "aryl" refers to a substituted or unsubstituted, mono- or bicyclic hydrocarbon aromatic ring system having 6 to 10 ring carbon atoms. Examples include phenyl and naphthyl. Preferred aryl groups include unsubstituted or substituted phenyl and naphthyl groups. Included within the definition of "aryl" are fused ring systems, including, for example, ring systems in which an aromatic ring is fused to a cycloalkyl ring. Examples of such fused ring systems include, for example, indene, indene, and tetrahydronaphthalene.

As used herein, the term "aryloxy" means an aryl-O— group wherein the aryl group is as herein described. Exemplary aryloxy groups include the phenyloxy group.

As used herein, the terms "heterocycle", "heterocyclic" or "heterocyclyl" refer to a substituted or unsubstituted carbocyclic group in which the ring portion includes at least one heteroatom such as O, N, or S. The nitrogen and sulfur heteroatoms may be optionally oxidized, and the nitrogen may be optionally substituted in non-aromatic rings. Heterocycles are intended to include heteroaryl and heterocycloalkyl groups.

As used herein, the term "heteroaryl" refers to an aromatic group containing 5 to 10 ring carbon atoms in which one or more ring carbon atoms are replaced by at least one hetero atom such as —O—, —N—, or —S—. Examples of heteroaryl groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, the term "heterocycloalkyl" means a non-aromatic saturated monocyclic, bi- or multicyclic ring system containing 3 to 14 carbon atoms, preferably 5 to 10 carbon atoms, in which one or more of the carbon atoms in the ring system is/are hetero element(s) other than carbon, for example nitrogen, oxygen or sulfur. Preferred ring sizes of rings of the ring system include 5 to 6 ring atoms. The heterocycloalkyl may be optionally substituted. The nitrogen or sulphur atom of the heterocycloalkyl may also be optionally oxidized to the corresponding N-oxide, S-oxide or S,S-dioxide. Exemplary monocyclic heterocycloalkyl rings include piperidyl, pyrrolidinyl, piperazinyl, morpholinyl, imidazolidinyl, pyrazolidinyl, thiomorpholinyl, thiazolidinyl, 1,3-dioxolanyl, 1,4-dioxanyl, tetrahydrofuranyl, tetrahydrothiophenyl, tetrahydrothiopyranyl.

As used herein, the term "arylalkyl" or "aralkyl" refers to an alkyl group that is substituted with an aryl group. Examples of arylalkyl groups include, but are not limited to, benzyl, phenethyl, benzhydryl, diphenylmethyl, triphenylmethyl, diphenylethyl, naphthylmethyl, etc.

As used herein, the terms "alkyl", "aryl", "heteroaryl", and the likes refers also to the corresponding "alkylene", "arylene", "heteroarylene", and the likes which are formed by the removal of two hydrogen atoms.

As used herein the term "dialkylaminoalkyl" means a $(Alk_1)(Alk_2)$N-alkyl—wherein $Alk_1$ and $Alk_2$ denote an alkyl group, said alkyl group being as defined herein.

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

All other terms used in the description of the present invention have their meanings as is well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methyl amine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well-known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J., et al. *Enantiomers, Racemates, and Resolutions*; Wiley: New York, 1981, each incorporated by reference herein in their entireties.

SYNTHESIS

The compounds of the present invention may be prepared in a number of methods well known to those skilled in the art, including, but not limited to those described below, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from active starting materials or by deliberate chiral synthesis of target centers.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

The process of preparation of a compound of formula (I) of the invention is another object of the present invention.

According to a first aspect, compounds of the invention of formula (I) can be prepared according to a method comprising the reaction of compounds of formula (II):

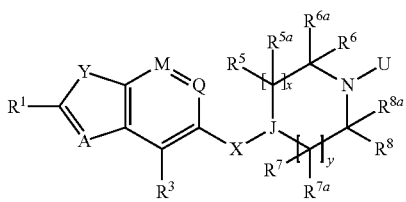

(I)

wherein $R^1$, Y, A, M, Q, $R^3$, X, J, $R^5$, $R^{5a}$, $R^6$, $R^{6a}$, $R^7$, $R^{7a}$, $R^8$, $R^{8a}$, x, and y are as defined in formula (I), and U is H or an amine protecting group.

"Amine protecting group" means an easily removable group which is known in the art to protect an amino group against undesirable reaction during synthetic procedures and to be selectively removable. The use of amine protecting groups is well known in the art for protecting groups against undesirable reactions during a synthetic procedure and many such protecting groups are known, for example, T. H. Greene and P. G. M. Wuts, Protective Groups in Organic Synthesis, 2nd edition, John Wiley & Sons, New York (1991). Preferred amine protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxycarbonyl, 9-fluorenylmethoxycarbonyl, 2,2,2-trifluoro-ethoxycarbonyl, 2-trimethylsilylethxoycarbonyl, vinyloxycarbonyl, allyloxy-carbonyl, t-butyloxycarbonyl (Boc), 1,1-dimethylpropynyloxycarbonyl, benzyloxy-carbonyl (CBz), p-nitrobenzyloxycarbony, 2,4-dichlorobenzyloxycarbonyl, and the like.

Generally, a deprotection, substitution or functionalization reaction of U into the desired R function is carried out.

More precisely, when R represents a group $VR^4$ as defined above, the compound of formula (I) can be obtained by reacting a compound of formula (II) in which U is H, with $R^4V$-Hal wherein Hal is an halogen atom in the presence of a suitable base, notably an alkaline or alkaline earth metal hydroxide such as LiOH.

According to a first embodiment, the compound of formula (II) may be prepared according to a method comprising the reaction of a compound of formula (III) with a compound of formula (IV):

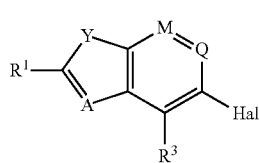

(III)

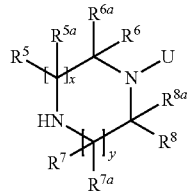

(IV)

wherein $R^1$, Y, A, M, Q, $R^3$, X, J, $R^5$, $R^{5a}$, $R^6$, $R^{6a}$, $R^7$, $R^{7a}$, $R^8$, $R^{8a}$, x, y and U are as defined in formula (II), and Hal is an halogen atom.

Generally, an aromatic substitution of the Hal group of compound of formula (III) by a compound of formula (IV) is carried out, notably in the presence of a palladium catalyst, such as in the presence of $Pd(OAc)_2$ and BINAP.

In a particular aspect, the compound of formula (III) may be prepared according to a method comprising the reaction of a compound of formula (V):

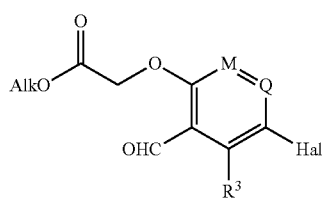

(V)

wherein M, Q, $R^3$, Hal are as defined in formula (III), and Alk is a $C_1$-$C_6$ alkyl group.

Generally, the cyclisation of the compound of formula (III) is carried out in the presence of a suitable base such as a metal alkoxide, such as sodium methanolate.

In a particular aspect, the compound of formula (V) is prepared according to a method comprising the reaction of a compound of formula (VI):

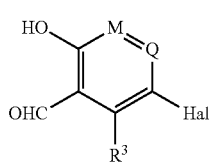

(VI)

wherein M, Q, $R^3$, and Hal are as defined in formula (V).

Generally, the compound of formula (V) is prepared by reacting a compound of formula (III) with a compound Hal-$CH_2$—$CO_2$Alk wherein Hal is an halogen atom and Alk is a $C_1$-$C_6$ alkyl in the presence of a suitable base such as a metal hydride such as sodium hydride.

According to a second embodiment, the compound of formula (II) is prepared according to a method comprising the reaction of a compound of formula (VII):

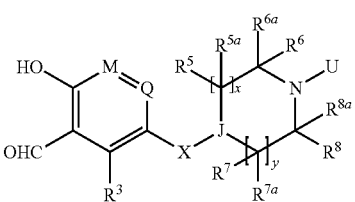

(VII)

wherein M, Q, $R^3$, X, J, $R^5$, $R^{5a}$, $R^6$, $R^{6a}$, $R^7$, $R^{7a}$, $R^8$, $R^{8a}$, x, y and U are as defined in formula (II).

Generally, the compound of formula (II) is prepared by reacting a compound of formula (VII) with a compound Hal-$CH_2$—$CO_2$Alk wherein Hal is an halogen atom and Alk is a $C_1$-$C_6$ alkyl group in the presence of a suitable base such as an alkaline metal carbonate, such as potassium carbonate.

In a particular aspect, the compound of formula (VII) is prepared according to a method comprising reacting a compound of formula (VIII) with a compound of formula (IX):

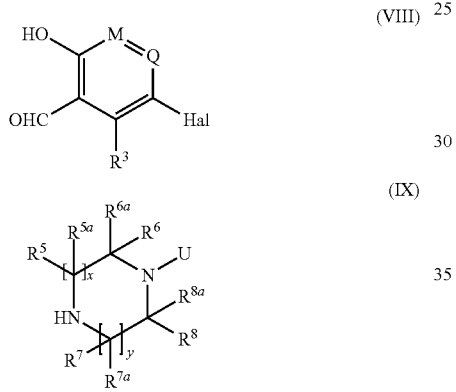

(VIII)

(IX)

wherein M, Q, $R^3$, Hal, $R^5$, $R^{5a}$, $R^6$, $R^{6a}$, $R^7$, $R^{7a}$, $R^8R^{8a}$, U, x and y are as defined in formula (VII).

Generally, the compound of formula (VII) is prepared by coupling a compound of formula (VIII) with a compound of formula (IX) in the presence of a palladium catalyst, such as in the presence of $Pd(OAc)_2$ and $tBu_3P$.

Further, the process of the invention may also comprise the additional step of isolating the compound of formula (I). This can be done by the skilled person by any of the known conventional means, such as the recovery methods described above.

The starting products are commercially available or may be obtained by applying or adapting any known methods or those described in the examples.

Representative schemes of the processes of the invention are summarized below: all substituents in the synthetic Schemes, unless otherwise indicated, are as previously defined.

Scheme 1

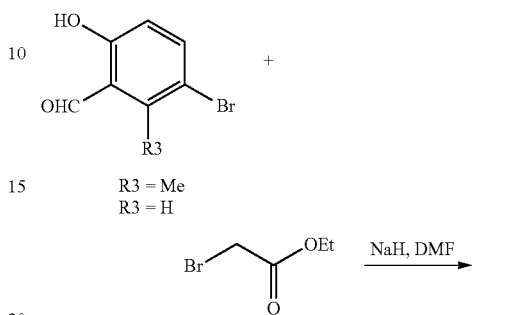

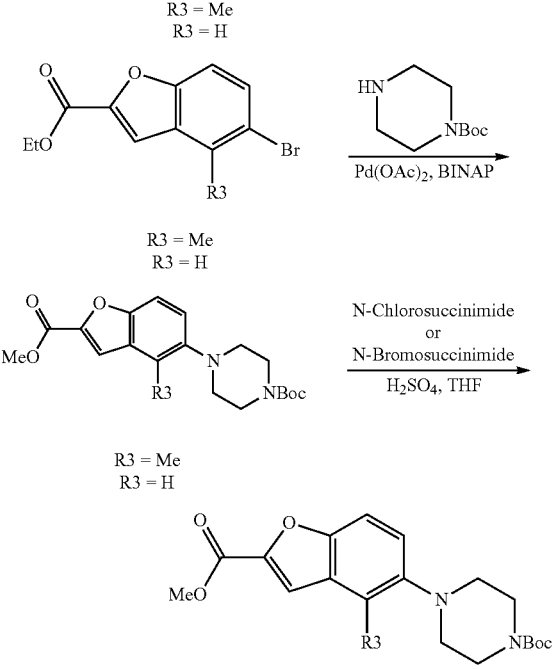

Scheme 2

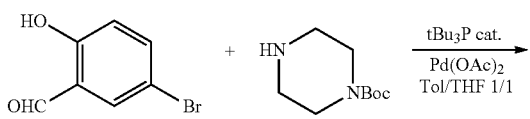

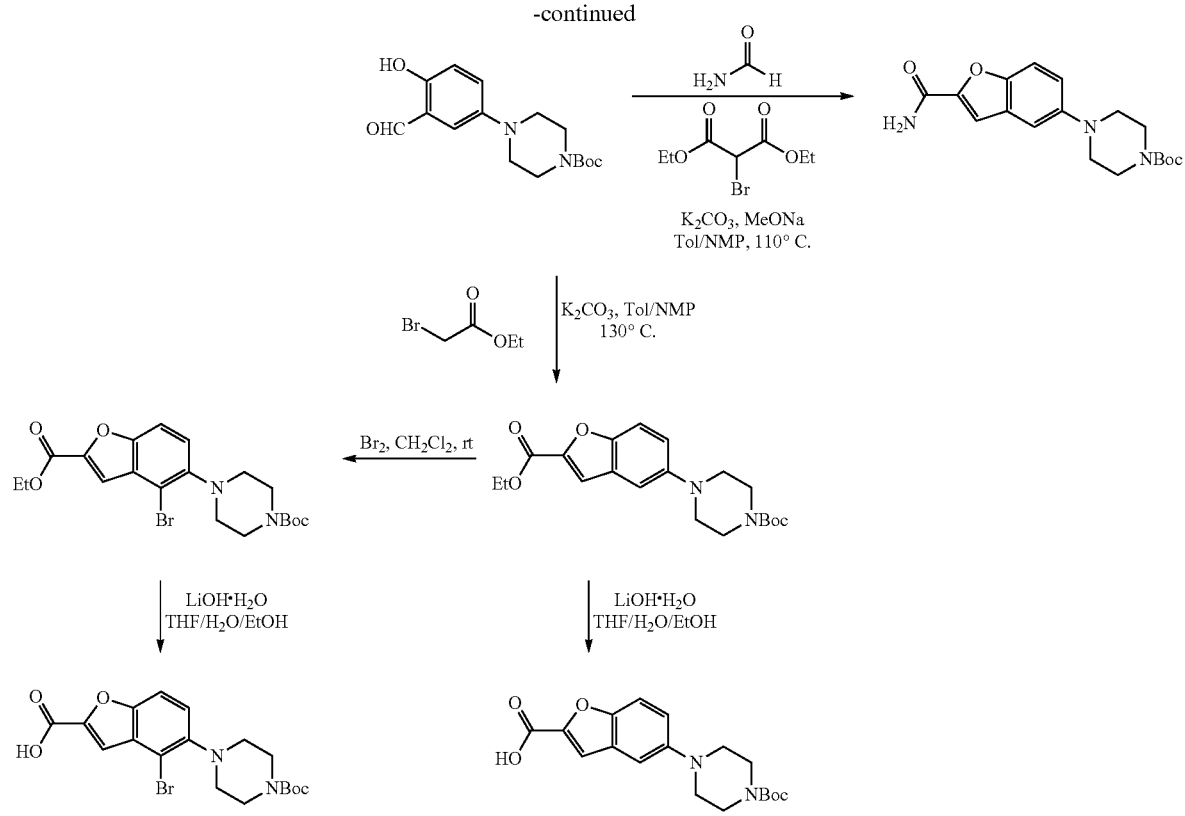
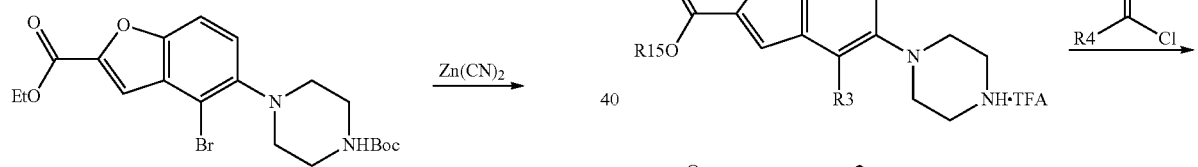
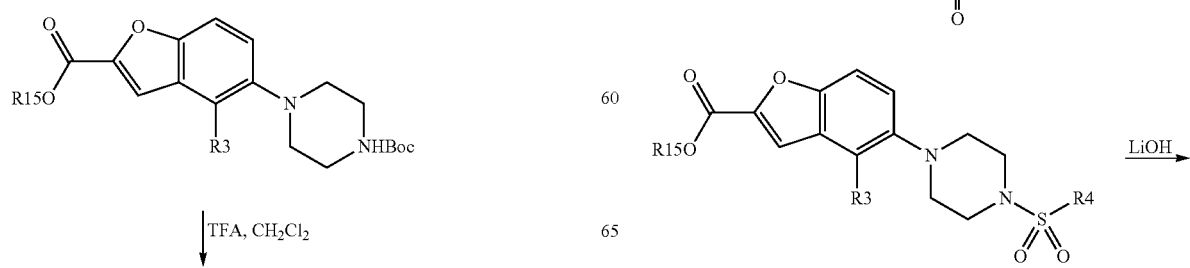

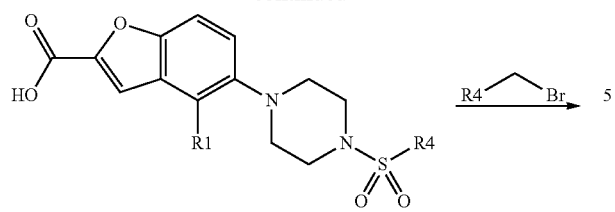

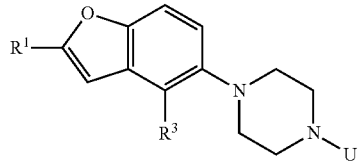

wherein $R^1$, $R^3$, and U are as defined in formula (II).

In a preferred aspect, the compounds of formula (II) are of formula (IIb):

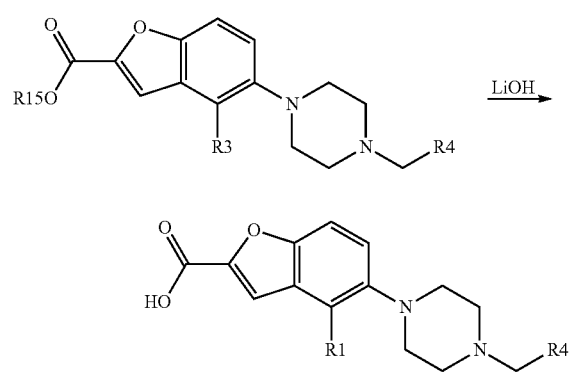

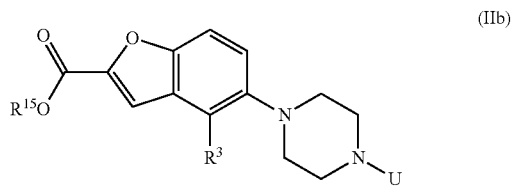

wherein U and $R^3$ are as defined in formula (IIa) and $R^{15}$ is as defined in formula (I).

EXAMPLES

Other features of the invention will become apparent in the course of the following descriptions of exemplary embodiments. These examples are given for illustration of the invention and are not intended to be limiting thereof.

Example 1

{5-[4-(2,6-dichloro benzyl)piperazine-1-yl]-4-methyl-benzofuran-2-yl}-morpholin-4-yl-methanone

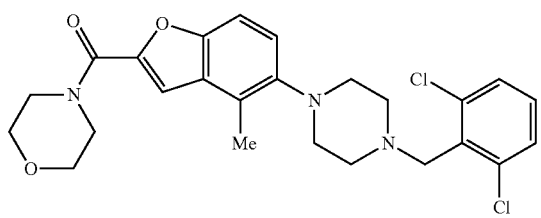 [SMILES: Cc1c(N2CCN(Cc3c(Cl)cccc3Cl)CC2)ccc2oc(C(=O)N3CCOCC3)cc12]

2-Methoxy-6-methylbenzaldehyde

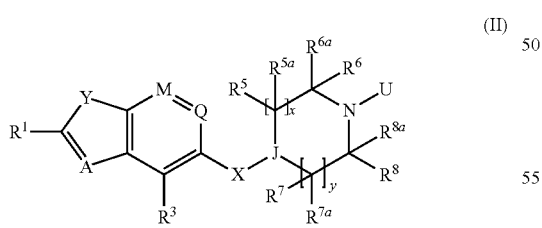

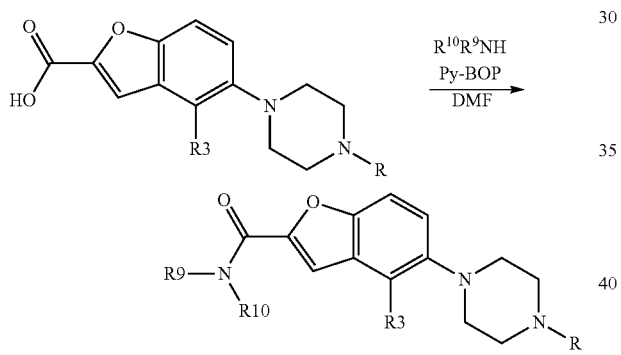

According to another object, the invention is directed to compounds of formula (II):

wherein $R^1$, Y, A, M, Q, X, J, $R^5$, $R^{5a}$, $R^6$, $R^{6a}$, $R^7$, $R^{7a}$, $R^8$, $R^{8a}$, x, and y are as defined in formula (I);

$R^3$ is halogen, $C_1$-$C_6$ alkyl, $C_1$-$C_6$ halogenoalkyl, $C_2$-$C_6$ alkenyl, $C_2$-$C_6$ alkynyl, $C_1$-$C_6$ alkoxy or CN; and U is H or an amine protecting group.

Preferably, the compound of formula (II) is of formula (IIa):

Potassium peroxy disulphate (89.31 g, 0.33 mol) and copper (II) sulphate pentahydrate (27.22 g, 0.11 mol) was added to a solution of 2,3-dimethylanisole (15 g, 0.11 mol) in acetonitrile water mixture (750 ml, 1:1). The reaction mixture was stirred for 15 min at reflux until no starting material remained as judged by TLC (Thin Layer Chromatography). On cooling the reaction mixture to room temperature, the product was extracted into dichloromethane (2×225 ml). The organic layer was washed with water (2×100 ml) and brine solution (100 ml). The organic layer was dried over sodium sulfate and concentrated under reduced pressure to give the crude product. Column chromatography using 4/96 ethyl acetate/hexane yielded 2-Methoxy-6-methylbenzaldehyde (7.32 g, 44.2%).

$^1$H NMR (300 MHz, CDCl$_3$), δ 2.60 (3H, s), 3.90 (3H, s), 6.80 (2H, t), 7.40 (1H, t), 10.65 (1H, s).

3-Bromo-6-methoxy-2-methyl-benzaldehyde

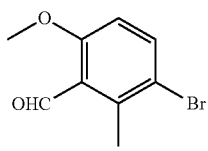

2-Methoxy-6-methylbenzaldehyde (7.32 g, 0.049 mol) in carbon tetrachloride (183 ml) was cooled to −10° C., and iron powder (150 mg, 0.002 mol) was added to it. Bromine (3.0 ml, 0.058 mol) was added over a period of 10 minutes. The mixture was stirred for 1 hour and then poured into water (225 ml). The organic layer was washed with sodium thiosulfate solution (2×50 ml), water (50 ml) and brine solution (50 ml). The organic layer was dried over sodium sulfate and concentrated under reduced pressure to give 3-Bromo-6-methoxy-2-methyl-benzaldehyde (10.32 g, 92.5%).

$^1$H NMR (300 MHz, CDCl$_3$), δ 2.65 (3H, s), 3.90 (3H, s), 6.78 (1H, d), 7.64 (1H, d), 10.50 (1H, s).

3-Bromo-6-hydroxy-2-methyl-benzaldehyde

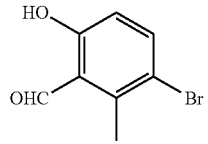

A solution of boron tribromide (12.62 ml, 0.087 mol) in dichloromethane (50 ml) was added to a stirred solution of 3-Bromo-6-methoxy-2-methyl-benzaldehyde (20.0 g, 0.087 mol) in dichloromethane (350 ml) under nitrogen at 0° C. The reaction mixture was stirred for 1.5 hours. Water (400 ml) was added cautiously and the mixture was stirred for 15 min. The organic layer was washed with sodium bicarbonate solution (200 ml), water (200 ml) and brine (200 ml). The organic layer was dried over sodium sulfate and concentrated under reduced pressure to give the crude product as orange brown solid. Column chromatography using 3/97 ethyl acetate/hexane yielded 3-Bromo-6-hydroxy-2-methyl-benzaldehyde (13.82 g, 73.6%).

$^1$H NMR (300 MHz, CDCl$_3$), δ 2.60 (3H, s), 6.76 (1H, d), 7.62 (1H, d), 10.4 (1H, s), 12.1 (1H, s).

5-Bromo-4-methyl-benzofuran-2-carboxylic acid ethyl ester

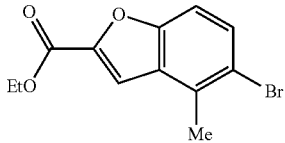 [SMILES: CCOC(=O)c1cc2c(C)c(Br)ccc2o1]

To a solution of 3-Bromo-6-hydroxy-2-methyl-benzaldehyde (6.8 g, 0.032 mol)) in anhydrous DMF (50 ml) was added potassium carbonate (13.1 g, 0.095 mol) and cooled to 0° C. Bromo ethyl acetate (7.1 ml, 0.063 mol) was added slowly. The reaction mixture was stirred for one hour at 0° C. The completion of the reaction was confirmed by TLC. The reaction mixture was then heated to 100° C. and maintained for 2 hours. After cooling to room temperature, ice water (250 ml) was added and the mixture was stirred for 20 minutes. The solid separated was filtered, washed with water (100 ml) and dried under vacuum, to get crude product. Column chromatography using 2/5 ethyl acetate/hexane yielded 5-Bromo-4-methyl-benzofuran-2-carboxylic acid ethyl ester (6.2 g, 69.6%)

$^1$H NMR (300 MHz, CDCl$_3$), δ 1.4 (3H, t), 2.60 (3H, s), 4.4 (2H, qt), 7.30 (1H, d), 7.44 (2H, m).

4-(2-ethoxycarbonyl-4-methyl-benzofuran-5-yl)-piperazine-1-carboxylic acid tert-butyl ester

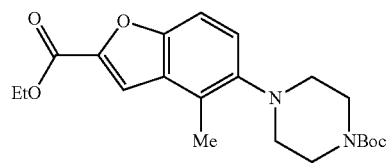 [SMILES: CCOC(=O)c1cc2c(C)c(N3CCN(C(=O)OC(C)(C)C)CC3)ccc2o1]

Toluene (30 ml) was stirred under argon atmosphere for 30 minutes at room temperature. Cesium carbonate (4.83 g, 0.015 mol), palladium acetate (0.19 g, 0.0008 mol), BINAP (0.66 g, 0.001 mol), 5-Bromo-4-methyl-benzofuran-2-carboxylic acid ethyl ester (3 g, 0.010 mol) and piperazine-1-carboxylic acid tert-butyl ester (2.16 g, 0.001 mol) was added with a regular interval of 30 minutes under argon atmosphere. The reaction mixture was stirred for 30 minutes at room temperature and then heated to reflux. The mixture was maintained at reflux for 16 hours. The reaction mixture was diluted with ethyl acetate (50 ml) and the inorganic material was filtered. The filtrate was then washed with water (2×15 ml), brine solution (50 ml). The organic layer was dried over sodium sulfate and concentrated under reduced pressure to get crude product as dark brown solid. Column chromatography using 5/95 ethyl acetate/hexane yielded 4-(2-ethoxycarbonyl-4-methyl-benzofuran-5-yl)-piperazine-1-carboxylic acid tert-butyl ester (1.4 g, 34.1%)

4-Methyl-5-piperazin-1-yl-benzofuran-2-carboxylic acid ethyl ester trifluoroacetic acid salt

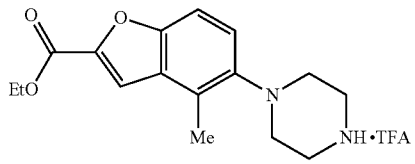 [SMILES: CCOC(=O)c1cc2c(C)c(N3CCNCC3)ccc2o1 ; "·TFA"]

Trifluoroacetic acid (3 ml) was added to a stirred solution of 4-(2-Ethoxycarbonyl-4-methyl-benzofuran-5-yl)-piperazine-1-carboxylic acid tert-butyl ester (1.4 g, 0.003 mol) in dichloromethane (10 ml) at room temperature. The reaction mixture was stirred for 2 hours. Solvent was concentrated under reduced pressure, the residue was triturated with diethyl ether (20 ml) to isolate 4-Methyl-5-piperazin-1-yl-benzofuran-2-carboxylic acid ethyl ester trifluoroacetic acid salt (1.25 g, 86.2%).

$^1$H NMR (300 MHz, CDCl$_3$), δ 1.4 (3H, t), 2.4 (3H, s), 2.9 (4H, t), 3.4 (4H, t), 4.4 (2H, qt) 720 (1H, d), 7.3-7.4 (2H, m).

5-[4-(2,6-Dichloro benzyl)-piperazine-1-yl]-4-methyl-benzofuran-2-carboxylic acid ethyl ester

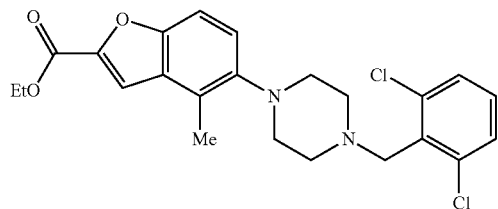 [SMILES: CCOC(=O)c1cc2c(C)c(N3CCN(Cc4c(Cl)cccc4Cl)CC3)ccc2o1]

To a stirred solution of 4-Methyl-5-[4-(2,2,2-trifluoroacetyl)-piperazin-1-yl]-benzofuran-2-carboxylic acid ethyl ester (0.15 g, 0.0003 mol) in dry THF was added triethyl amine (0.15 ml, 0.001 mol) and cooled to 0° C. and stirred under nitrogen. 2,6 dichloro benzyl bromide (0.107 g, 0.00045 mol) was added and stirred for 2 hours at room temperature. The completion of the reaction was confirmed by TLC. Solvent was concentrated under reduced pressure added water. The solid separated was filtered, washed with water (10 ml). After drying under vacuum, the crude product was isolated as brown solid. Column chromatography using 10/90 ethyl acetate/hexane yielded 5-[4-(2,6-Dichloro benzyl)-piperazine-1-yl]-4-methyl-benzofuran-2-carboxylic acid ethyl ester (0.13 g, 78%).

$^1$H NMR (300 MHz, CDCl$_3$) δ 1.4 (3H, t), 2.5 (3H, s), 2.8 (4H, s), 2.9 (4H, s), 3.9 (2H, s), 4.5 (2H, qt), 7.2 (2H, m), 7.4 (2H, m), 7.6 (1H, s).

5-[4-(2,6-Dichloro benzyl)-piperazine-1-yl]-4-methyl-benzofuran-2-carboxylic acid

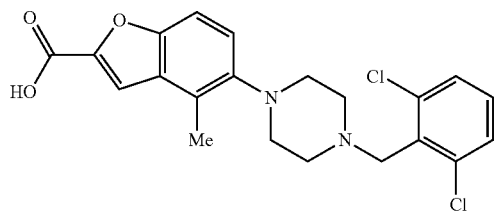 [SMILES: Cc1c(N2CCN(Cc3c(Cl)cccc3Cl)CC2)ccc2oc(C(=O)O)cc12]

To a solution of 5-[4-(2,6-Dichloro benzyl)-piperazine-1-yl]-4-methyl-benzofuran-2-carboxylic acid ethyl ester (0.08 g, 0.0001 mol) in THF:Water:Methanol (3:2:1) mixture (19 ml) was added lithium hydroxide (0.02 g, 0.0005 mol) at 0° C. The reaction mixture was stirred for 2 hours. The completion of the reaction was confirmed by TLC. Solvent was concentrated under reduced pressure added ice water. The pH of the mixture was made acidic with 1N HCl and the solid separated was filtered. After drying under vacuum, isolated 5-[4-(2,6-Dichloro benzyl)-piperazine-1-yl]-4-methyl-benzofuran-2-carboxylic acid (70 mg, 94%).

$^1$H NMR: (300 MHz, DMSO-d6) δ 3.2 (4H, s), 3.62 (4H, S), 4.72 (2H, s), 7.28 (1H, D), 7.7 (5H, m), 10.0 (1H, bs).

{5-[4-(2,6-dichloro benzyl)piperazine-1-yl]-4-methyl-benzofuran-2-yl}-morpholin-4-yl-methanone

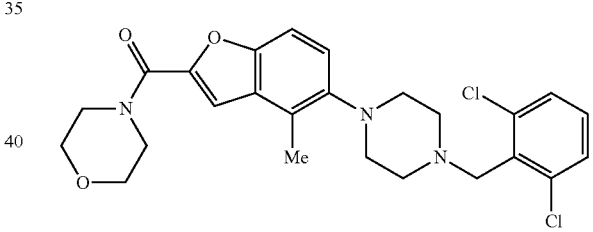

To a solution of 5-[4-(2,6-Dichloro benzyl)-piperazine-1-yl]-4-methyl-benzofuran-2-carboxylic acid (0.07 g, 0.00017 mol) in anhydrous DMF (275 ml) was added diisopropyl ethyl amine (0.08 ml, 0.0005 mol) and morpholine (0.16 ml, 0.00018 mol) under nitrogen atmosphere. The reaction mixture was stirred for 15 minutes, added Py-BOP (0.11 g, 0.0002 mol) and stirred for 1 hour. The completion of the reaction was confirmed by TLC. The reaction mixture was quenched into ice water. The solid separated was filtered. After drying under vacuum, the crude product was isolated as white solid. The crude product was purified by Prep HPLC using a Zorbax C-18 column with mobile phase 0.1% trifluoroacetic acid in water (A)/Acetonitrile (B) with a flow rate of 20 ml/min to yield {5-[4-(2,6-dichlorobenzyl)piperazine-1-yl]-4-methyl-benzofuran-2-yl}-morpholin-4-yl-methanone (35 mg, 43%).

$^1$H NMR (300 MHz, DMSO-d6), δ 3.4 (7H, s), 3.7 (5H, s), 3.9 (4H, s), 4.6 (2H, s), 7.2 (1H, d), 7.3 (1H, d), 7.4 (2H, d), 7.5 (2H, d).

LCMS (m/z) 488

HPLC: 98.23%

Example 2

4-Bromo-5-(4-tert-butoxycarbonylpiperazin-1-yl)-benzofuran-2-carboxylic acid

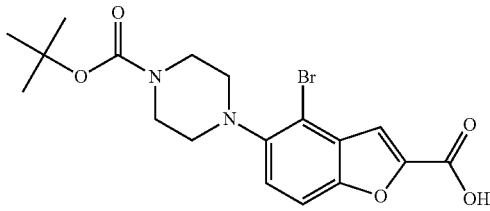 [SMILES: CC(C)(C)OC(=O)N1CCN(c2ccc3oc(C(=O)O)cc3c2Br)CC1]

5-(4-tert-butoxycarbonylpiperazin-1-yl)-2-hydroxy-benzaldehyde

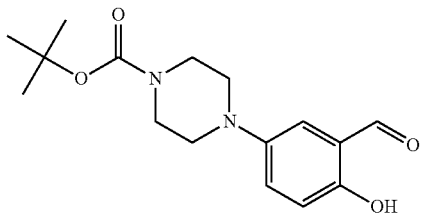 [SMILES: CC(C)(C)OC(=O)N1CCN(c2ccc(O)c(C=O)c2)CC1]

Toluene (9.7 L) was introduced into a reactor and degassed using vacuum/nitrogen. Under nitrogen at 23° C. was palladium acetate (11.0 g, 0.049 mol, 0.01 equiv.) was loaded and the mixture was stirred until complete dissolution of palladium. A solution of tri-tert-butyl-phosphine (10.0 g, 0.049 mol, 0.01 equiv.) in toluene (0.3 L) was then added, followed by the addition of 5-bromo-2-hydroxybenzaldehyde (1000 g, 4.97 mol, 1 equiv.), tert-butyl-1-piperazine-carboxylate (1065.4 g, 5.72 mol, 1.1 equiv.) and sodium-tert-butoxide (1052.4 g, 10.9 mol, 2.2 equiv.). The resulting yellow-orange solution was stirred for 22 h at 42° C. The red-brownish slurry was mixed with a mixture (pH around 5-6) of distilled water (8 L) and glacial acetic acid (800 mL), and stirred for 10 min. The organic phase was separated from the aqueous phase and washed twice with distilled water (2×8 L). The organic phase was then dried by addition of sodium sulphate (2.5 kg), stirred for 30 min. and filtered. The resulting dark-orange organic phase was weighed (9.65 kg) and an aliquot (100 g) was taken. The aliquot was concentrated in vacuo to yield a dark-orange oil which was purified by column chromatography (SiO₂, h: 30 cm, d: 4 cm, eluant: MTBE/heptane 1:1). The named compound was obtained as yellow crystals (8.9 g). Calculation of the total yield from the aliquot gave 56%. MS (ES+): 307 (M+H).

5-(4-tert-butoxycarbonylpiperazin-1-yl)-benzofuran-2-carboxylic acid ethyl ester

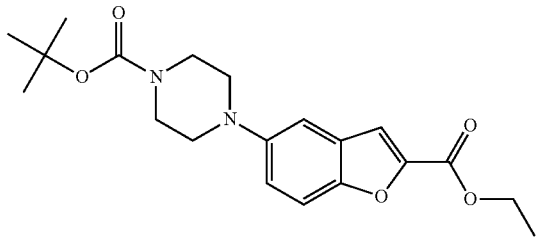 [SMILES: CCOC(=O)c1cc2cc(N3CCN(C(=O)OC(C)(C)C)CC3)ccc2o1]

$K_2CO_3$ (250 mg, 1.8 mmol) and Ethyl bromoacetate (0.20 ml, 1.7 mmol) were added to a solution of hydroxybenzaldehyde in NMP (5 mL). The mixture was stirred for 4 h at 110° C. The reaction was quenched with $H_2O$, extracted with EtOAc, washed with brine and water. After evaporation of EtOAc, the residue was recrystallized in a mixture of MTB/Heptane 5/1 to give yellow crystals (0.45 g, 70%). MS (ES+): 375 (M+H).

4-Bromo-5-(4-tert-butoxycarbonylpiperazin-1-yl)-benzofuran-2-carboxylic acid ethyl ester

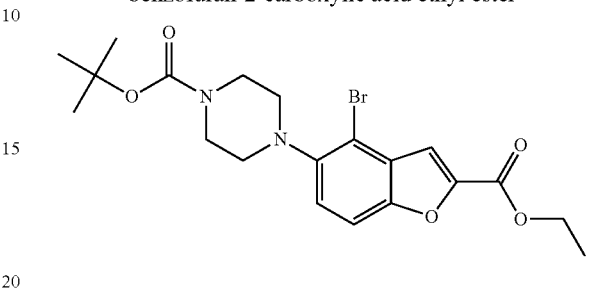

Bromine (12 mL, 0.23 mol) was added to a solution of ester (73 g, 0.19 mol) in presence of cat. iron (0.8 g, 14.3 mmol) in dichloromethane (900 mL). The reaction was stirred for 2 days at rt. The bromohydrate was filtrated off and dried under vacuum. The mother liquor was concentrated, the oily residue was taken into iPrOH and triturated with a spatula. The precipitate obtained was filtered off and dried. Combination of both filtrate provided 88 g, 70% of the desired compound. MS (ES+): 454 (M+H).

4-Bromo-5-(4-tert-butoxycarbonylpiperazin-1-yl)-benzofuran-2-carboxylic acid

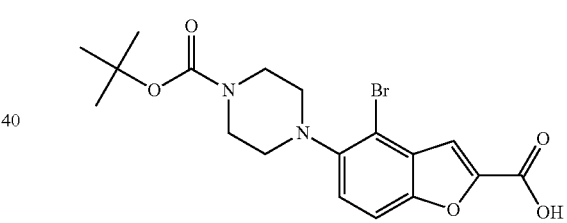

A solution of ester (4.6 g, 10.1 mmol) and potassium hydroxide (0.660 g, 11.7 mmol) in MeOH was stirred under reflux for 8 h. After removal of MeOH by evaporation, the residue was taken in $H_2O$. The free acid (4.1 g, 95%) was obtained as a white powder after precipitation by slow addition of 25% HCl under cooling conditions, filtration and drying. MS (ES+): 426 (M+H).

The compounds reported in the Table below were prepared according to similar methods or by well-known techniques by one of ordinary skill in the arts. Their mass spectral data are also reported therein.

| N° | Chemical Name | Analytical data MS (ES+): (M + H) |
|---|---|---|
| 1 | 4-(4-Bromo-2-ethoxycarbonyl-benzofuran-5-yl)-piperazine-1-carboxylic acid tert-butyl ester | 454 |
| 2 | 4-(4-Bromo-2-carboxy-benzofuran-5-yl)-piperazine-1-carboxylic acid tert-butyl ester | 426 |

-continued

| N° | Chemical Name | Analytical data MS (ES+): (M + H) |
|---|---|---|
| 3 | 4-(2-Carboxy-benzofuran-5-yl)-piperazine-1-carboxylic acid tert-butyl ester | 347 |
| 4 | 5-[4-(3-Methoxy-benzenesulfonyl)-piperazin-1-yl]-benzofuran-2-carboxylic acid amide | 416 |
| 5 | 5-[4-(4-Methoxy-benzenesulfonyl)-piperazin-1-yl]-benzofuran-2-carboxylic acid amide | 416 |
| 6 | 4-(2-Ethoxycarbonyl-benzofuran-5-yl)-piperazine-1-carboxylic acid tert-butyl ester | 375 |
| 7 | 5-[4-(3-Trifluoromethyl-benzyl)-piperazin-1-yl]-benzofuran-2-carboxylic acid amide | 404 |
| 8 | 5-[4-(3-Chloro-benzyl)-piperazin-1-yl]-benzofuran-2-carboxylic acid amide | 371 |
| 9 | 5-[4-(3-Fluoro-benzoyl)-piperazin-1-yl]-benzofuran-2-carboxylic acid amide | 368 |
| 10 | 5-[4-(3-Chloro-benzenesulfonyl)-piperazin-1-yl]-benzofuran-2-carboxylic acid amide | 421 |
| 11 | 4-Bromo-5-[4-(4-methoxy-benzenesulfonyl)-piperazin-1-yl]-benzofuran-2-carboxylic acid amide | 495 |
| 12 | 5-(4-Benzenesulfonyl-piperazin-1-yl)-benzofuran-2-carboxylic acid | 387 |
| 13 | 4-Bromo-5-[4-(3-fluoro-benzoyl)-piperazin-1-yl]-benzofuran-2-carboxylic acid | 448 |
| 14 | 4-Bromo-5-[4-(3-chloro-benzenesulfonyl)-piperazin-1-yl]-benzofuran-2-carboxylic acid | 501 |
| 15 | 4-Bromo-5-[4-(3-fluoro-benzenesulfonyl)-piperazin-1-yl]-benzofuran-2-carboxylic acid | 484 |
| 16 | 4-Bromo-5-[4-(pyrrolidine-1-carbonyl)-piperazin-1-yl]-benzofuran-2-carboxylic acid | 423 |
| 17 | 4-Bromo-5-[4-(3-chloro-benzyl)-piperazin-1-yl]-benzofuran-2-carboxylic acid | 451 |
| 18 | 4-(2-Carboxy-benzofuran-5-ylamino)-piperidine-1-carboxylic acid tert-butyl ester | 361 |
| 19 | 2-[4-(4-Bromo-2-carboxy-benzofuran-5-yl)-piperazine-1-carbonyl]-pyrrolidine-1-carboxylic acid tert-butyl ester | 523 |
| 20 | 4-(4-Chloro-2-ethoxycarbonyl-benzofuran-5-yl)-piperazine-1-carboxylic acid tert-butyl ester | 410 |
| 21 | 4-(2-Carboxy-4-chloro-benzofuran-5-yl)-piperazine-1-carboxylic acid tert-butyl ester | 382 |
| 22 | 5-(4-Benzyl-piperazin-1-yl)-benzofuran-2-carboxylic acid | 337 |
| 23 | 4-Bromo-5-[4-(3-trifluoromethyl-benzyl)-piperazin-1-yl]-benzofuran-2-carboxylic acid | 484 |
| 24 | 5-[4-(3-Methoxy-benzenesulfonyl)-piperazin-1-yl]-benzofuran-2-carboxylic acid | 417 |
| 25 | 4-Bromo-5-[4-(3-methoxy-benzenesulfonyl)-piperazin-1-yl]-benzofuran-2-carboxylic acid | 496 |
| 26 | 4-Bromo-5-[4-(4-methoxy-benzenesulfonyl)-piperazin-1-yl]-benzofuran-2-carboxylic acid | 496 |
| 27 | 4-Bromo-5-[4-(pyrrolidine-2-carbonyl)-piperazin-1-yl]-benzofuran-2-carboxylic acid | 423 |
| 28 | 5-[4-(Adamantane-1-carbonyl)-piperazin-1-yl]-4-bromo-benzofuran-2-carboxylic acid | 488 |
| 29 | 4-Bromo-5-[4-(3-chloro-benzoyl)-piperazin-1-yl]-benzofuran-2-carboxylic acid | 465 |
| 30 | 4-Bromo-5-[4-(2-fluoro-benzoyl)-piperazin-1-yl]-benzofuran-2-carboxylic acid | 434 |
| 31 | 4-Bromo-5-[4-(3-fluoro-benzoyl)-piperazin-1-yl]-benzofuran-2-carboxylic acid | 434 |
| 32 | 5-(4-Benzoyl-piperazin-1-yl)-4-bromo-benzofuran-2-carboxylic acid | 430 |
| 33 | 5-[4-(3,5-Difluoro-benzyl)-piperazin-1-yl]-benzofuran-2-carboxylic acid amide | 372 |
| 34 | 4-Bromo-5-[4-(3-trifluoromethyl-benzyloxy)-piperidin-1-yl]-benzofuran-2-carboxylic acid | 499 |
| 35 | 4-Bromo-5-[4-(3-chloro-benzyloxy)-piperidin-1-yl]-benzofuran-2-carboxylic acid | 466 |
| 36 | 4-Bromo-5-[4-(2-chloro-benzenesulfonyl)-piperazin-1-yl]-benzofuran-2-carboxylic acid | 501 |
| 37 | 4-Bromo-5-[4-(4-chloro-benzenesulfonyl)-piperazin-1-yl]-benzofuran-2-carboxylic acid | 501 |
| 38 | 4-Bromo-5-[4-(4-fluoro-benzyl)-piperazin-1-yl]-benzofuran-2-carboxylic acid | 434 |
| 39 | 4-Bromo-5-[4-(2-chloro-benzyl)-piperazin-1-yl]-benzofuran-2-carboxylic acid | 451 |
| 40 | 4-Bromo-5-[4-(4-chloro-benzyl)-piperazin-1-yl]-benzofuran-2-carboxylic acid | 451 |
| 41 | 4-Bromo-5-[4-(pyridin-2-yloxy)-piperidin-1-yl]-benzofuran-2-carboxylic acid | 418 |
| 42 | 4-Bromo-5-[4-(3-trifluoromethyl-benzyl)-piperazin-1-yl]-benzofuran-2-carboxylic acid amide | 483 |
| 43 | 5-[4-(3-Trifluoromethoxy-benzyl)-piperazin-1-yl]-benzofuran-2-carboxylic acid amide | 420 |
| 44 | 4-Bromo-5-[4-(3-trifluoromethoxy-benzyl)-piperazin-1-yl]-benzofuran-2-carboxylic acid amide | 499 |
| 45 | 4-Bromo-5-[4-(3-cyano-benzenesulfonyl)-piperazin-1-yl]-benzofuran-2-carboxylic acid amide | 491 |
| 46 | 4-Bromo-5-(4-tert-butylcarbamoyl-piperazin-1-yl)-benzofuran-2-carboxylic acid | 425 |
| 47 | 4-Bromo-5-[4-(3-fluoro-benzenesulfonyl)-piperazin-1-yl]-benzofuran-2-carboxylic acid amide | 483 |
| 48 | 4-Bromo-5-[4-(3,5-dichloro-benzoyl)-piperazin-1-yl]-benzofuran-2-carboxylic acid amide | 498 |
| 49 | 4-Bromo-5-[4-(3,5-difluoro-benzyl)-piperazin-1-yl]-benzofuran-2-carboxylic acid amide | 451 |
| 50 | 4-Bromo-5-(4-pyridin-3-ylmethyl-piperazin-1-yl)-benzofuran-2-carboxylic acid | 417 |
| 51 | 4-Bromo-5-(4-pyridin-4-ylmethyl-piperazin-1-yl)-benzofuran-2-carboxylic acid | 417 |
| 52 | 4-Bromo-5-[4-(3-trifluoromethoxy-benzyl)-piperazin-1-yl]-benzofuran-2-carboxylic acid | 500 |
| 53 | 4-Bromo-5-[4-(3-phenoxy-benzyl)-piperazin-1-yl]-benzofuran-2-carboxylic acid | 508 |
| 54 | 4-Bromo-5-[4-(3,5-dimethoxy-benzyl)-piperazin-1-yl]-benzofuran-2-carboxylic acid | 476 |
| 55 | 5-[4-(3-Allyl-2-hydroxy-benzyl)-piperazin-1-yl]-4-bromo-benzofuran-2-carboxylic acid | 472 |
| 56 | 5-(4-Benzenesulfonyl-piperazin-1-yl)-4-bromo-benzofuran-2-carboxylic acid | 466 |
| 57 | 4-Bromo-5-(4-tert-butylcarbamoyl-piperidin-1-yl)-benzofuran-2-carboxylic acid | 424 |
| 58 | 4-Chloro-5-[4-(2-chloro-benzyl)-piperazin-1-yl]-benzofuran-2-carboxylic acid | 406 |
| 59 | 4-Chloro-5-[4-(3-chloro-benzyl)-piperazin-1-yl]-benzofuran-2-carboxylic acid | 406 |
| 60 | 4-Chloro-5-[4-(4-chloro-benzyl)-piperazin-1-yl]-benzofuran-2-carboxylic acid | 406 |
| 61 | 4-Chloro-5-[4-(2-fluoro-benzyl)-piperazin-1-yl]-benzofuran-2-carboxylic acid | 390 |
| 62 | 4-Chloro-5-[4-(3-fluoro-benzyl)-piperazin-1-yl]-benzofuran-2-carboxylic acid | 390 |
| 63 | 4-Chloro-5-[4-(4-fluoro-benzyl)-piperazin-1-yl]-benzofuran-2-carboxylic acid | 390 |
| 64 | 4-Chloro-5-[4-(3-trifluoromethyl-benzyl)-piperazin-1-yl]-benzofuran-2-carboxylic acid | 440 |
| 65 | 4-Chloro-5-[4-(3-trifluoromethoxy-benzyl)-piperazin-1-yl]-benzofuran-2-carboxylic acid | 456 |
| 66 | 5-[4-(3-Carboxy-benzyl)-piperazin-1-yl]-4-chloro-benzofuran-2-carboxylic acid | 416 |
| 67 | 4-Chloro-5-(4-pyridin-3-ylmethyl-piperazin-1-yl)-benzofuran-2-carboxylic acid | 373 |
| 68 | 4-Chloro-5-[4-(2-chloro-benzenesulfonyl)-piperazin-1-yl]-benzofuran-2-carboxylic acid | 456 |
| 69 | 4-Chloro-5-[4-(3-chloro-benzenesulfonyl)-piperazin-1-yl]-benzofuran-2-carboxylic acid | 456 |
| 70 | 4-Chloro-5-[4-(4-chloro-benzenesulfonyl)-piperazin-1-yl]-benzofuran-2-carboxylic acid | 456 |
| 71 | 4-Chloro-5-[4-(4-methoxy-benzenesulfonyl)-piperazin-1-yl]-benzofuran-2-carboxylic acid | 452 |
| 72 | 4-Chloro-5-[4-(3-methoxy-benzenesulfonyl)-piperazin-1-yl]-benzofuran-2-carboxylic acid | 452 |
| 73 | 4-Chloro-5-[4-(3-fluoro-benzoyl)-piperazin-1-yl]-benzofuran-2-carboxylic acid | 404 |
| 74 | 4-Chloro-5-[4-(3,5-dichloro-benzoyl)-piperazin-1-yl]-benzofuran-2-carboxylic acid | 455 |
| 75 | 4-Chloro-5-[4-(3-fluoro-benzenesulfonyl)-piperazin-1-yl]-benzofuran-2-carboxylic acid | 440 |
| 76 | 4-Chloro-5-[4-(3-cyano-benzenesulfonyl)-piperazin-1-yl]-benzofuran-2-carboxylic acid | 447 |

-continued

| N° | Chemical Name | Analytical data MS (ES+): (M + H) |
|---|---|---|
| 77 | 4-Bromo-5-[4-(2-chloro-benzenesulfonyl)-piperazin-1-yl]-benzofuran-2-carboxylic acid amide | 500 |
| 78 | 4-Bromo-5-[4-(3-fluoro-benzenesulfonyl)-piperazin-1-yl]-benzofuran-2-carboxylic acid ethoxy-amide | 527 |
| 79 | 4-Bromo-5-[4-(3-trifluoromethyl-benzoyl)-piperazin-1-yl]-benzofuran-2-carboxylic acid | 498 |
| 80 | 4-Bromo-5-[4-(3-trifluoromethoxy-benzoyl)-piperazin-1-yl]-benzofuran-2-carboxylic acid | 514 |
| 81 | 4-Bromo-5-[4-(3-methoxy-benzoyl)-piperazin-1-yl]-benzofuran-2-carboxylic acid | 460 |
| 82 | 4-Bromo-5-[4-(2,5-dichloro-benzoyl)-piperazin-1-yl]-benzofuran-2-carboxylic acid | 499 |
| 83 | 4-Bromo-5-[4-(3,5-dichloro-benzoyl)-piperazin-1-yl]-benzofuran-2-carboxylic acid | 499 |
| 84 | 4-Bromo-5-[4-(2-methyl-1H-benzoimidazole-4-carbonyl)-piperazin-1-yl]-benzofuran-2-carboxylic acid | 484 |
| 85 | 4-Bromo-5-[4-(5-trifluoromethyl-pyridin-2-yloxy)-piperidin-1-yl]-benzofuran-2-carboxylic acid | 486 |
| 86 | 4-Bromo-5-[1-(3-chloro-benzyl)-piperidin-4-ylamino]-benzofuran-2-carboxylic acid | 465 |
| 87 | 4-Chloro-5-[4-(3-chloro-benzoyl)-piperazin-1-yl]-benzofuran-2-carboxylic acid | 420 |
| 88 | 4-Chloro-5-[4-(2,5-dichloro-benzoyl)-piperazin-1-yl]-benzofuran-2-carboxylic acid | 455 |
| 89 | 4-Chloro-5-[4-(3-methoxy-benzoyl)-piperazin-1-yl]-benzofuran-2-carboxylic acid | 416 |
| 90 | 4-Chloro-5-[4-(3-trifluoromethyl-benzoyl)-piperazin-1-yl]-benzofuran-2-carboxylic acid | 454 |
| 91 | 4-Chloro-5-[4-(3-trifluoromethoxy-benzoyl)-piperazin-1-yl]-benzofuran-2-carboxylic acid | 470 |
| 92 | 4-Chloro-5-[4-(2-methyl-1H-benzoimidazole-4-carbonyl)-piperazin-1-yl]-benzofuran-2-carboxylic acid | 440 |
| 93 | 5-[4-(1H-Benzoimidazole-5-carbonyl)-piperazin-1-yl]-4-chloro-benzofuran-2-carboxylic acid | 426 |
| 94 | 4-Chloro-5-[4-(2,5-dichloro-benzyl)-piperazin-1-yl]-benzofuran-2-carboxylic acid | 441 |
| 95 | 4-Chloro-5-[4-(3,5-dimethoxy-benzyl)-piperazin-1-yl]-benzofuran-2-carboxylic acid | 432 |
| 96 | 4-Chloro-5-[4-(3-chloro-phenylmethanesulfonyl)-piperazin-1-yl]-benzofuran-2-carboxylic acid | 470 |
| 97 | 5-[4-(2-Chloro-benzenesulfonyl)-piperazin-1-yl]-4-methyl-benzofuran-2-carboxylic acid | 436 |
| 98 | 5-[4-(3-Fluoro-benzenesulfonyl)-piperazin-1-yl]-4-methyl-benzofuran-2-carboxylic acid | 419 |
| 99 | 4-(2-Carboxy-4-methyl-benzofuran-5-yl)-piperazine-1-carboxylic acid tert-butyl ester | 361 |
| 100 | 4-(2-Carboxy-4-chloro-benzofuran-5-yl)-[1,4]diazepane-1-carboxylic acid tert-butyl ester | 396 |
| 101 | 4-(4-Bromo-2-carboxy-benzofuran-5-yl)-[1,4]diazepane-1-carboxylic acid tert-butyl ester | 440 |
| 102 | 4-Bromo-5-[4-(2-chloro-benzenesulfonyl)-[1,4]diazepan-1-yl]-benzofuran-2-carboxylic acid | 515 |
| 103 | 4-Chloro-5-[4-(2-chloro-benzenesulfonyl)-[1,4]diazepan-1-yl]-benzofuran-2-carboxylic acid | 470 |
| 104 | 4-Chloro-5-[4-(5-trifluoromethyl-pyridin-2-yloxy)-piperidin-1-yl]-benzofuran-2-carboxylic acid | 442 |
| 105 | 4-Bromo-5-[1-(3-chloro-benzenesulfonyl)-piperidin-4-ylamino]-benzofuran-2-carboxylic acid | 515 |
| 106 | {4-Bromo-5-[4-(2-chloro-benzenesulfonyl)-piperazin-1-yl]-benzofuran-2-yl}-morpholin-4-yl-methanone | 570 |
| 107 | 4-Bromo-5-[4-(2-chloro-benzenesulfonyl)-piperazin-1-yl]-benzofuran-2-carboxylic acid (2-methoxy-ethyl)-amide | 558 |
| 108 | 4-Bromo-5-[4-(2,5-dichloro-benzenesulfonyl)-piperazin-1-yl]-benzofuran-2-carboxylic acid | 535 |
| 109 | 4-Bromo-5-[4-(2,5-dichloro-benzyl)-piperazin-1-yl]-benzofuran-2-carboxylic acid | 485 |
| 110 | 5-[4-(1H-Benzoimidazole-5-carbonyl)-piperazin-1-yl]-4-bromo-benzofuran-2-carboxylic acid | 470 |
| 111 | 4-Bromo-5-[4-(2,6-dichloro-benzoyl)-piperazin-1-yl]-benzofuran-2-carboxylic acid | 499 |
| 112 | 5-[4-(2,6-Dichloro-benzoyl)-piperazin-1-yl]-4-methyl-benzofuran-2-carboxylic acid | 434 |
| 113 | 5-[4-(2,5-Dichloro-benzoyl)-piperazin-1-yl]-4-methyl-benzofuran-2-carboxylic acid | 434 |
| 114 | 5-[4-(3,5-Dichloro-benzoyl)-piperazin-1-yl]-4-methyl-benzofuran-2-carboxylic acid | 434 |
| 115 | 4-Methyl-5-[4-(3-trifluoromethoxy-benzoyl)-piperazin-1-yl]-benzofuran-2-carboxylic acid | 449 |
| 116 | 5-[4-(2-Chloro-benzyl)-piperazin-1-yl]-4-methyl-benzofuran-2-carboxylic acid | 386 |
| 117 | 5-[4-(3-Chloro-benzyl)-piperazin-1-yl]-4-methyl-benzofuran-2-carboxylic acid | 386 |
| 118 | 5-[4-(2,5-Dichloro-benzyl)-piperazin-1-yl]-4-methyl-benzofuran-2-carboxylic acid | 420 |
| 119 | 5-[4-(3-Fluoro-benzyl)-piperazin-1-yl]-4-methyl-benzofuran-2-carboxylic acid | 369 |
| 120 | 4-Methyl-5-[4-(3-trifluoromethyl-benzyl)-piperazin-1-yl]-benzofuran-2-carboxylic acid | 419 |
| 121 | 4-Methyl-5-[4-(3-trifluoromethoxy-benzyl)-piperazin-1-yl]-benzofuran-2-carboxylic acid | 435 |
| 122 | 5-[4-(3-Chloro-benzenesulfonyl)-piperazin-1-yl]-4-methyl-benzofuran-2-carboxylic acid | 436 |
| 123 | 5-[4-(2,5-Dichloro-benzenesulfonyl)-piperazin-1-yl]-4-methyl-benzofuran-2-carboxylic acid | 470 |
| 124 | 5-[4-(3-Chloro-phenylmethanesulfonyl)-piperazin-1-yl]-4-methyl-benzofuran-2-carboxylic acid | 450 |
| 125 | 4-Bromo-5-[4-(2-chloro-6-fluoro-benzyl)-piperazin-1-yl]-benzofuran-2-carboxylic acid | 469 |
| 126 | 4-Chloro-5-[4-(2-chloro-6-fluoro-benzyl)-piperazin-1-yl]-benzofuran-2-carboxylic acid | 424 |
| 127 | 4-Bromo-5-[4-(3-chloro-phenylmethanesulfonyl)-piperazin-1-yl]-benzofuran-2-carboxylic acid | 515 |
| 128 | 4-Chloro-5-[1-(3-chloro-benzenesulfonyl)-piperidin-4-ylamino]-benzofuran-2-carboxylic acid | 470 |
| 129 | 4-Bromo-5-(3,4-dihydro-1H-isoquinolin-2-yl)-benzofuran-2-carboxylic acid | 373 |
| 130 | 4-Bromo-5-[4-(3-chloro-phenoxy)-piperidin-1-yl]-benzofuran-2-carboxylic acid | 452 |
| 131 | 4-Bromo-5-[4-(4-trifluoromethyl-pyrimidin-2-yloxy)-piperidin-1-yl]-benzofuran-2-carboxylic acid | 487 |
| 132 | 4-Bromo-5-[4-(2-fluoro-benzenesulfonyl)-piperazin-1-yl]-benzofuran-2-carboxylic acid | 484 |
| 133 | 5-[4-(2-Fluoro-benzenesulfonyl)-piperazin-1-yl]-4-methyl-benzofuran-2-carboxylic acid | 419 |
| 134 | 4-Bromo-5-[4-(2,6-dichloro-benzenesulfonyl)-piperazin-1-yl]-benzofuran-2-carboxylic acid | 535 |
| 135 | 5-[4-(2,6-Dichloro-benzenesulfonyl)-piperazin-1-yl]-4-methyl-benzofuran-2-carboxylic acid | 470 |
| 136 | 4-Chloro-5-[4-(2,6-dichloro-benzenesulfonyl)-piperazin-1-yl]-benzofuran-2-carboxylic acid | 491 |
| 137 | 4-Bromo-5-[4-(2,3-dichloro-benzenesulfonyl)-piperazin-1-yl]-benzofuran-2-carboxylic acid | 535 |
| 138 | 5-[4-(2,3-Dichloro-benzenesulfonyl)-piperazin-1-yl]-4-methyl-benzofuran-2-carboxylic acid | 470 |
| 139 | 4-Chloro-5-[4-(2,3-dichloro-benzenesulfonyl)-piperazin-1-yl]-benzofuran-2-carboxylic acid | 491 |
| 140 | 4-Chloro-5-[4-(2,5-dichloro-benzenesulfonyl)-piperazin-1-yl]-benzofuran-2-carboxylic acid | 491 |
| 141 | 4-Bromo-5-[4-(2,3-dichloro-benzoyl)-piperazin-1-yl]-benzofuran-2-carboxylic acid | 499 |
| 142 | 4-Methyl-5-[4-(3-trifluoromethyl-benzoyl)-piperazin-1-yl]-benzofuran-2-carboxylic acid | 433 |
| 143 | 4-Methyl-5-[4-(2-methyl-1H-benzoimidazole-4-carbonyl)-piperazin-1-yl]-benzofuran-2-carboxylic acid | 419 |
| 144 | 5-[4-(2-Fluoro-benzyl)-piperazin-1-yl]-4-methyl-benzofuran-2-carboxylic acid | 369 |
| 145 | 5-[4-(2-Chloro-6-fluoro-benzyl)-piperazin-1-yl]-4-methyl-benzofuran-2-carboxylic acid | 404 |
| 146 | 5-[4-(2,6-Dichloro-benzyl)-piperazin-1-yl]-4-methyl-benzofuran-2-carboxylic acid | 420 |
| 147 | 4-Bromo-5-[4-(3,5-dichloro-benzyl)-piperazin-1-yl]-benzofuran-2-carboxylic acid | 485 |
| 148 | 5-[4-(3,5-Dichloro-benzyl)-piperazin-1-yl]-4-methyl-benzofuran-2-carboxylic acid | 420 |

-continued

| N° | Chemical Name | Analytical data MS (ES+): (M + H) |
|---|---|---|
| 149 | 4-Chloro-5-[4-(3,5-dichloro-benzyl)-piperazin-1-yl]-benzofuran-2-carboxylic acid | 441 |
| 150 | 5-[4-(3-Allyl-2-hydroxy-benzyl)-piperazin-1-yl]-4-methyl-benzofuran-2-carboxylic acid | 408 |
| 151 | 5-[4-(2,3-Dimethoxy-benzyl)-piperazin-1-yl]-4-methyl-benzofuran-2-carboxylic acid | 411 |
| 152 | 4-Bromo-5-[4-(5-chloro-thiophen-2-ylmethyl)-piperazin-1-yl]-benzofuran-2-carboxylic acid | 457 |
| 153 | 4-Methyl-5-[4-(5-trifluoromethyl-pyridin-2-yloxy)-piperidin-1-yl]-benzofuran-2-carboxylic acid | 421 |
| 154 | 4-(2-Carboxy-4-cyano-benzofuran-5-yl)-piperazine-1-carboxylic acid tert-butyl ester | 372 |
| 155 | 4-Bromo-5-[4-(4-chloro-phenoxy)-piperidin-1-yl]-benzofuran-2-carboxylic acid | 452 |
| 156 | 4-Bromo-5-[4-(3-ethoxy-benzyl)-piperazin-1-yl]-benzofuran-2-carboxylic acid | 460 |
| 157 | 4-Bromo-5-[4-(2-chloro-benzenesulfonyl)-piperazin-1-yl]-benzofuran-2-carboxylic acid benzylamide | 590 |
| 158 | 5-[4-(3,5-Dichloro-2-hydroxy-benzenesulfonyl)-piperazin-1-yl]-4-methyl-benzofuran-2-carboxylic acid | 486 |
| 159 | 5-(4-Benzo[1,3]dioxol-4-ylmethyl-piperazin-1-yl)-4-bromo-benzofuran-2-carboxylic acid | 460 |
| 160 | 4-Bromo-5-[4-(2,6-dichloro-benzyl)-piperazin-1-yl]-benzofuran-2-carboxylic acid | 485 |
| 161 | 4-Bromo-5-[4-(2,4-dichloro-benzyl)-piperazin-1-yl]-benzofuran-2-carboxylic acid | 485 |
| 162 | 5-[4-(2-Allyloxy-benzyl)-piperazin-1-yl]-4-bromo-benzofuran-2-carboxylic acid | 472 |
| 163 | 4-Bromo-5-[4-(3-trifluoromethyl-phenoxy)-piperidin-1-yl]-benzofuran-2-carboxylic acid | 485 |
| 164 | 4-Bromo-5-[4-(4-trifluoromethyl-phenoxy)-piperidin-1-yl]-benzofuran-2-carboxylic acid | 485 |
| 165 | 4-Bromo-5-{4-[cyclopropanecarbonyl-(2,4-dichloro-phenyl)-amino]-piperidin-1-yl}-benzofuran-2-carboxylic acid | 553 |
| 166 | 4-Bromo-5-{4-[(4-chloro-benzyl)-cyclopropanecarbonyl-amino]-piperidin-1-yl}-benzofuran-2-carboxylic acid | 533 |
| 167 | 5-{4-[3-(2,6-Dichloro-phenyl)-5-isopropyl-isoxazole-4-carbonyl]-piperazin-1-yl}-4-methyl-benzofuran-2-carboxylic acid | 543 |
| 168 | 4-Bromo-5-[4-(2-trifluoromethyl-benzyl)-piperazin-1-yl]-benzofuran-2-carboxylic acid | 484 |
| 169 | 5-[4-(3-Allyloxy-benzyl)-piperazin-1-yl]-4-bromo-benzofuran-2-carboxylic acid | 472 |
| 170 | 5-[4-(3-Allyl-2-methoxy-benzyl)-piperazin-1-yl]-4-methyl-benzofuran-2-carboxylic acid | 422 |
| 171 | 4-Bromo-5-[4-(3-tert-butyl-2-hydroxy-benzyl)-piperazin-1-yl]-benzofuran-2-carboxylic acid | 488 |
| 172 | 4-Methyl-5-(4-naphthalen-1-ylmethyl-piperazin-1-yl)-benzofuran-2-carboxylic acid | 401 |
| 173 | 4-Bromo-5-[4-(2-hydroxy-naphthalen-1-ylmethyl)-piperazin-1-yl]-benzofuran-2-carboxylic acid | 482 |
| 174 | 4-Bromo-5-[4-(2-trifluoromethyl-benzenesulfonyl)-piperazin-1-yl]-benzofuran-2-carboxylic acid | 534 |
| 175 | 4-Bromo-5-[4-(3-trifluoromethyl-benzenesulfonyl)-piperazin-1-yl]-benzofuran-2-carboxylic acid | 534 |
| 176 | 4-Bromo-5-[4-(2,6-dichloro-benzenesulfonyl)-[1,4]diazepan-1-yl]-benzofuran-2-carboxylic acid | 549 |
| 177 | {4-Bromo-5-[4-(2,6-dichloro-benzenesulfonyl)-[1,4]diazepan-1-yl]-benzofuran-2-yl}-morpholin-4-yl-methanone | 618 |
| 178 | {4-Bromo-5-[4-(2,6-dichloro-benzenesulfonyl)-[1,4]diazepan-1-yl]-benzofuran-2-yl}-piperidin-1-yl-methanone | 616 |
| 179 | {5-[4-(3,5-Dichloro-2-hydroxy-benzenesulfonyl)-piperazin-1-yl]-4-methyl-benzofuran-2-yl}-morpholin-4-yl-methanone | 555 |
| 180 | {4-Bromo-5-[4-(2-fluoro-benzenesulfonyl)-piperazin-1-yl]-benzofuran-2-yl}-morpholin-4-yl-methanone | 553 |
| 181 | {4-Bromo-5-[4-(2-chloro-benzenesulfonyl)-piperazin-1-yl]-benzofuran-2-yl}-piperidin-1-yl-methanone | 568 |
| 182 | {4-Bromo-5-[4-(2,6-dichloro-benzenesulfonyl)-piperazin-1-yl]-benzofuran-2-yl}-piperidin-1-yl-methanone | 602 |
| 183 | {4-Bromo-5-[4-(2,6-dichloro-benzenesulfonyl)-piperazin-1-yl]-benzofuran-2-yl}-morpholin-4-yl-methanone | 604 |
| 184 | 4-Bromo-5-[4-(2,6-dichloro-benzoyl)-[1,4]diazepan-1-yl]-benzofuran-2-carboxylic acid | 513 |
| 185 | 5-[4-(3-Allyl-2-hydroxy-benzyl)-[1,4]diazepan-1-yl]-4-bromo-benzofuran-2-carboxylic acid | 486 |
| 186 | 5-[4-(3,5-Dichloro-2-hydroxy-benzyl)-piperazin-1-yl]-4-methyl-benzofuran-2-carboxylic acid | 436 |
| 187 | 4-Methyl-5-[4-(2,3,6-trichloro-benzyl)-piperazin-1-yl]-benzofuran-2-carboxylic acid | 455 |
| 188 | 5-[4-(2,3-Dichloro-benzyl)-piperazin-1-yl]-4-methyl-benzofuran-2-carboxylic acid | 420 |
| 189 | 4-Bromo-5-{4-[4-bromo-5-(4-fluoro-2-methoxy-phenyl)-3-methyl-pyrazol-1-yl]-piperidin-1-yl}-benzofuran-2-carboxylic acid | 608 |
| 190 | 4-Bromo-5-{4-[5-(4-fluoro-2-methoxy-phenyl)-3-methyl-pyrazol-1-yl]-piperidin-1-yl}-benzofuran-2-carboxylic acid | 529 |
| 191 | 4-Bromo-5-(4-{[(4-chloro-benzyl)-cyclopropylmethyl-amino]-methyl}-piperidin-1-yl)-benzofuran-2-carboxylic acid | 533 |
| 192 | {4-Bromo-5-[4-(2,6-dichloro-benzoyl)-[1,4]diazepan-1-yl]-benzofuran-2-yl}-morpholin-4-yl-methanone | 582 |
| 193 | 4-Bromo-5-[4-(2,6-dichloro-benzoyl)-piperazin-1-yl]-benzofuran-2-carboxylic acid | 455 |
| 194 | 4-Chloro-5-[1-(2,6-dichloro-benzenesulfonyl)-piperidin-4-ylamino]-benzofuran-2-carboxylic acid | 505 |
| 195 | {4-Chloro-5-[4-(2,3-dichloro-benzenesulfonyl)-piperazin-1-yl]-benzofuran-2-yl}-morpholin-4-yl-methanone | 560 |
| 196 | {4-Bromo-5-[4-(2,6-dichloro-benzenesulfonyl)-piperazin-1-yl]-benzofuran-2-yl}-(4-methyl-piperazin-1-yl)-methanone | 617 |
| 197 | 4-Bromo-5-[4-(2,6-dichloro-benzenesulfonyl)-piperazin-1-yl]-benzofuran-2-carboxylic acid (2-dimethylamino-ethyl)-amide | 605 |
| 198 | 4-Chloro-5-[4-(2-hydroxy-benzyl)-piperazin-1-yl]-benzofuran-2-carboxylic acid | 388 |
| 199 | {5-[4-(2,6-Dichloro-benzyl)-piperazin-1-yl]-4-methyl-benzofuran-2-yl}-morpholin-4-yl-methanone | 489 |
| 200 | 4-Chloro-5-[4-(2,6-dichloro-benzenesulfonyl)-[1,4]diazepan-1-yl]-benzofuran-2-carboxylic acid | 505 |
| 201 | 5-[4-(2,3-Dichloro-benzenesulfonyl)-[1,4]diazepan-1-yl]-4-methyl-benzofuran-2-carboxylic acid | 484 |
| 202 | {5-[4-(2,3-Dichloro-benzenesulfonyl)-[1,4]diazepan-1-yl]-4-methyl-benzofuran-2-yl}-morpholin-4-yl-methanone | 553 |
| 203 | 4-Chloro-5-[4-(2,3-dichloro-benzenesulfonyl)-[1,4]diazepan-1-yl]-benzofuran-2-carboxylic acid | 505 |
| 204 | {4-Chloro-5-[4-(2,3-dichloro-benzenesulfonyl)-[1,4]diazepan-1-yl]-benzofuran-2-yl}-morpholin-4-yl-methanone | 574 |
| 205 | 4-Chloro-5-[4-(2,5-dichloro-benzenesulfonyl)-[1,4]diazepan-1-yl]-benzofuran-2-carboxylic acid | 505 |
| 206 | {4-Chloro-5-[4-(2,5-dichloro-benzenesulfonyl)-[1,4]diazepan-1-yl]-benzofuran-2-yl}-morpholin-4-yl-methanone | 574 |
| 207 | 5-[4-(2,5-Dichloro-benzenesulfonyl)-[1,4]diazepan-1-yl]-4-methyl-benzofuran-2-carboxylic acid | 484 |
| 208 | {5-[4-(2,5-Dichloro-benzenesulfonyl)-[1,4]diazepan-1-yl]-4-methyl-benzofuran-2-yl}-morpholin-4-yl-methanone | 553 |
| 209 | {4-Chloro-5-[4-(2,6-dichloro-benzenesulfonyl)-[1,4]diazepan-1-yl]-benzofuran-2-yl}-morpholin-4-yl-methanone | 574 |
| 210 | 4-Chloro-5-[4-(2-chloro-6-hydroxy-benzyl)-piperazin-1-yl]-benzofuran-2-carboxylic acid | 422 |
| 211 | 4-Chloro-5-[4-(2-chloro-6-methoxy-benzyl)-piperazin-1-yl]-benzofuran-2-carboxylic acid | 436 |
| 212 | 4-Chloro-5-[4-(3-ethoxy-2-hydroxy-benzyl)-piperazin-1-yl]-benzofuran-2-carboxylic acid | 432 |

-continued

| N° | Chemical Name | Analytical data MS (ES+): (M + H) |
|---|---|---|
| 213 | 4-Chloro-5-[4-(2-chloro-3-trifluoromethyl-benzyl)-piperazin-1-yl]-benzofuran-2-carboxylic acid | 474 |
| 214 | 5-{4-[3-(2,6-Dichloro-phenyl)-5-isopropyl-isoxazol-4-ylmethyl]-piperazin-1-yl}-4-methyl-benzofuran-2-carboxylic acid | 529 |
| 215 | 5-[4-(2,6-Dichloro-benzyl)-piperazin-1-yl]-4-methyl-benzofuran-2-carboxylic acid amide | 419 |
| 216 | 5-[4-(2,6-Dichloro-benzyl)-[1,4]diazepan-1-yl]-4-methyl-benzofuran-2-carboxylic acid | 434 |
| 217 | {5-[4-(2,6-Dichloro-benzyl)-[1,4]diazepan-1-yl]-4-methyl-benzofuran-2-yl}-(4-methyl-piperazin-1-yl)-methanone | 516 |
| 218 | {4-Bromo-5-[4-(2,6-dichloro-benzoyl)-[1,4]diazepan-1-yl]-benzofuran-2-yl}-piperidin-1-yl-methanone | 580 |
| 219 | 4-Bromo-5-[1-(2,6-dichloro-benzoyl)-piperidin-4-ylamino]-benzofuran-2-carboxylic acid | 513 |
| 220 | 4-Bromo-5-[1-(2,3-dichloro-benzoyl)-piperidin-4-ylamino]-benzofuran-2-carboxylic acid | 513 |
| 221 | 4-Chloro-5-[4-(2,3-dihydro-indol-1-yl)-piperidin-1-yl]-benzofuran-2-carboxylic acid | 398 |
| 222 | 5-(4-Benzhydryl-piperazin-1-yl)-4-methyl-benzofuran-2-carboxylic acid | 427 |
| 223 | 4-Bromo-5-[4-(2,6-dichloro-benzenesulfonylamino)-piperidin-1-yl]-benzofuran-2-carboxylic acid | 549 |
| 224 | 4-Chloro-5-[4-(2-methyl-5-thiophen-2-yl-2H-pyrazol-3-ylmethyl)-piperazin-1-yl]-benzofuran-2-carboxylic acid | 457 |
| 225 | 5-[(1S,4S)-5-(2,6-Dichloro-benzenesulfonyl)-2,5-diaza-bicyclo[2.2.1]hept-2-yl]-4-methyl-benzofuran-2-carboxylic acid | 482 |
| 226 | 5-[4-(2,4-Dichloro-phenylcarbamoyl)-piperidin-1-yl]-4-methyl-benzofuran-2-carboxylic acid | 448 |

BIOLOGICAL EXPERIMENTS

FXR-SRC-1 Cofactor Recruitment Assay

Typically the assay involves the use of a recombinant Glutathione-S-transferase (GST)-nuclear receptor ligand binding domain (LBD) fusion protein and a synthetic biotinylated peptide sequence derived from the receptor interacting domain of a co-activator peptide such as the steroid receptor coactivator 1 (SRC-1). GST-LBD is labelled with a europium chelate (donor) via a europium-tagged anti-GST antibody, and the co-activator peptide is labelled with allophycocyanin-APC (acceptor) via a streptavidin-biotin linkage.

In the presence of an agonist for the nuclear receptor, the peptide is recruited to the GST-LBD, bringing europium and allophycocyanin into close proximity to enable energy transfer from the europium chelate to the allophycocyanin. Upon excitation of the complex with light at 340 nm, excitation energy absorbed by the europium chelate is transmitted to the allophycocyanin moiety resulting in emission at 665 nm. If the europium chelate is not brought into close proximity to the allophycocyanin moiety there is little or no energy transfer and excitation of the europium chelate results in emission at 615 nm. Thus the intensity of light emitted at 665 nm gives an indication of the strength of the protein-protein interaction. The activity of a nuclear receptor agonist can be measured by determining the ability of a compound to bind the nuclear receptor in this test (EC50) and compare to the ability of reference compound to bind this same nuclear receptor.

Materials

Synthetic biotinylated peptide based on residue 676-760 of steroid receptor coactivator 1 (SRC-1) as described by Lannone, M. A. et al, Cytometry 44:326-337 (2001): the peptide was custom-synthetised, biotinylated at the N-terminus and C-terminus was carboxy-acidized by Invitrogen.

Streptavidin conjugated to SureLight®-Allophycocyanin and Lance® Eu-W1024-labelled anti-GST antibody were purchased from PerkinElmer.

Black 384 well plates were purchased from Greiner.

Preparation of human Farsenoid X Receptor ligand binding domain—GST fusion protein (GST-FXR LBD)

The coding sequence of Human FXR-LBD (amino acid 248-476) was derived form Genbank accession number NM_005123. The coding region of the FXR ligand binding domain was cloned into a modified pGEX4T1 vector using Gateway Technology according to the manufacturers protocol to get vector pGEXDest-TEV-FXR (248-476). GST-FXRLBD fusion protein was expressed in E. coli BL21 at 18° C. for 6 h in 2TY medium by induction with 0.1 mM of isopropyl-b-D-thiogalactopyranoside (IPTG) at an OD of 0.6 T.

Cell lysis was carried out by french press and after centrifugation the supernatant was then purified using a Glutathione Sepharose 4FF column. The FXR pool was concentrated and loaded onto a Superdex 200 gelfiltration column. FXR containing fractions were pooled, concentrated and stored in aliquots by −80° C.

Assay Buffer: 5 mM $MgCl_2$, 100 mM KCl, 20 mM Hepes, 10% Glycerol, pH 7.5. Just before used, solid DTT is added to the assay buffer to a final concentration of 1 mM.

Methods

Test compounds and controls were serial diluted in DMSO at 100 fold the final concentration tested. This serial dilution was then diluted 1:13.05 in assay buffer and 3 μl of diluted product was added per 384 well in the assay.

2 mixes were prepared:

Protein mix: per well, 50 ng GST-FXRLBD fusion protein in 10 μl assay buffer+11.44% BSA Peptide mix: per well, 40 ng SRC1 peptide, 80 ng Streptavidin conjugated to SureLight®-Allophycocyanin, 1 ng Lance® Eu-W1024-labelled anti-GST antibody in 10 μl assay buffer+8.8% BSA.

A mix without peptide (same than peptide mix were peptide was replaced by water) was also set-up and for each compound (each concentration tested) a basal fluorescence level was determined in order to detect self-fluorescent compounds.

To each well 10 μl of protein mix, 3 μl of compound and 10 μl of peptide mix were mixed.

Plates were incubated 1 hour at room temperature and fluorescence was read on a time resolved mode on a Wallac/Perkin Elmer Victor2 counter.

Data Reduction

For each compound concentration, fluorescent signal ratio: F665/F615×1000 was calculated. Background control (no compound, DMSO) was substracted.

EC50 (hereafter denoted EC50 FXR SRC-1) were calculated plotting data in Graphpad Prism4 software Transactivation Assay This cell based assay was used to identify compounds for which their binding to FXR-LBD induces gene reporter transactivation.

Cells were transiently co-transfected with an expression plasmid where a chimeric nuclear receptor comprising FXR ligand binding domain fused to Gal4 DNA binding domain and a reporter plasmid where luciferase gene is under the control of an inducible promoter comprising five Gal4 responsive elements.

Treatment of transient cotransfected cells with an agonist for the FXR nuclear receptor induces conformational changes to the chimeric receptor, increasing its transcriptional activity which is reflected by an increase in expression of the reporter gene (luciferase) measured using luciferase assay.

Materials

Reporter plasmid was constructed by placing cDNA encoding firefly luciferase immediately downstream from the herpes virus thymidine kinase promoter and 5 times Gal4 responsive element.

Expression plasmid was constructed by placing under the control of a CMV promoter the Gal4 DNA binding domain fused in frame with FXR ligand binding domain (Genbank accession number NM_005123 base 1086 to 1796).

Methods

CV-1 Clone 5 cells (Monkey African green kidney fibroblast) were cultured in DMEM Glutamax medium containing 10% FBS at 37° C. in a 95% $CO_2$: 5% $O_2$ atmosphere. Cells were seeded in 96 well plates at a density of 20000 cells/well and transfected with the Gal4-FXRLBD chimeric plasmid and the luciferase reporter plasmid. Transfection was done using Lipofectamine reagent (Invitrogen) according to the protocol and using 5 ng Gal4-FXRLBD chimeric plasmid for 150 ng luciferase reporter plasmid in a volume of 60 µl per well. 4 hours after transfection, medium was replaced by 100 µl fresh culture medium. 24 hours after transfection, treatment by compound was realised adding directly to the well 100 µl test compound diluted in culture medium (2% DMSO maximum).

Following incubation of the cells for 24 hours with compounds, medium was taken out, cells were washed once by 200 µl PBS and 100 µl of Steady-Glo Luciferase Assay System (Promega, E2510) was added to lyse cells and initiate luciferase reaction. After 20 min incubation at room temperature in the dark, luminescence as a measure of luciferase activity was detected using a Luminoscan (Perkin Elmer).

Data Reduction

Transcriptional activation in the presence of test compound was expressed as fold-change in luminescence compared to that of cells incubated in the absence of tested compound (DMSO control).

EC50 value (hereafter denoted EC50 FXR TA) was calculated plotting data in Graphpad Prism4 software.

Results

The compounds according to formula (I) have an activity in at least one of the above assays (EC50 SRC-1, EC50 TA), notably an EC50 in the range of 10 nM to 10 µM.

| Example | EC50 FXR SRC-1 (µM) | EC50 FXR TA (µM) |
|---------|---------------------|------------------|
| 165     | 0.106               | n.d.             |
| 135     | 0.015               | 1.95             |

The invention claimed is:

1. A compound, which is
4-(4-Bromo-2-ethoxycarbonyl-benzofuran-5-yl)-piperazine-1-carboxylic acid tert-butyl ester
4-(4-Bromo-2-carboxy-benzofuran-5-yl)-piperazine-1-carboxylic acid tert-butyl ester
5-[4-(3-Methoxy-benzenesulfonyl)-piperazin-1-yl]-benzofuran-2-carboxylic acid amide
5-[4-(4-Methoxy-benzenesulfonyl)-piperazin-1-yl]-benzofuran-2-carboxylic acid amide
5-[4-(3-Trifluoromethyl-benzyl)-piperazin-1-yl]-benzofuran-2-carboxylic acid amide
5-[4-(3-Chloro-benzyl)-piperazin-1-yl]-benzofuran-2-carboxylic acid amide
5-[4-(3-Fluoro-benzoyl)-piperazin-1-yl]-benzofuran-2-carboxylic acid amide
5-[4-(3-Chloro-benzenesulfonyl)-piperazin-1-yl]-benzofuran-2-carboxylic acid amide
4-Bromo-5-[4-(4-methoxy-benzenesulfonyl)-piperazin-1-yl]-benzofuran-2-carboxylic acid amide
5-(4-Benzenesulfonyl-piperazin-1-yl)-benzofuran-2-carboxylic acid
4-Bromo-5-[4-(3-fluoro-benzoyl)-piperazin-1-yl]-benzofuran-2-carboxylic acid
4-Bromo-5-[4-(3-chloro-benzenesulfonyl)-piperazin-1-yl]-benzofuran-2-carboxylic acid
4-Bromo-5-[4-(3-fluoro-benzenesulfonyl)-piperazin-1-yl]-benzofuran-2-carboxylic acid
4-Bromo-5-[4-(pyrrolidine-1-carbonyl)-piperazin-1-yl]-benzofuran-2-carboxylic acid
4-Bromo-5-[4-(3-chloro-benzyl)-piperazin-1-yl]-benzofuran-2-carboxylic acid
2-[4-(4-Bromo-2-carboxy-benzofuran-5-yl)-piperazine-1-carbonyl]-pyrrolidine-1-carboxylic acid tert-butyl ester
4-(4-Chloro-2-ethoxycarbonyl-benzofuran-5-yl)-piperazine-1-carboxylic acid tert-butyl ester
4-(2-Carboxy-4-chloro-benzofuran-5-yl)-piperazine-1-carboxylic acid tert-butyl ester
4-Bromo-5-[4-(3-trifluoromethyl-benzyl)-piperazin-1-yl]-benzofuran-2-carboxylic acid
5-[4-(3-Methoxy-benzenesulfonyl)-piperazin-1-yl]-benzofuran-2-carboxylic acid
4-Bromo-5-[4-(3-methoxy-benzenesulfonyl)-piperazin-1-yl]-benzofuran-2-carboxylic acid
4-Bromo-5-[4-(4-methoxy-benzenesulfonyl)-piperazin-1-yl]-benzofuran-2-carboxylic acid
4-Bromo-5-[4-(pyrrolidine-2-carbonyl)-piperazin-1-yl]-benzofuran-2-carboxylic acid
5-[4-(Adamantane-1-carbonyl)-piperazin-1-yl]-4-bromo-benzofuran-2-carboxylic acid
4-Bromo-5-[4-(3-chloro-benzoyl)-piperazin-1-yl]-benzofuran-2-carboxylic acid
4-Bromo-5-[4-(2-fluoro-benzyl)-piperazin-1-yl]-benzofuran-2-carboxylic acid
4-Bromo-5-[4-(3-fluoro-benzyl)-piperazin-1-yl]-benzofuran-2-carboxylic acid
5-(4-Benzoyl-piperazin-1-yl)-4-bromo-benzofuran-2-carboxylic acid
5-[4-(3,5-Difluoro-benzyl)-piperazin-1-yl]-benzofuran-2-carboxylic acid amide
4-Bromo-5-[4-(2-chloro-benzenesulfonyl)-piperazin-1-yl]-benzofuran-2-carboxylic acid
4-Bromo-5-[4-(4-chloro-benzenesulfonyl)-piperazin-1-yl]-benzofuran-2-carboxylic acid
4-Bromo-5-[4-(4-fluoro-benzyl)-piperazin-1-yl]-benzofuran-2-carboxylic acid
4-Bromo-5-[4-(2-chloro-benzyl)-piperazin-1-yl]-benzofuran-2-carboxylic acid
4-Bromo-5-[4-(4-chloro-benzyl)-piperazin-1-yl]-benzofuran-2-carboxylic acid
4-Bromo-5-[4-(3-trifluoromethyl-benzyl)-piperazin-1-yl]-benzofuran-2-carboxylic acid amide
5-[4-(3-Trifluoromethoxy-benzyl)-piperazin-1-yl]-benzofuran-2-carboxylic acid amide
4-Bromo-5-[4-(3-trifluoromethoxy-benzyl)-piperazin-1-yl]-benzofuran-2-carboxylic acid amide
4-Bromo-5-[4-(3-cyano-benzenesulfonyl)-piperazin-1-yl]-benzofuran-2-carboxylic acid
4-Bromo-5-(4-tert-butylcarbamoyl-piperazin-1-yl)-benzofuran-2-carboxylic acid 4-Bromo-5-[4-(3-fluoro-benzenesulfonyl)-piperazin-1-yl]-benzofuran-2-carboxylic acid amide
4-Bromo-5-[4-(3,5-dichloro-benzoyl)-piperazin-1-yl]-benzofuran-2-carboxylic acid amide
4-Bromo-5-[4-(3,5-difluoro-benzyl)-piperazin-1-yl]-benzofuran-2-carboxylic acid amide
4-Bromo-5-(4-pyridin-3-ylmethyl-piperazin-1-yl)-benzofuran-2-carboxylic acid
4-Bromo-5-(4-pyridin-4-ylmethyl-piperazin-1-yl)-benzofuran-2-carboxylic acid
4-Bromo-5-[4-(3-trifluoromethoxy-benzyl)-piperazin-1-yl]-benzofuran-2-carboxylic acid
4-Bromo-5-[4-(3-phenoxy-benzyl)-piperazin-1-yl]-benzofuran-2-carboxylic acid
4-Bromo-5-[4-(3,5-dimethoxy-benzyl)-piperazin-1-yl]-benzofuran-2-carboxylic acid
5-[4-(3-Allyl-2-hydroxy-benzyl)-piperazin-1-yl]-4-bromo-benzofuran-2-carboxylic acid
5-(4-Benzenesulfonyl-piperazin-1-yl)-4-bromo-benzofuran-2-carboxylic acid
4-Chloro-5-[4-(2-chloro-benzyl)-piperazin-1-yl]-benzofuran-2-carboxylic acid
4-Chloro-5-[4-(3-chloro-benzyl)-piperazin-1-yl]-benzofuran-2-carboxylic acid
4-Chloro-5-[4-(4-chloro-benzyl)-piperazin-1-yl]-benzofuran-2-carboxylic acid
4-Chloro-5-[4-(2-fluoro-benzyl)-piperazin-1-yl]-benzofuran-2-carboxylic acid
4-Chloro-5-[4-(3-fluoro-benzyl)-piperazin-1-yl]-benzofuran-2-carboxylic acid
4-Chloro-5-[4-(4-fluoro-benzyl)-piperazin-1-yl]-benzofuran-2-carboxylic acid
4-Chloro-5-[4-(3-trifluoromethyl-benzyl)-piperazin-1-yl]-benzofuran-2-carboxylic acid
4-Chloro-5-[4-(3-trifluoromethoxy-benzyl)-piperazin-1-yl]-benzofuran-2-carboxylic acid
5-[4-(3-Carboxy-benzyl)-piperazin-1-yl]-4-chloro-benzofuran-2-carboxylic acid
4-Chloro-5-(4-pyridin-3-ylmethyl-piperazin-1-yl)-benzofuran-2-carboxylic acid
4-Chloro-5-[4-(2-chloro-benzenesulfonyl)-piperazin-1-yl]-benzofuran-2-carboxylic acid
4-Chloro-5-[4-(3-chloro-benzenesulfonyl)-piperazin-1-yl]-benzofuran-2-carboxylic acid
4-Chloro-5-[4-(4-chloro-benzenesulfonyl)-piperazin-1-yl]-benzofuran-2-carboxylic acid
4-Chloro-5-[4-(4-methoxy-benzenesulfonyl)-piperazin-1-yl]-benzofuran-2-carboxylic acid
4-Chloro-5-[4-(3-methoxy-benzenesulfonyl)-piperazin-1-yl]-benzofuran-2-carboxylic acid
4-Chloro-5-[4-(3-fluoro-benzoyl)-piperazin-1-yl]-benzofuran-2-carboxylic acid
4-Chloro-5-[4-(3,5-dichloro-benzoyl)-piperazin-1-yl]-benzofuran-2-carboxylic acid
4-Chloro-5-[4-(3-fluoro-benzenesulfonyl)-piperazin-1-yl]-benzofuran-2-carboxylic acid
4-Chloro-5-[4-(3-cyano-benzenesulfonyl)-piperazin-1-yl]-benzofuran-2-carboxylic acid
4-Bromo-5-[4-(2-chloro-benzenesulfonyl)-piperazin-1-yl]-benzofuran-2-carboxylic acid amide
4-Bromo-5-[4-(3-fluoro-benzenesulfonyl)-piperazin-1-yl]-benzofuran-2-carboxylic acid ethoxy-amide
4-Bromo-5-[4-(3-trifluoromethyl-benzoyl)-piperazin-1-yl]-benzofuran-2-carboxylic acid
4-Bromo-5-[4-(3-trifluoromethoxy-benzoyl)-piperazin-1-yl]-benzofuran-2-carboxylic acid
4-Bromo-5-[4-(3-methoxy-benzoyl)-piperazin-1-yl]-benzofuran-2-carboxylic acid
4-Bromo-5-[4-(2,5-dichloro-benzoyl)-piperazin-1-yl]-benzofuran-2-carboxylic acid
4-Bromo-5-[4-(3,5-dichloro-benzoyl)-piperazin-1-yl]-benzofuran-2-carboxylic acid
4-Bromo-5-[4-(2-methyl-1H-benzoimidazole-4-carbonyl)-piperazin-1-yl]-benzofuran-2-carboxylic acid
4-Chloro-5-[4-(3-chloro-benzoyl)-piperazin-1-yl]-benzofuran-2-carboxylic acid
4-Chloro-5-[4-(2,5-dichloro-benzoyl)-piperazin-1-yl]-benzofuran-2-carboxylic acid
4-Chloro-5-[4-(3-methoxy-benzoyl)-piperazin-1-yl]-benzofuran-2-carboxylic acid
4-Chloro-5-[4-(3-trifluoromethyl-benzoyl)-piperazin-1-yl]-benzofuran-2-carboxylic acid
4-Chloro-5-[4-(3-trifluoromethoxy-benzoyl)-piperazin-1-yl]-benzofuran-2-carboxylic acid
4-Chloro-5-[4-(2-methyl-1H-benzoimidazole-4-carbonyl)-piperazin-1-yl]-benzofuran-2-carboxylic acid
5-[4-(1H-Benzoimidazole-5-carbonyl)-piperazin-1-yl]-4-chloro-benzofuran-2-carboxylic acid
4-Chloro-5-[4-(2,5-dichloro-benzyl)-piperazin-1-yl]-benzofuran-2-carboxylic acid
4-Chloro-5-[4-(3,5-dimethoxy-benzyl)-piperazin-1-yl]-benzofuran-2-carboxylic acid
4-Chloro-5-[4-(3-chloro-phenylmethanesulfonyl)-piperazin-1-yl]-benzofuran-2-carboxylic acid
5-[4-(2-Chloro-benzenesulfonyl)-piperazin-1-yl]-4-methyl-benzofuran-2-carboxylic acid
5-[4-(3-Fluoro-benzenesulfonyl)-piperazin-1-yl]-4-methyl-benzofuran-2-carboxylic acid
4-(2-Carboxy-4-methyl-benzofuran-5-yl)-piperazine-1-carboxylic acid tert-butyl ester
{4-Bromo-5-[4-(2-chloro-benzenesulfonyl)-piperazin-1yl]-benzofuran-2-yl}morpholin-4-yl-methanone
4-Bromo-5-[4-(2-chloro-benzenesulfonyl)-piperazin-1-yl]-benzofuran-2-carboxylic acid (2-methoxy-ethyl)-amide
4-Bromo-5-[4-(2,5-dichloro-benzenesulfonyl)-piperazin-1-yl]-benzofuran-2-carboxylic acid
4-Bromo-5-[4-(2,5-dichloro-benzyl)-piperazin-1-yl]-benzofuran-2-carboxylic acid
5-[4-(1H-Benzoimidazole-5-carbonyl)-piperazin-1-yl]-4-bromo-benzofuran-2-carboxylic acid
4-Bromo-5-[4-(2,6-dichloro-benzoyl)-piperazin-1-yl]-benzofuran-2-carboxylic acid
5-[4-(2,6-Dichloro-benzoyl)-piperazin-1-yl]-4-methyl-benzofuran-2-carboxylic acid
5-[4-(2,5-Dichloro-benzoyl)-piperazin-1-yl]-4-methyl-benzofuran-2-carboxylic acid
5-[4-(3,5-Dichloro-benzoyl)-piperazin-1-yl]-4-methyl-benzofuran-2-carboxylic acid
4-Methyl-5-[4-(3-trifluoromethoxy-benzoyl)-piperazin-1-yl]-benzofuran-2-carboxylic acid
5-[4-(2-Chloro-benzyl)-piperazin-1-yl]-4-methyl-benzofuran-2-carboxylic acid
5-[4-(3-Chloro-benzyl)-piperazin-1-yl]-4-methyl-benzofuran-2-carboxylic acid
5-[4-(2,5-Dichloro-benzyl)-piperazin-1-yl]-4-methyl-benzofuran-2-carboxylic acid
5-[4-(3-Fluoro-benzyl)-piperazin-1-yl]-4-methyl-benzofuran-2-carboxylic acid
4-Methyl-5-[4-(3-trifluoromethyl-benzyl)-piperazin-1-yl]-benzofuran-2-carboxylic acid
4-Methyl-5-[4-(3-trifluoromethoxy-benzyl)-piperazin-1-yl]-benzofuran-2-carboxylic acid 5-[4-(3-Chloro-benzenesulfonyl)-piperazin-1-yl]-4-methyl-benzofuran-2-carboxylic acid
5-[4-(2,5-Dichloro-benzenesulfonyl)-piperazin-1-yl]-4-methyl-benzofuran-2-carboxylic acid
5-[4-(3-Chloro-phenylmethanesulfonyl)-piperazin-1-yl]-4-methyl-benzofuran-2-carboxylic acid
4-Bromo-5-[4-(2-chloro-6-fluoro-benzyl)-piperazin-1-yl]-benzofuran-2-carboxylic acid
4-Chloro-5-[4-(2-chloro-6-fluoro-benzyl)-piperazin-1-yl]-benzofuran-2-carboxylic acid
4-Bromo-5-[4-(3-chloro-phenylmethanesulfonyl)-piperazin-1-yl]-benzofuran-2-carboxylic acid
4-Bromo-5-[4-(2-fluoro-benzenesulfonyl)-piperazin-1-yl]-benzofuran-2-carboxylic acid
5-[4-(2-Fluoro-benzenesulfonyl)-piperazin-1-yl]-4-methyl-benzofuran-2-carboxylic acid
4-Bromo-5-[4-(2,6-dichloro-benzenesulfonyl)-piperazin-1-yl]-benzofuran-2-carboxylic acid
5-[4-(2,6-Dichloro-benzenesulfonyl)-piperazin-1-yl]-4-methyl-benzofuran-2-carboxylic acid
4-Chloro-5-[4-(2,6-dichloro-benzenesulfonyl)-piperazin-1-yl]-benzofuran-2-carboxylic acid
4-Bromo-5-[4-(2,3-dichloro-benzenesulfonyl)-piperazin-1-yl]-benzofuran-2-carboxylic acid
5-[4-(2,3-Dichloro-benzenesulfonyl)-piperazin-1-yl]-4-methyl-benzofuran-2-carboxylic acid
4-Chloro-5-[4-(2,3-dichloro-benzenesulfonyl)-piperazin-1-yl]-benzofuran-2-carboxylic acid
4-Chloro-5-[4-(2,5-dichloro-benzenesulfonyl)-piperazin-1-yl]-benzofuran-2-carboxylic acid
4-Bromo-5-[4-(2,3-dichloro-benzoyl)-piperazin-1-yl]-benzofuran-2-carboxylic acid
4-Methyl-5-[4-(3-trifluoromethyl-benzoyl)-piperazin-1-yl]-benzofuran-2-carboxylic acid
4-Methyl-5-[4-(2-methyl-1H-benzoimidazole-4-carbonyl)-piperazin-1-yl]-benzofuran-2-carboxylic acid
5-[4-(2-Fluoro-benzyl)-piperazin-1-yl]-4-methyl-benzofuran-2-carboxylic acid
5-[4-(2-Chloro-6-fluoro-benzyl)-piperazin-1-yl]-4-methyl-benzofuran-2-carboxylic acid
5-[4-(2,6-Dichloro-benzyl)-piperazin-1-yl]-4-methyl-benzofuran-2-carboxylic acid
4-Bromo-5-[4-(3,5-dichloro-benzyl)-piperazin-1-yl]-benzofuran-2-carboxylic acid
5-[4-(3,5-Dichloro-benzyl)-piperazin-1-yl]-4-methyl-benzofuran-2-carboxylic acid
4-Chloro-5-[4-(3,5-dichloro-benzyl)-piperazin-1-yl]-benzofuran-2-carboxylic acid
5-[4-(3-Allyl-2-hydroxy-benzyl)-piperazin-1-yl]-4-methyl-benzofuran-2-carboxylic acid
5-[4-(2,3-Dimethoxy-benzyl)-piperazin-1-yl]-4-methyl-benzofuran-2-carboxylic acid
4-Bromo-5-[4-(5-chloro-thiophen-2-ylmethyl)-piperazin-1-yl]-benzofuran-2-carboxylic acid
4-(2-Carboxy-4-cyano-benzofuran-5-yl)-piperazine-1-carboxylic acid tert-butyl ester
4-Bromo-5-[4-(3-ethoxy-benzyl)-piperazin-1-yl]-benzofuran-2-carboxylic acid
4-Bromo-5-[4-(2-chloro-benzenesulfonyl)-piperazin-1-yl]-benzofuran-2-carboxylic acid benzylamide
5-[4-(3,5-Dichloro-2-hydroxy-benzenesulfonyl)-piperazin-1-yl]-4-methyl-benzofuran-2-carboxylic acid
5-(4-Benzo[1,3]dioxol-4-ylmethyl-piperazin-1-yl)-4-bromo-benzofuran-2-carboxylic acid
4-Bromo-5-[4-(2,6-dichloro-benzyl)-piperazin-1-yl]-benzofuran-2-carboxylic acid
4-Bromo-5-[4-(2,4-dichloro-benzyl)-piperazin-1-yl]-benzofuran-2-carboxylic acid
5-[4-(2-Allyloxy-benzyl)-piperazin-1-yl]-4-bromo-benzofuran-2-carboxylic acid
5-{4-[3-(2,6-Dichloro-phenyl)-5-isopropyl-isoxazole-4-carbonyl]-piperazin-1-yl}-4-methyl-benzofuran-2-carboxylic acid
4-Bromo-5-[4-(2-trifluoromethyl-benzyl)-piperazin-1-yl]-benzofuran-2-carboxylic acid
5-[4-(3-Allyloxy-benzyl)-piperazin-1-yl]-4-bromo-benzofuran-2-carboxylic acid
5-[4-(3-Allyl-2-methoxy-benzyl)-piperazin-1-yl]-4-methyl-benzofuran-2-carboxylic acid
4-Bromo-5-[4-(3-tert-butyl-2-hydroxy-benzyl)-piperazin-1-yl]-benzofuran-2-carboxylic acid
4-Methyl-5-(4-naphthalen-1-ylmethyl-piperazin-1-yl)-benzofuran-2-carboxylic acid
4-Bromo-5-[4-(2-hydroxy-naphthalen-1-ylmethyl)-piperazin-1-yl]-benzofuran-2-carboxylic acid
4-Bromo-5-[4-(2-trifluoromethyl-benzenesulfonyl)-piperazin-1-yl]-benzofuran-2-carboxylic acid
4-Bromo-5-[4-(3-trifluoromethyl-benzenesulfonyl)-piperazin-1-yl]-benzofuran-2-carboxylic acid
{5-[4-(3,5-Dichloro-2-hydroxy-benzenesulfonyl)-piperazin-1-yl]-4-methyl-benzofuran-2-yl}-morpholin-4-yl-methanone
{4-Bromo-5-[4-(2-fluoro-benzenesulfonyl)-piperazin-1-yl]-benzofuran-2-yl}-morpholin-4-yl-methanone
{4-Bromo-5-[4-(2-chloro-benzenesulfonyl)-piperazin-1-yl]-benzofuran-2-yl}-piperidin-1-yl-methanone
{4-Bromo-5-[4-(2,6-dichloro-benzenesulfonyl)-piperazin-1-yl]-benzofuran-2-yl}-piperidin-1-yl-methanone
{4-Bromo-5-[4-(2,6-dichloro-benzenesulfonyl)-piperazin-1-yl]-benzofuran-2-yl}-morpholin-4-yl-methanone
5-[4-(3,5-Dichloro-2-hydroxy-benzyl)-piperazin-1-yl]-4-methyl-benzofuran-2-carboxylic acid
4-Methyl-5-[4-(2,3,6-trichloro-benzyl)-piperazin-1-yl]-benzofuran-2-carboxylic acid
5-[4-(2,3-Dichloro-benzyl)-piperazin-1-yl]-4-methyl-benzofuran-2-carboxylic acid
4-Chloro-5-[4-(2,6-dichloro-benzoyl)-piperazin-1-yl]-benzofuran-2-carboxylic acid
{4-Chloro-5-[4-(2,3-dichloro-benzenesulfonyl)-piperazin-1-yl]-benzofuran-2-yl}-morpholin-4-yl-methanone
{4-Bromo-5-[4-(2,6-dichloro-benzenesulfonyl)-piperazin-1-yl]-benzofuran-2-yl}-(4-methyl-piperazin-1-yl)-methanone
4-Bromo-5-[4-(2,6-dichloro-benzenesulfonyl)-piperazin-1-yl]-benzofuran-2-carboxylic acid (2-dimethylamino-ethyl)-amide
4-Chloro-5-[4-(2-hydroxy-benzyl)-piperazin-1-yl]-benzofuran-2-carboxylic acid
{5-[4-(2,6-Dichloro-benzyl)-piperazin-1-yl]-4-methyl-benzofuran-2-yl}-morpholin-4-yl-methanone
4-Chloro-5-[4-(2-chloro-6-hydroxy-benzyl)-piperazin-1-yl]-benzofuran-2-carboxylic acid
4-Chloro-5-[4-(2-chloro-6-methoxy-benzyl)-piperazin-1-yl]-benzofuran-2-carboxylic acid
4-Chloro-5-[4-(3-ethoxy-2-hydroxy-benzyl)-piperazin-1-yl]-benzofuran-2-carboxylic acid
4-Chloro-5-[4-(2-chloro-3-trifluoromethyl-benzyl)-piperazin-1-yl]-benzofuran-2-carboxylic acid
5-{4-[3-(2,6-Dichloro-phenyl)-5-isopropyl-isoxazol-4-ylmethyl]-piperazin-1-yl}-4-methyl-benzofuran-2-carboxylic acid 5-[4-(2,6-Dichloro-benzyl)-piperazin-1-yl]-4-methyl-benzofuran-2-carboxylic acid amide 4-[2-(1H-tetrazol-5-yl)-benzofuran-5-yl]-piperazine-1-carboxylic acid terbutyl ester 5-(4-Benzhydryl-piperazin-1-yl)-4-methyl-benzofuran-2-carboxylic acid or 4-Chloro-5-[4-(2-methyl-5-thiophen-2-yl-2H-pyrazol-3-ylmethyl)-piperazin-1-yl]-benzofuran-2-carboxylic acid or a stereoisomeric form thereof, or a mixture of stereoisomeric forms thereof or a pharmaceutically acceptable salt thereof.

2. A pharmaceutical composition, comprising a compound according to claim 1 and one or more pharmaceutically acceptable excipients.

3. A pharmaceutically acceptable salt of a compound of claim 1.

4. A compound of claim 1, which is 4-(4-Bromo-2-ethoxycarbonyl-benzofuran-5-yl)-piperazine-1-carboxylic acid tert-butyl ester 4-(4-Bromo-2-carboxy-benzofuran-5-yl)-piperazine-1-carboxylic acid tert-butyl ester 5-[4-(3-Methoxy-benzenesulfonyl)-piperazin-1-yl]-benzofuran-2-carboxylic acid amide 5-[4-(4-Methoxy-benzenesulfonyl)-piperazin-1-yl]-benzofuran-2-carboxylic acid amide 5-[4-(3-Trifluoromethyl-benzyl)-piperazin-1-yl]-benzofuran-2-carboxylic acid amide 5-[4-(3-Chloro-benzyl)-piperazin-1-yl]-benzofuran-2-carboxylic acid amide 5-[4-(3-Fluoro-benzoyl)-piperazin-1-yl]-benzofuran-2-carboxylic acid amide 5-[4-(3-Chloro-benzenesulfonyl)-piperazin-1-yl]-benzofuran-2-carboxylic acid amide 4-Bromo-5-[4-(4-methoxy-benzenesulfonyl)-piperazin-1-yl]-benzofuran-2-carboxylic acid amide 5-(4-Benzenesulfonyl-piperazin-1-yl)-benzofuran-2-carboxylic acid 4-Bromo-5-[4-(3-fluoro-benzoyl)-piperazin-1-yl]-benzofuran-2-carboxylic acid 4-Bromo-5-[4-(3-chloro-benzenesulfonyl)-piperazin-1-yl]-benzofuran-2-carboxylic acid 4-Bromo-5-[4-(3-fluoro-benzenesulfonyl)-piperazin-1-yl]-benzofuran-2-carboxylic acid 4-Bromo-5-[4-(pyrrolidine-1-carbonyl)-piperazin-1-yl]-benzofuran-2-carboxylic acid 4-Bromo-5-[4-(3-chloro-benzyl)-piperazin-1-yl]-benzofuran-2-carboxylic acid 2-[4-(4-Bromo-2-carboxy-benzofuran-5-yl)-piperazine-1-carbonyl]-pyrrolidine-1-carboxylic acid tert-butyl ester 4-(4-Chloro-2-ethoxycarbonyl-benzofuran-5-yl)-piperazine-1-carboxylic acid tert-butyl ester 4-(2-Carboxy-4-chloro-benzofuran-5-yl)-piperazine-1-carboxylic acid tert-butyl ester 4-Bromo-5-[4-(3-trifluoromethyl-benzyl)-piperazin-1-yl]-benzofuran-2-carboxylic acid 5-[4-(3-Methoxy-benzenesulfonyl)-piperazin-1-yl]-benzofuran-2-carboxylic acid 4-Bromo-5-[4-(3-methoxy-benzenesulfonyl)-piperazin-1-yl]-benzofuran-2-carboxylic acid 4-Bromo-5-[4-(4-methoxy-benzenesulfonyl)-piperazin-1-yl]-benzofuran-2-carboxylic acid 4-Bromo-5-[4-(pyrrolidine-2-carbonyl)-piperazin-1-yl]-benzofuran-2-carboxylic acid 5-[4-(Adamantane-1-carbonyl)-piperazin-1-yl]-4-bromo-benzofuran-2-carboxylic acid 4-Bromo-5-[4-(3-chloro-benzoyl)-piperazin-1-yl]-benzofuran-2-carboxylic acid 4-Bromo-5-[4-(2-fluoro-benzyl)-piperazin-1-yl]-benzofuran-2-carboxylic acid 4-Bromo-5-[4-(3-fluoro-benzyl)-piperazin-1-yl]-benzofuran-2-carboxylic acid 5-(4-Benzoyl-piperazin-1-yl)-4-bromo-benzofuran-2-carboxylic acid 5-[4-(3,5-Difluoro-benzyl)-piperazin-1-yl]-benzofuran-2-carboxylic acid amide 4-Bromo-5-[4-(2-chloro-benzenesulfonyl)-piperazin-1-yl]-benzofuran-2-carboxylic acid 4-Bromo-5-[4-(4-chloro-benzenesulfonyl)-piperazin-1-yl]-benzofuran-2-carboxylic acid 4-Bromo-5-[4-(4-fluoro-benzyl)-piperazin-1-yl]-benzofuran-2-carboxylic acid 4-Bromo-5-[4-(2-chloro-benzyl)-piperazin-1-yl]-benzofuran-2-carboxylic acid 4-Bromo-5-[4-(4-chloro-benzyl)-piperazin-1-yl]-benzofuran-2-carboxylic acid 4-Bromo-5-[4-(3-trifluoromethyl-benzyl)-piperazin-1-yl]-benzofuran-2-carboxylic acid amide 5-[4-(3-Trifluoromethoxy-benzyl)-piperazin-1-yl]-benzofuran-2-carboxylic acid amide 4-Bromo-5-[4-(3-trifluoromethoxy-benzyl)-piperazin-1-yl]-benzofuran-2-carboxylic acid amide 4-Bromo-5-[4-(3-cyano-benzenesulfonyl)-piperazin-1-yl]-benzofuran-2-carboxylic acid 4-Bromo-5-(4-tert-butylcarbamoyl-piperazin-1-yl)-benzofuran-2-carboxylic acid 4-Bromo-5-[4-(3-fluoro-benzenesulfonyl)-piperazin-1-yl]-benzofuran-2-carboxylic acid amide 4-Bromo-5-[4-(3,5-dichloro-benzoyl)-piperazin-1-yl]-benzofuran-2-carboxylic acid amide 4-Bromo-5-[4-(3,5-difluoro-benzyl)-piperazin-1-yl]-benzofuran-2-carboxylic acid amide 4-Bromo-5-(4-pyridin-3-ylmethyl-piperazin-1-yl)-benzofuran-2-carboxylic acid 4-Bromo-5-(4-pyridin-4-ylmethyl-piperazin-1-yl)-benzofuran-2-carboxylic acid 4-Bromo-5-[4-(3-trifluoromethoxy-benzyl)-piperazin-1-yl]-benzofuran-2-carboxylic acid 4-Bromo-5-[4-(3-phenoxy-benzyl)-piperazin-1-yl]-benzofuran-2-carboxylic acid 4-Bromo-5-[4-(3,5-dimethoxy-benzyl)-piperazin-1-yl]-benzofuran-2-carboxylic acid 5-[4-(3-Allyl-2-hydroxy-benzyl)-piperazin-1-yl]-4-bromo-benzofuran-2-carboxylic acid 5-(4-Benzenesulfonyl-piperazin-1-yl)-4-bromo-benzofuran-2-carboxylic acid 4-Chloro-5-[4-(2-chloro-benzyl)-piperazin-1-yl]-benzofuran-2-carboxylic acid 4-Chloro-5-[4-(3-chloro-benzyl)-piperazin-1-yl]-benzofuran-2-carboxylic acid 4-Chloro-5-[4-(4-chloro-benzyl)-piperazin-1-yl]-benzofuran-2-carboxylic acid 4-Chloro-5-[4-(2-fluoro-benzyl)-piperazin-1-yl]-benzofuran-2-carboxylic acid 4-Chloro-5-[4-(3-fluoro-benzyl)-piperazin-1-yl]-benzofuran-2-carboxylic acid 4-Chloro-5-[4-(4-fluoro-benzyl)-piperazin-1-yl]-benzofuran-2-carboxylic acid 4-Chloro-5-[4-(3-trifluoromethyl-benzyl)-piperazin-1-yl]-benzofuran-2-carboxylic acid 4-Chloro-5-[4-(3-trifluoromethoxy-benzyl)-piperazin-1-yl]-benzofuran-2-carboxylic acid 5-[4-(3-Carboxy-benzyl)-piperazin-1-yl]-4-chloro-benzofuran-2-carboxylic acid
4-Chloro-5-(4-pyridin-3-ylmethyl-piperazin-1-yl)-benzofuran-2-carboxylic acid
4-Chloro-5-[4-(2-chloro-benzenesulfonyl)-piperazin-1-yl]-benzofuran-2-carboxylic acid
4-Chloro-5-[4-(3-chloro-benzenesulfonyl)-piperazin-1-yl]-benzofuran-2-carboxylic acid
4-Chloro-5-[4-(4-chloro-benzenesulfonyl)-piperazin-1-yl]-benzofuran-2-carboxylic acid
4-Chloro-5-[4-(4-methoxy-benzenesulfonyl)-piperazin-1-yl]-benzofuran-2-carboxylic acid
4-Chloro-5-[4-(3-methoxy-benzenesulfonyl)-piperazin-1-yl]-benzofuran-2-carboxylic acid
4-Chloro-5-[4-(3-fluoro-benzoyl)-piperazin-1-yl]-benzofuran-2-carboxylic acid
4-Chloro-5-[4-(3,5-dichloro-benzoyl)-piperazin-1-yl]-benzofuran-2-carboxylic acid
4-Chloro-5-[4-(3-fluoro-benzenesulfonyl)-piperazin-1-yl]-benzofuran-2-carboxylic acid
4-Chloro-5-[4-(3-cyano-benzenesulfonyl)-piperazin-1-yl]-benzofuran-2-carboxylic acid
4-Bromo-5-[4-(2-chloro-benzenesulfonyl)-piperazin-1-yl]-benzofuran-2-carboxylic acid amide
4-Bromo-5-[4-(3-trifluoromethyl-benzoyl)-piperazin-1-yl]-benzofuran-2-carboxylic acid
4-Bromo-5-[4-(3-trifluoromethoxy-benzoyl)-piperazin-1-yl]-benzofuran-2-carboxylic acid
4-Bromo-5-[4-(3-methoxy-benzoyl)-piperazin-1-yl]-benzofuran-2-carboxylic acid
4-Bromo-5-[4-(2,5-dichloro-benzoyl)-piperazin-1-yl]-benzofuran-2-carboxylic acid
4-Bromo-5-[4-(3,5-dichloro-benzoyl)-piperazin-1-yl]-benzofuran-2-carboxylic acid
4-Bromo-5-[4-(2-methyl-1H-benzoimidazole-4-carbonyl)-piperazin-1-yl]-benzofuran-2- carboxylic acid
4-Chloro-5-[4-(3-chloro-benzoyl)-piperazin-1-yl]-benzofuran-2-carboxylic acid
4-Chloro-5-[4-(2,5-dichloro-benzoyl)-piperazin-1-yl]-benzofuran-2-carboxylic acid
4-Chloro-5-[4-(3-methoxy-benzoyl)-piperazin-1-yl]-benzofuran-2-carboxylic acid
4-Chloro-5-[4-(3-trifluoromethyl-benzoyl)-piperazin-1-yl]-benzofuran-2-carboxylic acid
4-Chloro-5-[4-(3-trifluoromethoxy-benzoyl)-piperazin-1-yl]-benzofuran-2-carboxylic acid
4-Chloro-5-[4-(2-methyl-1H-benzoimidazole-4-carbonyl)-piperazin-1-yl]-benzofuran-2-carboxylic acid
5-[4-(1H-Benzoimidazole-5-carbonyl)-piperazin-1-yl]-4-chloro-benzofuran-2-carboxylic acid
4-Chloro-5-[4-(2,5-dichloro-benzyl)-piperazin-1-yl]-benzofuran-2-carboxylic acid
4-Chloro-5-[4-(3,5-dimethoxy-benzyl)-piperazin-1-yl]-benzofuran-2-carboxylic acid
4-Chloro-5-[4-(3-chloro-phenylmethanesulfonyl)-piperazin-1-yl]-benzofuran-2-carboxylic acid
5-[4-(2-Chloro-benzenesulfonyl)-piperazin-1-yl]-4-methyl-benzofuran-2-carboxylic acid
5-[4-(3-Fluoro-benzenesulfonyl)-piperazin-1-yl]-4-methyl-benzofuran-2-carboxylic acid
4-(2-Carboxy-4-methyl-benzofuran-5-yl)-piperazine-1-carboxylic acid tert-butyl ester
{-4-Bromo-5-[4-(2-chloro-benzenesulfonyl)-piperazin-1-yl]-benzofuran-2-yl}-morpholin-4-yl-methanone
4-Bromo-5-[4-(2,5-dichloro-benzenesulfonyl)-piperazin-1-yl]-benzofuran-2-carboxylic acid
4-Bromo-5-[4-(2,5-dichloro-benzyl)-piperazin-1-yl]-benzofuran-2-carboxylic acid
5-[4-(1H-Benzoimidazole-5-carbonyl)-piperazin-1-yl]-4-bromo-benzofuran-2-carboxylic acid
4-Bromo-5-[4-(2,6-dichloro-benzoyl)-piperazin-1-yl]-benzofuran-2-carboxylic acid
5-[4-(2,6-Dichloro-benzoyl)-piperazin-1-yl]-4-methyl-benzofuran-2-carboxylic acid
5-[4-(2,5-Dichloro-benzoyl)-piperazin-1-yl]-4-methyl-benzofuran-2-carboxylic acid
5-[4-(3,5-Dichloro-benzoyl)-piperazin-1-yl]-4-methyl-benzofuran-2-carboxylic acid
4-Methyl-5-[4-(3-trifluoromethoxy-benzoyl)-piperazin-1-yl]-benzofuran-2-carboxylic acid
5-[4-(2-Chloro-benzyl)-piperazin-1-yl]-4-methyl-benzofuran-2-carboxylic acid
5-[4-(3-Chloro-benzyl)-piperazin-1-yl]-4-methyl-benzofuran-2-carboxylic acid
5-[4-(2,5-Dichloro-benzyl)-piperazin-1-yl]-4-methyl-benzofuran-2-carboxylic acid
5-[4-(3-Fluoro-benzyl)-piperazin-1-yl]-4-methyl-benzofuran-2-carboxylic acid
4-Methyl-5-[4-(3-trifluoromethyl-benzyl)-piperazin-1-yl]-benzofuran-2-carboxylic acid
4-Methyl-5-[4-(3-trifluoromethoxy-benzyl)-piperazin-1-yl]-benzofuran-2-carboxylic acid
5-[4-(3-Chloro-benzenesulfonyl)-piperazin-1-yl]-4-methyl-benzofuran-2-carboxylic acid
5-[4-(2,5-Dichloro-benzenesulfonyl)-piperazin-1-yl]-4-methyl-benzofuran-2-carboxylic acid
5-[4-(3-Chloro-phenylmethanesulfonyl)-piperazin-1-yl]-4-methyl-benzofuran-2-carboxylic acid
4-Bromo-5-[4-(2-chloro-6-fluoro-benzyl)-piperazin-1-yl]-benzofuran-2-carboxylic acid
4-Chloro-5-[4-(2-chloro-6-fluoro-benzyl)-piperazin-1-yl]-benzofuran-2-carboxylic acid
4-Bromo-5-[4-(3-chloro-phenylmethanesulfonyl)-piperazin-1-yl]-benzofuran-2-carboxylic acid
4-Bromo-5-[4-(2-fluoro-benzenesulfonyl)-piperazin-1-yl]-benzofuran-2-carboxylic acid
5-[4-(2-Fluoro-benzenesulfonyl)-piperazin-1-yl]-4-methyl-benzofuran-2-carboxylic acid
4-Bromo-5-[4-(2,6-dichloro-benzenesulfonyl)-piperazin-1-yl]-benzofuran-2-carboxylic acid
5-[4-(2,6-Dichloro-benzenesulfonyl)-piperazin-1-yl]-4-methyl-benzofuran-2-carboxylic acid
4-Chloro-5-[4-(2,6-dichloro-benzenesulfonyl)-piperazin-1-yl]-benzofuran-2-carboxylic acid
4-Bromo-5-[4-(2,3-dichloro-benzenesulfonyl)-piperazin-1-yl]-benzofuran-2-carboxylic acid
5-[4-(2,3-Dichloro-benzenesulfonyl)-piperazin-1-yl]-4-methyl-benzofuran-2-carboxylic acid
4-Chloro-5-[4-(2,3-dichloro-benzenesulfonyl)-piperazin-1-yl]-benzofuran-2-carboxylic acid
4-Chloro-5-[4-(2,5-dichloro-benzenesulfonyl)-piperazin-1-yl]-benzofuran-2-carboxylic acid
4-Bromo-5-[4-(2,3-dichloro-benzoyl)-piperazin-1-yl]-benzofuran-2-carboxylic acid
4-Methyl-5-[4-(3-trifluoromethyl-benzoyl)-piperazin-1-yl]-benzofuran-2-carboxylic acid
4-Methyl-5-[4-(2-methyl-1H-benzoimidazole-4-carbonyl)-piperazin-1-yl]-benzofuran-2-carboxylic acid
5-[4-(2-Fluoro-benzyl)-piperazin-1-yl]-4-methyl-benzofuran-2-carboxylic acid
5-[4-(2-Chloro-6-fluoro-benzyl)-piperazin-1-yl]-4-methyl-benzofuran-2-carboxylic acid 5-[4-(2,6-Dichloro-benzyl)-piperazin-1-yl]-4-methyl-benzofuran-2-carboxylic acid
4-Bromo-5-[4-(3,5-dichloro-benzyl)-piperazin-1-yl]-benzofuran-2-carboxylic acid
5-[4-(3,5-Dichloro-benzyl)-piperazin-1-yl]-4-methyl-benzofuran-2-carboxylic acid
4-Chloro-5-[4-(3,5-dichloro-benzyl)-piperazin-1-yl]-benzofuran-2-carboxylic acid
5-[4-(3-Allyl-2-hydroxy-benzyl)-piperazin-1-yl]-4-methyl-benzofuran-2-carboxylic acid
5-[4-(2,3-Dimethoxy-benzyl)-piperazin-1-yl]-4-methyl-benzofuran-2-carboxylic acid
4-Bromo-5-[4-(5-chloro-thiophen-2-ylmethyl)-piperazin-1-yl]-benzofuran-2-carboxylic acid
4-(2-Carboxy-4-cyano-benzofuran-5-yl)-piperazine-1-carboxylic acid tert-butyl ester
4-Bromo-5-[4-(3-ethoxy-benzyl)-piperazin-1-yl]-benzofuran-2-carboxylic acid
5-[4-(3,5-Dichloro-2-hydroxy-benzenesulfonyl)-piperazin-1-yl]-4-methyl-benzofuran-2-carboxylic acid
5-(4-Benzo[1,3]dioxol-4-ylmethyl-piperazin-1-yl)-4-bromo-benzofuran-2-carboxylic acid
4-Bromo-5-[4-(2,6-dichloro-benzyl)-piperazin-1-yl]-benzofuran-2-carboxylic acid
4-Bromo-5-[4-(2,4-dichloro-benzyl)-piperazin-1-yl]-benzofuran-2-carboxylic acid
4-Bromo-5-[4-(2-trifluoromethyl-benzyl)-piperazin-1-yl]-benzofuran-2-carboxylic acid
5-[4-(3-Allyl-2-methoxy-benzyl)-piperazin-1-yl]-4-methyl-benzofuran-2-carboxylic acid
4-Bromo-5-[4-(3-tert-butyl-2-hydroxy-benzyl)-piperazin-1-yl]-benzofuran-2-carboxylic acid
4-Methyl-5-(4-naphthalen-1-ylmethyl-piperazin-1-ly)-benzofuran-2-carboxylic acid
4-Bromo-5-[4-(2-hydroxy-naphthalen-1-ylmethyl)-piperazin-1-yl]-benzofuran-2-carboxylic acid
4-Bromo-5-[4-(2-trifluoromethyl-benzenesulfonyl)-piperazin-1-yl]-benzofuran-2-carboxylic acid
4-Bromo-5-[4-(3-trifluoromethyl-benzenesulfonyl)-piperazin-1-yl]-benzofuran-2-carboxylic acid
{5-[4-(3,5-Dichloro-2-hydroxy-benzenesulfonyl)-piperazin-1-yl]-4-methyl-benzofuran-2-yl}-morpholin-4-yl-methanone
{4-Bromo-5-[4-(2-fluoro-benzenesulfonyl)-piperazin-1-yl]-benzofuran-2-yl}-morpholin-4-yl-methanone
{4-Bromo-5-[4-(2-chloro-benzenesulfonyl)-piperazin-1-yl]-benzofuran-2-yl}-piperidin-1-yl-methanone
{4-Bromo-5-[4-(2,6-dichloro-benzenesulfonyl)-piperazin-1-yl]-benzofuran-2-yl}-piperidin-1-yl-methanone
{4-Bromo-5-[4-(2,6-dichloro-benzenesulfonyl)-piperazin-1-yl]-benzofuran-2-yl}-morpholin-4-yl-methanone
5-[4-(3,5-Dichloro-2-hydroxy-benzyl)-piperazin-1-yl]-4-methyl-benzofuran-2-carboxylic acid
4-Methyl-5-[4-(2,3,6-trichloro-benzyl)-piperazin-1-yl]-benzofuran-2-carboxylic acid
5-[4-(2,3-Dichloro-benzyl)-piperazin-1-yl]-4-methyl-benzofuran-2-carboxylic acid
4-Chloro-5-[4-(2,6-dichloro-benzoyl)-piperazin-1-yl]-benzofuran-2-carboxylic acid
{4-Chloro-5-[4-(2,3-dichloro-benzenesulfonyl)-piperazin-1-yl]-benzofuran-2-yl}-morpholin-4-yl-methanone
4-Bromo-5-[4-(2,6-dichloro-benzenesulfonyl)-piperazin-1-yl]-benzofuran-2-carboxylic acid (2-dimethylaminoethyl)-amide
4-Chloro-5-[4-(2-hydroxy-benzyl)-piperazin-1-yl]-benzofuran-2-carboxylic acid
{5-[4-(2,6-Dichloro-benzyl)-piperazin-1-yl]-4-methyl-benzofuran-2-yl}-morpholin-4-yl-methanone
4-Chloro-5-[4-(2-chloro-6-hydroxy-benzyl)-piperazin-1-yl]-benzofuran-2-carboxylic acid
4-Chloro-5-[4-(2-chloro-6-methoxy-benzyl)-piperazin-1-yl]-benzofuran-2-carboxylic acid
4-Chloro-5-[4-(3-ethoxy-2-hydroxy-benzyl)-piperazin-1-yl]-benzofuran-2-carboxylic acid
4-Chloro-5-[4-(2-chloro-3-trifluoromethyl-benzyl)-piperazin-1-yl]-benzofuran-2-carboxylic acid
5-[4-(2,6-Dichloro-benzyl)-piperazin-1-yl]-4-methyl-benzofuran-2-carboxylic acid amide
5-(4-Benzhydryl-piperazin-1-yl)-4-methyl-benzofuran-2-carboxylic acid or
4-Chloro-5-[4-(2-methyl-5-thiophen-2-yl-2H-pyrazol-3-ylmethyl)-piperazin-1-yl]-benzofuran-2-carboxylic acid or a pharmaceutically acceptable salt thereof.

5. A pharmaceutical composition, comprising a compound according to claim 4 and one or more pharmaceutically acceptable excipients.

6. A compound of claim 1, which is 5-[4-(2,6-Dichloro-benzenesulfonyl)-piperazin-1-yl]-4-methyl-benzofuran-2-carboxylic acid or a pharmaceutically acceptable salt thereof.

7. A pharmaceutical composition, comprising a compound according to claim 6 and one or more pharmaceutically acceptable excipients.

8. A compound of claim 1, which is
4-(4-Bromo-2-ethoxycarbonyl-benzofuran-5-yl)-piperazine-1-carboxylic acid tert-butyl ester
4-(4-Bromo-2-carboxy-benzofuran-5-yl)-piperazine-1-carboxylic acid tert-butyl ester
5-[4-(3-Methoxy-benzenesulfonyl)-piperazin-1-yl]-benzofuran-2-carboxylic acid amide
5-[4-(4-Methoxy-benzenesulfonyl)-piperazin-1-yl]-benzofuran-2-carboxylic acid amide
5-[4-(3-Trifluoromethyl-benzyl)-piperazin-1-yl]-benzofuran-2-carboxylic acid amide
5-[4-(3-Chloro-benzyl)-piperazin-1-yl]-benzofuran-2-carboxylic acid amide
5-[4-(3-Fluoro-benzoyl)-piperazin-1-yl]-benzofuran-2-carboxylic acid amide
5-[4-(3-Chloro-benzenesulfonyl)-piperazin-1-yl]-benzofuran-2-carboxylic acid amide or
4-Bromo-5-[4-(4-methoxy-benzenesulfonyl)-piperazin-1-yl]-benzofuran-2-carboxylic acid amide or a pharmaceutically acceptable salt thereof.

9. A compound of claim 1, which is
5-(4-Benzenesulfonyl-piperazin-1-yl)-benzofuran-2-carboxylic acid
4-Bromo-5-[4-(3-fluoro-benzoyl)-piperazin-1-yl]-benzofuran-2-carboxylic acid
4-Bromo-5-[4-(3-chloro-benzenesulfonyl)-piperazin-1-yl]-benzofuran-2-carboxylic acid
4-Bromo-5-[4-(3-fluoro-benzenesulfonyl)-piperazin-1-yl]-benzofuran-2-carboxylic acid
4-Bromo-5-[4-(pyrrolidine-1-carbonyl)-piperazin-1-yl]-benzofuran-2-carboxylic acid
4-Bromo-5-[4-(3-chloro-benzyl)-piperazin-1-yl]-benzofuran-2-carboxylic acid or
2-[4-(4-Bromo-2-carboxy-benzofuran-5-yl)-piperazine-1-carbonyl]-pyrrolidine-1-carboxylic acid tert-butyl ester or a pharmaceutically acceptable salt thereof.

10. A compound of claim 1, which is 4-(4-Chloro-2-ethoxycarbonyl-benzofuran-5-yl)-piperazine-1-carboxylic acid tert-butyl ester 4-(2-Carboxy-4-chloro-benzofuran-5-yl)-piperazine-1-carboxylic acid tert-butyl ester 4-Bromo-5-[4-(3-trifluoromethyl-benzyl)-piperazin-1-yl]-benzofuran-2-carboxylic acid 5-[4-(3-Methoxy-benzenesulfonyl)-piperazin-1-yl]-benzofuran-2-carboxylic acid 4-Bromo-5-[4-(3-methoxy-benzenesulfonyl)-piperazin-1-yl]-benzofuran-2-carboxylic acid 4-Bromo-5-[4-(4-methoxy-benzenesulfonyl)-piperazin-1-yl]-benzofuran-2-carboxylic acid 4-Bromo-5-[4-(pyrrolidine-2-carbonyl)-piperazin-1-yl]-benzofuran-2-carboxylic acid 5-[4-(Adamantane-1-carbonyl)-piperazin-1-yl]-4-bromo-benzofuran-2-carboxylic acid 4-Bromo-5-[4-(3-chloro-benzoyl)-piperazin-1-yl]-benzofuran-2-carboxylic acid 4-Bromo-5-[4-(2-fluoro-benzyl)-piperazin-1-yl]-benzofuran-2-carboxylic acid 4-Bromo-5-[4-(3-fluoro-benzyl)-piperazin-1-yl]-benzofuran-2-carboxylic acid 5-(4-Benzoyl-piperazin-1-yl)-4-bromo-benzofuran-2-carboxylic acid or 5-[4-(3,5-Difluoro-benzyl)-piperazin-1-yl]-benzofuran-2-carboxylic acid amide or a pharmaceutically acceptable salt thereof.

11. A compound of claim 1, which is

4-Bromo-5-[4-(2-chloro-benzenesulfonyl)-piperazin-1-yl]-benzofuran-2-carboxylic acid 4-Bromo-5-[4-(4-chloro-benzenesulfonyl)-piperazin-1-yl]-benzofuran-2-carboxylic acid 4-Bromo-5-[4-(4-fluoro-benzyl)-piperazin-1-yl]-benzofuran-2-carboxylic acid 4-Bromo-5-[4-(2-chloro-benzyl)-piperazin-1-yl]-benzofuran-2-carboxylic acid 4-Bromo-5-[4-(4-chloro-benzyl)-piperazin-1-yl]-benzofuran-2-carboxylic acid 4-Bromo-5-[4-(3-trifluoromethyl-benzyl)-piperazin-1-yl]-benzofuran-2-carboxylic acid amide 5-[4-(3-Trifluoromethoxy-benzyl)-piperazin-1-yl]-benzofuran-2-carboxylic acid amide 4-Bromo-5-[4-(3-trifluoromethoxy-benzyl)-piperazin-1-yl]-benzofuran-2-carboxylic acid amide 4-Bromo-5-[4-(3-cyano-benzenesulfonyl)-piperazin-1-yl]-benzofuran-2-carboxylic acid 4-Bromo-5-(4-tert-butylcarbamoyl-piperazin-1-yl)-benzofuran-2-carboxylic acid 4-Bromo-5-[4-(3-fluoro-benzenesulfonyl)-piperazin-1-yl]-benzofuran-2-carboxylic acid amide or 4-Bromo-5-[4-(3,5-dichloro-benzoyl)-piperazin-1-yl]-benzofuran-2-carboxylic acid amide or a pharmaceutically acceptable salt thereof.

12. A compound of claim 1, which is

4-Bromo-5-[4-(3,5-difluoro-benzyl)-piperazin-1-yl]-benzofuran-2-carboxylic acid amide 4-Bromo-5-(4-pyridin-3-ylmethyl-piperazin-1-yl)-benzofuran-2-carboxylic acid 4-Bromo-5-(4-pyridin-4-ylmethyl-piperazin-1-yl)-benzofuran-2-carboxylic acid 4-Bromo-5-[4-(3-trifluoromethoxy-benzyl)-piperazin-1-yl]-benzofuran-2-carboxylic acid 4-Bromo-5-[4-(3-phenoxy-benzyl)-piperazin-1-yl]-benzofuran-2-carboxylic acid 4-Bromo-5-[4-(3,5-dimethoxy-benzyl)-piperazin-1-yl]-benzofuran-2-carboxylic acid 5-[4-(3-Allyl-2-hydroxy-benzyl)-piperazin-1-yl]-4-bromo-benzofuran-2-carboxylic acid 5-(4-Benzenesulfonyl-piperazin-1-yl)-4-bromo-benzofuran-2-carboxylic acid 4-Chloro-5-[4-(2-chloro-benzyl)-piperazin-1-yl]-benzofuran-2-carboxylic acid 4-Chloro-5-[4-(3-chloro-benzyl)-piperazin-1-yl]-benzofuran-2-carboxylic acid 4-Chloro-5-[4-(4-chloro-benzyl)-piperazin-1-yl]-benzofuran-2-carboxylic acid 4-Chloro-5-[4-(2-fluoro-benzyl)-piperazin-1-yl]-benzofuran-2-carboxylic acid 4-Chloro-5-[4-(3-fluoro-benzyl)-piperazin-1-yl]-benzofuran-2-carboxylic acid or 4-Chloro-5-[4-(4-fluoro-benzyl)-piperazin-1-yl]-benzofuran-2-carboxylic acid or a pharmaceutically acceptable salt thereof.

13. A compound of claim 1, which is

4-Chloro-5-[4-(3-trifluoromethyl-benzyl)-piperazin-1-yl]-benzofuran-2-carboxylic acid 4-Chloro-5-[4-(3-trifluoromethoxy-benzyl)-piperazin-1-yl]-benzofuran-2-carboxylic acid 5-[4-(3-Carboxy-benzyl)-piperazin-1-yl]-4-chloro-benzofuran-2-carboxylic acid 4-Chloro-5-(4-pyridin-3-ylmethyl-piperazin-1-yl)-benzofuran-2-carboxylic acid 4-Chloro-5-[4-(2-chloro-benzenesulfonyl)-piperazin-1-yl]-benzofuran-2-carboxylic acid 4-Chloro-5-[4-(3-chloro-benzenesulfonyl)-piperazin-1-yl]-benzofuran-2-carboxylic acid 4-Chloro-5-[4-(4-chloro-benzenesulfonyl)-piperazin-1-yl]-benzofuran-2-carboxylic acid 4-Chloro-5-[4-(4-methoxy-benzenesulfonyl)-piperazin-1-yl]-benzofuran-2-carboxylic acid 4-Chloro-5-[4-(3-methoxy-benzenesulfonyl)-piperazin-1-yl]-benzofuran-2-carboxylic acid 4-Chloro-5-[4-(3-fluoro-benzoyl)-piperazin-1-yl]-benzofuran-2-carboxylic acid 4-Chloro-5-[4-(3,5-dichloro-benzoyl)-piperazin-1-yl]-benzofuran-2-carboxylic acid 4-Chloro-5-[4-(3-fluoro-benzenesulfonyl)-piperazin-1-yl]-benzofuran-2-carboxylic acid 4-Chloro-5-[4-(3-cyano-benzenesulfonyl)-piperazin-1-yl]-benzofuran-2-carboxylic acid or 4-Bromo-5-[4-(2-chloro-benzenesulfonyl)-piperazin-1-yl]-benzofuran-2-carboxylic acid amide or a pharmaceutically acceptable salt thereof.

14. A compound of claim 1, which is

4-Bromo-5-[4-(3-fluoro-benzenesulfonyl)-piperazin-1-yl]-benzofuran-2-carboxylic acid ethoxy-amide 4-Bromo-5-[4-(3-trifluoromethyl-benzoyl)-piperazin-1-yl]-benzofuran-2-carboxylic acid 4-Bromo-5-[4-(3-trifluoromethoxy-benzoyl)-piperazin-1-yl]-benzofuran-2-carboxylic acid 4-Bromo-5-[4-(3-methoxy-benzoyl)-piperazin-1-yl]-benzofuran-2-carboxylic acid 4-Bromo-5-[4-(2,5-dichloro-benzoyl)-piperazin-1-yl]-benzofuran-2-carboxylic acid 4-Bromo-5-[4-(3,5-dichloro-benzoyl)-piperazin-1-yl]-benzofuran-2-carboxylic acid 4-Bromo-5-[4-(2-methyl-1H-benzoimidazole-4-carbonyl)-piperazin-1-yl]-benzofuran-2-carboxylic acid 4-Chloro-5-[4-(3-chloro-benzoyl)-piperazin-1-yl]-benzofuran-2-carboxylic acid 4-Chloro-5-[4-(2,5-dichloro-benzoyl)-piperazin-1-yl]-benzofuran-2-carboxylic acid 4-Chloro-5-[4-(3-methoxy-benzoyl)-piperazin-1-yl]-benzofuran-2-carboxylic acid
4-Chloro-5-[4-(3-trifluoromethyl-benzoyl)-piperazin-1-yl]-benzofuran-2-carboxylic acid
4-Chloro-5-[4-(3-trifluoromethoxy-benzoyl)-piperazin-1-yl]-benzofuran-2-carboxylic acid or
4-Chloro-5-[4-(2-methyl-1H-benzoimidazole-4-carbonyl)-piperazin-1-yl]-benzofuran-2-carboxylic acid
or a pharmaceutically acceptable salt thereof.

15. A compound of claim 1, which is
5-[4-(1H-Benzoimidazole-5-carbonyl)-piperazin-1-yl]-4-chloro-benzofuran-2-carboxylic acid
4-Chloro-5-[4-(2,5-dichloro-benzyl)-piperazin-1-yl]-benzofuran-2-carboxylic acid
4-Chloro-5-[4-(3,5-dimethoxy-benzyl)-piperazin-1-yl]-benzofuran-2-carboxylic acid
4-Chloro-5-[4-(3-chloro-phenylmethanesulfonyl)-piperazin-1-yl]-benzofuran-2-carboxylic acid
5-[4-(2-Chloro-benzenesulfonyl)-piperazin-1-yl]-4-methyl-benzofuran-2-carboxylic acid
5-[4-(3-Fluoro-benzenesulfonyl)-piperazin-1-yl]-4-methyl-benzofuran-2-carboxylic acid or
4-(2-Carboxy-4-methyl-benzofuran-5-yl)-piperazine-1-carboxylic acid tert-butyl ester
or a pharmaceutically acceptable salt thereof.

16. A compound of claim 1, which is
{4-Bromo-5-[4-(2-chloro-benzenesulfonyl)-piperazin-1-yl]-benzofuran-2-yl}-morpholin-4-yl-methanone
4-Bromo-5-[4-(2-chloro-benzenesulfonyl)-piperazin-1-yl]-benzofuran-2-carboxylic acid (2-methoxy-ethyl)-amide
4-Bromo-5-[4-(2,5-dichloro-benzenesulfonyl)-piperazin-1-yl]-benzofuran-2-carboxylic acid
4-Bromo-5-[4-(2,5-dichloro-benzyl)-piperazin-1-yl]-benzofuran-2-carboxylic acid
5-[4-(1H-Benzoimidazole-5-carbonyl)-piperazin-1-yl]-4-bromo-benzofuran-2-carboxylic acid
4-Bromo-5-[4-(2,6-dichloro-benzoyl)-piperazin-1-yl]-benzofuran-2-carboxylic acid
5-[4-(2,6-Dichloro-benzoyl)-piperazin-1-yl]-4-methyl-benzofuran-2-carboxylic acid
5-[4-(2,5-Dichloro-benzoyl)-piperazin-1-yl]-4-methyl-benzofuran-2-carboxylic acid
5-[4-(3,5-Dichloro-benzoyl)-piperazin-1-yl]-4-methyl-benzofuran-2-carboxylic acid
4-Methyl-5-[4-(3-trifluoromethoxy-benzoyl)-piperazin-1-yl]-benzofuran-2-carboxylic acid
5-[4-(2-Chloro-benzyl)-piperazin-1-yl]-4-methyl-benzofuran-2-carboxylic acid
5-[4-(3-Chloro-benzyl)-piperazin-1-yl]-4-methyl-benzofuran-2-carboxylic acid
5-[4-(2,5-Dichloro-benzyl)-piperazin-1-yl]-4-methyl-benzofuran-2-carboxylic acid
5-[4-(3-Fluoro-benzyl)-piperazin-1-yl]-4-methyl-benzofuran-2-carboxylic acid
4-Methyl-5-[4-(3-trifluoromethyl-benzyl)-piperazin-1-yl]-benzofuran-2-carboxylic acid
4-Methyl-5-[4-(3-trifluoromethoxy-benzyl)-piperazin-1-yl]-benzofuran-2-carboxylic acid or
5-[4-(3-Chloro-benzenesulfonyl)-piperazin-1-yl]-4-methyl-benzofuran-2-carboxylic acid
or a pharmaceutically acceptable salt thereof.

17. A compound of claim 1, which is
5-[4-(2,5-Dichloro-benzenesulfonyl)-piperazin-1-yl]-4-methyl-benzofuran-2-carboxylic acid
5-[4-(3-Chloro-phenylmethanesulfonyl)-piperazin-1-yl]-4-methyl-benzofuran-2-carboxylic acid
4-Bromo-5-[4-(2-chloro-6-fluoro-benzyl)-piperazin-1-yl]-benzofuran-2-carboxylic acid
4-Chloro-5-[4-(2-chloro-6-fluoro-benzyl)-piperazin-1-yl]-benzofuran-2-carboxylic acid
4-Bromo-5-[4-(3-chloro-phenylmethanesulfonyl)-piperazin-1-yl]-benzofuran-2-carboxylic acid
4-Bromo-5-[4-(2-fluoro-benzenesulfonyl)-piperazin-1-yl]-benzofuran-2-carboxylic acid
5-[4-(2-Fluoro-benzenesulfonyl)-piperazin-1-yl]-4-methyl-benzofuran-2-carboxylic acid
4-Bromo-5-[4-(2,6-dichloro-benzenesulfonyl)-piperazin-1-yl]-benzofuran-2-carboxylic acid
5-[4-(2,6-Dichloro-benzenesulfonyl)-piperazin-1-yl]-4-methyl-benzofuran-2-carboxylic acid
4-Chloro-5-[4-(2,6-dichloro-benzenesulfonyl)-piperazin-1-yl]-benzofuran-2-carboxylic acid
4-Bromo-5-[4-(2,3-dichloro-benzenesulfonyl)-piperazin-1-yl]-benzofuran-2-carboxylic acid
5-[4-(2,3-Dichloro-benzenesulfonyl)-piperazin-1-yl]-4-methyl-benzofuran-2-carboxylic acid
4-Chloro-5-[4-(2,3-dichloro-benzenesulfonyl)-piperazin-1-yl]-benzofuran-2-carboxylic acid or
4-Chloro-5-[4-(2,5-dichloro-benzenesulfonyl)-piperazin-1-yl]-benzofuran-2-carboxylic acid
or a pharmaceutically acceptable salt thereof.

18. A compound of claim 1, which is
4-Bromo-5-[4-(2,3-dichloro-benzoyl)-piperazin-1-yl]-benzofuran-2-carboxylic acid
4-Methyl-5-[4-(3-trifluoromethyl-benzoyl)-piperazin-1-yl]-benzofuran-2-carboxylic acid
4-Methyl-5-[4-(2-methyl-1H-benzoimidazole-4-carbonyl)-piperazin-1-yl]-benzofuran-2-carboxylic acid
5-[4-(2-Fluoro-benzyl)-piperazin-1-yl]-4-methyl-benzofuran-2-carboxylic acid
5-[4-(2-Chloro-6-fluoro-benzyl)-piperazin-1-yl]-4-methyl-benzofuran-2-carboxylic acid
5-[4-(2,6-Dichloro-benzyl)-piperazin-1-yl]-4-methyl-benzofuran-2-carboxylic acid
4-Bromo-5-[4-(3,5-dichloro-benzyl)-piperazin-1-yl]-benzofuran-2-carboxylic acid
5-[4-(3,5-Dichloro-benzyl)-piperazin-1-yl]-4-methyl-benzofuran-2-carboxylic acid
4-Chloro-5-[4-(3,5-dichloro-benzyl)-piperazin-1-yl]-benzofuran-2-carboxylic acid
5-[4-(3-Allyl-2-hydroxy-benzyl)-piperazin-1-yl]-4-methyl-benzofuran-2-carboxylic acid
5-[4-(2,3-Dimethoxy-benzyl)-piperazin-1-yl]-4-methyl-benzofuran-2-carboxylic acid
4-Bromo-5-[4-(5-chloro-thiophen-2-ylmethyl)-piperazin-1-yl]-benzofuran-2-carboxylic acid
4-(2-Carboxy-4-cyano-benzofuran-5-yl)-piperazine-1-carboxylic acid tert-butyl ester
4-Bromo-5-[4-(3-ethoxy-benzyl)-piperazin-1-yl]-benzofuran-2-carboxylic acid or
4-Bromo-5-[4-(2-chloro-benzenesulfonyl)-piperazin-1-yl]-benzofuran-2-carboxylic acid benzylamide
or a pharmaceutically acceptable salt thereof.

19. A compound of claim 1, which is
5-[4-(3,5-Dichloro-2-hydroxy-benzenesulfonyl)-piperazin-1-yl]-4-methyl-benzofuran-2-carboxylic acid
5-(4-Benzo[1,3]dioxol-4-ylmethyl-piperazin-1-yl)-4-bromo-benzofuran-2-carboxylic acid
4-Bromo-5-[4-(2,6-dichloro-benzyl)-piperazin-1-yl]-benzofuran-2-carboxylic acid
4-Bromo-5-[4-(2,4-dichloro-benzyl)-piperazin-1-yl]-benzofuran-2-carboxylic acid or 5-[4-(2-Allyloxy-benzyl)-piperazin-1-yl]-4-bromo-benzofuran-2-carboxylic acid or a pharmaceutically acceptable salt thereof.

20. A compound of claim 1, which is

5-{4-[3-(2,6-Dichloro-phenyl)-5-isopropyl-isoxazole-4-carbonyl]-piperazin-1-yl}-4-methyl-benzofuran-2-carboxylic acid 4-Bromo-5-[4-(2-trifluoromethyl-benzyl)-piperazin-1-yl]-benzofuran-2-carboxylic acid 5-[4-(3-Allyloxy-benzyl)-piperazin-1-yl]-4-bromo-benzofuran-2-carboxylic acid 5-[4-(3-Allyl-2-methoxy-benzyl)-piperazin-1-yl]-4-methyl-benzofuran-2-carboxylic acid 4-Bromo-5-[4-(3-tert-butyl-2-hydroxy-benzyl)-piperazin-1-yl]-benzofuran-2-carboxylic acid 4-Methyl-5-(4-naphthalen-1-ylmethyl-piperazin-1-yl)-benzofuran-2-carboxylic acid 4-Bromo-5-[4-(2-hydroxy-naphthalen-1-ylmethyl)-piperazin-1-yl]-benzofuran-2-carboxylic acid 4-Bromo-5-[4-(2-trifluoromethyl-benzenesulfonyl)-piperazin-1-yl]-benzofuran-2-carboxylic acid or 4-Bromo-5-[4-(3-trifluoromethyl-benzenesulfonyl)-piperazin-1-yl]-benzofuran-2-carboxylic acid or a pharmaceutically acceptable salt thereof.

21. A compound of claim 1, which is

{5-[4-(3,5-Dichloro-2-hydroxy-benzenesulfonyl)-piperazin-1-yl]-4-methyl-benzofuran-2-yl}-morpholin-4-yl-methanone {4-Bromo-5-[4-(2-fluoro-benzenesulfonyl)-piperazin-1-yl]-benzofuran-2-yl}-morpholin-4-yl-methanone {4-Bromo-5-[4-(2-chloro-benzenesulfonyl)-piperazin-1-yl]-benzofuran-2-yl}-piperidin-1-yl-methanone {4-Bromo-5-[4-(2,6-dichloro-benzenesulfonyl)-piperazin-1-yl]-benzofuran-2-yl}-piperidin-1-yl-methanone or {4-Bromo-5-[4-(2,6-dichloro-benzenesulfonyl)-piperazin-1-yl]-benzofuran-2-yl}-morpholin-4-yl-methanone or a pharmaceutically acceptable salt thereof.

22. A compound of claim 1, which is

5-[4-(3,5-Dichloro-2-hydroxy-benzyl)-piperazin-1-yl]-4-methyl-benzofuran-2-carboxylic acid 4-Methyl-5-[4-(2,3,6-trichloro-benzyl)-piperazin-1-yl]-benzofuran-2-carboxylic acid 5-[4-(2,3-Dichloro-benzyl)-piperazin-1-yl]-4-methyl-benzofuran-2-carboxylic acid or 4-Chloro-5-[4-(2,6-dichloro-benzoyl)-piperazin-1yl]-benzofuran-2-carboxylic acid or a pharmaceutically acceptable salt thereof.

23. A compound of claim 1, which is

{4-Chloro-5-[4-(2,3-dichloro-benzenesulfonyl)-piperazin-1-yl]-benzofuran-2-yl}-morpholin-4-yl-methanone {4-Bromo-5-[4-(2,6-dichloro-benzenesulfonyl)-piperazin-1-yl]-benzofuran-2-yl}-(4-methyl-piperazin-1-yl)-methanone 4-Bromo-5-[4-(2,6-dichloro-benzenesulfonyl)-piperazin-1-yl]-benzofuran-2-carboxylic acid (2-dimethylamino-ethyl)-amide 4-Chloro-5-[4-(2-hydroxy-benzyl)-piperazin-1-yl]-benzofuran-2-carboxylic acid or {5-[4-(2,6-Dichloro-benzyl)-piperazin-1-yl]-4-methyl-benzofuran-2-yl}-morpholin-4-yl-methanone or a pharmaceutically acceptable salt thereof.

24. A compound of claim 1, which is

4-Chloro-5-[4-(2-chloro-6-hydroxy-benzyl)-piperazin-1-yl]-benzofuran-2-carboxylic acid 4-Chloro-5-[4-(2-chloro-6-methoxy-benzyl)-piperazin-1-yl]-benzofuran-2-carboxylic acid or 4-Chloro-5-[4-(3-ethoxy-2-hydroxy-benzyl)-piperazin-1-yl]-benzofuran-2-carboxylic acid or a pharmaceutically acceptable salt thereof.

25. A compound of claim 1, which is

4-Chloro-5-[4-(2-chloro-3-trifluoromethyl-benzyl)-piperazin-1-yl]-benzofuran-2-carboxylic acid 5-{4-[3-(2,6-Dichloro-phenyl)-5-isopropyl-isoxazol-4-ylmethyl]-piperazin-1-yl}-4-methyl-benzofuran-2-carboxylic acid 5-[4-(2,6-Dichloro-benzyl)-piperazin-1-yl]-4-methyl-benzofuran-2-carboxylic acid amide or or a pharmaceutically acceptable salt thereof.

26. A compound of claim 1, which is

4-[2-(1H-tetrazol-5-yl)-benzofuran-5-yl]-piperazine-1-carboxylic acid terbutyl ester 5-(4-Benzhydryl-piperazin-1-yl)-4-methyl-benzofuran-2-carboxylic acid or 4-Chloro-5-[4-(2-methyl-5-thiophen-2-yl-2H-pyrazol-3-ylmethyl)-piperazin-1-yl]-benzofuran-2-carboxylic acid or a pharmaceutically acceptable salt thereof.

27. A compound, which is 4-(4-Bromo-2-carboxy-benzofuran-5-yl)-piperazine-1-carboxylic acid tert-butyl ester 4-(2-Carboxy-4-chloro-benzofuran-5-yl)-piperazine-1-carboxylic acid tert-butyl ester 4-Bromo-5-(4-pyridin-3-ylmethyl-piperazin-1-yl)-benzofuran-2-carboxylic acid 4-Chloro-5-(4-pyridin-3-ylmethyl-piperazin-1-yl)-benzofuran-2-carboxylic acid 4-Bromo-5-[4-(2,6-dichloro-benzoyl)-piperazin-1-yl]-benzofuran-2-carboxylic acid 5-[4-(2,6-Dichloro-benzoyl)-piperazin-1-yl]-4-methyl-benzofuran-2-carboxylic acid 4-Bromo-5-[4-(2,6-dichloro-benzenesulfonyl)-piperazin-1-yl]-benzofuran-2-carboxylic acid 5-[4-(2,6-Dichloro-benzenesulfonyl)-piperazin-1-yl]-4-methyl-benzofuran-2-carboxylic acid 4-Chloro-5-[4-(2,6-dichloro-benzenesulfonyl)-piperazin-1-yl]-benzofuran-2-carboxylic acid 4-Chloro-5-[4-(2,3-dichloro-benzenesulfonyl)-piperazin-1-yl]-benzofuran-2-carboxylic acid 5-[4-(2-Chloro-6-fluoro-benzyl)-piperazin-1-yl]-4-methyl-benzofuran-2-carboxylic acid 5-[4-(2,6-Dichloro-benzyl)-piperazin-1-yl]-4-methyl-benzofuran-2-carboxylic acid {5-[4-(3,5-Dichloro-2-hydroxy-benzenesulfonyl)-piperazin-1-yl]-4-methyl-benzofuran-2-yl}-morpholin-4-yl-methanone {4-Bromo-5-[4-(2,6-dichloro-benzenesulfonyl)-piperazin-1-yl]-benzofuran-2-yl}-piperidin-1-yl-methanone {4-Bromo-5-[4-(2,6-dichloro-benzenesulfonyl)-piperazin-1-yl]-benzofuran-2-yl}-morpholin-4-yl-methanone {4-Bromo-5-[4-(2,6-dichloro-benzenesulfonyl)-piperazin-1-yl]-benzofuran-2-yl}-(4-methyl-piperazin-1-yl)-methanone 4-Bromo-5-[4-(2,6-dichloro-benzenesulfonyl)-piperazin-1-yl]-benzofuran-2-carboxylic acid (2-dimethylamino-ethyl)-amide {5-[4-(2,6-Dichloro-benzyl)-piperazin-1-yl]-4-methyl-benzofuran-2-yl}-morpholin-4-yl-methanone 5-{4-[3-(2,6-Dichloro-phenyl)-5-isopropyl-isoxazol-4-ylmethyl]-piperazin-1-yl}-4-methyl-benzofuran-2-carboxylic acid 5-[4-(2,6-Dichloro-benzyl)-piperazin-1-yl]-4-methyl-benzofuran-2-carboxylic acid amide or or a pharmaceutically acceptable salt thereof.

28. A pharmaceutical composition, comprising a compound according to claim 27 and one or more pharmaceutically acceptable excipients.

\* \* \* \* \*

UNITED STATES PATENT AND TRADEMARK OFFICE
CERTIFICATE OF CORRECTION

PATENT NO. : 8,575,161 B2  Page 1 of 1
APPLICATION NO. : 12/988147
DATED : November 5, 2013
INVENTOR(S) : Roche et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 366 days.

Signed and Sealed this
Twenty-second Day of September, 2015

Michelle K. Lee
*Director of the United States Patent and Trademark Office*